(12) United States Patent
Aizenberg et al.

(10) Patent No.: US 11,118,067 B2
(45) Date of Patent: *Sep. 14, 2021

(54) SANITATION SYSTEMS AND COMPONENTS THEREOF HAVING A SLIPPERY SURFACE

(71) Applicant: President and Fellows of Harvard College, Cambridge, MA (US)

(72) Inventors: Joanna Aizenberg, Boston, MA (US); Michael Aizenberg, Boston, MA (US); Sung Hoon Kang, Lutherville-Timonium, MD (US); Philseok Kim, Waltham, MA (US); Tak Sing Wong, State College, PA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,526

(22) Filed: Jan. 25, 2018

(65) Prior Publication Data
US 2018/0187022 A1    Jul. 5, 2018

Related U.S. Application Data

(63) Continuation of application No. 15/804,809, filed on Nov. 6, 2017, which is a continuation of application
(Continued)

(51) Int. Cl.
*B05D 3/00* (2006.01)
*C09D 5/00* (2006.01)
(Continued)

(52) U.S. Cl.
CPC .............. *C09D 5/00* (2013.01); *A61L 15/24* (2013.01); *A61L 15/34* (2013.01); *A61L 15/42* (2013.01);
(Continued)

(58) Field of Classification Search
CPC .......... C09D 5/00; C09D 5/16; C09D 5/1656; C09D 5/1681
See application file for complete search history.

(56) References Cited

U.S. PATENT DOCUMENTS 3,068,187 A   12/1962 Bolstad et al.
3,274,007 A    9/1966 Jones
(Continued)

FOREIGN PATENT DOCUMENTS

CN    1360618 A    7/2002
CN    1884398 A   12/2006
(Continued)

OTHER PUBLICATIONS

Abbott, et al., "Mass Production of Bio-Inspired Structured Surfaces", Proceedings of the Institution of Mechanical Engineers, Part C: Journal of Mechanical Engineering Science, 221(10):1181-1191, Oct. 1, 2007, 11 pages.
(Continued)

*Primary Examiner* — Laura A Auer
(74) *Attorney, Agent, or Firm* — Wilmer Cutler Pickering Hale and Dorr LLP

(57) ABSTRACT

The present disclosure describes a strategy to create self-healing, slippery liquid-infused porous surfaces. Roughened (e.g., porous) surfaces can be utilized to lock in place a lubricating fluid, referred to herein as Liquid B to repel a wide range of materials, referred to herein as Object A (Solid A or Liquid A). Slippery liquid-infused porous surfaces outperforms other conventional surfaces in its capability to repel various simple and complex liquids (water, hydrocarbons, crude oil and blood), maintain low-contact-angle hysteresis (<2.5°), quickly restore liquid-repellency after physical damage (within 0.1-1 s), resist ice, microorganisms and insects adhesion, and function at high pressures (up to at least 690 atm). Some exemplary application where slip-
(Continued)

pery liquid-infused porous surfaces will be useful include energy-efficient fluid handling and transportation, optical sensing, medicine, and as self-cleaning, and anti-fouling materials operating in extreme environments.

13 Claims, 68 Drawing Sheets

Related U.S. Application Data

No. 15/134,070, filed on Apr. 20, 2016, now Pat. No. 9,932,482, which is a continuation of application No. 13/980,856, filed as application No. PCT/US2012/021928 on Jan. 19, 2012, now Pat. No. 9,353,646.

(60) Provisional application No. 61/538,100, filed on Sep. 22, 2011, provisional application No. 61/529,734, filed on Aug. 31, 2011, provisional application No. 61/509,488, filed on Jul. 19, 2011, provisional application No. 61/496,883, filed on Jun. 14, 2011, provisional application No. 61/470,973, filed on Apr. 1, 2011, provisional application No. 61/466,352, filed on Mar. 22, 2011, provisional application No. 61/434,217, filed on Jan. 19, 2011.

(51) Int. Cl.

| | | |
|---|---|---|
| *C09D 5/16* | (2006.01) | |
| *A61L 27/28* | (2006.01) | |
| *A61L 15/24* | (2006.01) | |
| *A61L 15/34* | (2006.01) | |
| *A61L 15/42* | (2006.01) | |
| *A61L 15/46* | (2006.01) | |
| *A61L 27/34* | (2006.01) | |
| *A61L 27/50* | (2006.01) | |
| *A61L 33/00* | (2006.01) | |
| *A61L 33/06* | (2006.01) | |
| *B01L 3/00* | (2006.01) | |
| *B65D 25/14* | (2006.01) | |
| *H01L 31/0236* | (2006.01) | |
| *G02B 1/14* | (2015.01) | |
| *C10M 105/54* | (2006.01) | |
| *C10M 105/56* | (2006.01) | |
| *F01D 25/18* | (2006.01) | |
| *F15D 1/02* | (2006.01) | |
| *F15D 1/10* | (2006.01) | |
| *F28F 13/18* | (2006.01) | |
| *F28F 19/02* | (2006.01) | |
| *B05D 5/00* | (2006.01) | |
| *B01D 69/02* | (2006.01) | |
| *B05D 5/08* | (2006.01) | |
| *B63B 59/04* | (2006.01) | |
| *B64D 15/00* | (2006.01) | |
| *C02F 1/44* | (2006.01) | |
| *D06M 13/00* | (2006.01) | |
| *E04B 1/92* | (2006.01) | |
| *F01D 25/02* | (2006.01) | |
| *F16L 57/00* | (2006.01) | |
| *H01L 31/0216* | (2014.01) | |

(52) U.S. Cl.
CPC .............. *A61L 15/46* (2013.01); *A61L 27/28* (2013.01); *A61L 27/34* (2013.01); *A61L 27/50* (2013.01); *A61L 33/0094* (2013.01); *A61L 33/064* (2013.01); *B01L 3/5027* (2013.01); *B05D 3/002* (2013.01); *B05D 5/00* (2013.01); *B65D 25/14* (2013.01); *C09D 5/16* (2013.01); *C09D 5/1656* (2013.01); *C09D 5/1681* (2013.01); *C09D 5/1693* (2013.01); *C10M 105/54* (2013.01); *C10M 105/56* (2013.01); *F01D 25/18* (2013.01); *F15D 1/02* (2013.01); *F15D 1/10* (2013.01); *F28F 13/185* (2013.01); *F28F 19/02* (2013.01); *G02B 1/14* (2015.01); *H01L 31/0236* (2013.01); *A61L 2400/12* (2013.01); *B01D 69/02* (2013.01); *B01D 2325/06* (2013.01); *B01L 2300/16* (2013.01); *B05D 5/083* (2013.01); *B63B 59/04* (2013.01); *B64D 15/00* (2013.01); *C02F 1/44* (2013.01); *D06M 13/00* (2013.01); *E04B 1/92* (2013.01); *F01D 25/02* (2013.01); *F16L 57/00* (2013.01); *F28F 2245/04* (2013.01); *H01L 31/02167* (2013.01); *Y02W 10/37* (2015.05); *Y10T 428/24355* (2015.01); *Y10T 428/24364* (2015.01)

(56) References Cited

U.S. PATENT DOCUMENTS

| | | | |
|---|---|---|---|
| 4,386,170 A | 5/1983 | Monroe | |
| 4,633,004 A | 12/1986 | Boutevin et al. | |
| 4,787,991 A | 11/1988 | Morozumi et al. | |
| 4,861,511 A * | 8/1989 | Kaplan | C11D 3/3769 252/180 |
| 4,937,596 A | 6/1990 | Schmid | |
| 5,091,205 A | 2/1992 | Fan | |
| 5,358,719 A | 10/1994 | Mellul et al. | |
| 5,372,888 A | 12/1994 | Ogawa et al. | |
| 5,425,989 A | 6/1995 | Ogawa et al. | |
| 5,602,214 A | 2/1997 | Lin et al. | |
| 5,620,778 A | 4/1997 | Clatworthy | |
| 5,624,713 A | 4/1997 | Ramer | |
| 5,630,846 A | 5/1997 | Hara et al. | |
| 5,736,251 A | 4/1998 | Pinchuk | |
| 5,798,409 A | 8/1998 | Ho | |
| 5,804,318 A | 9/1998 | Pinchuk et al. | |
| 6,071,981 A | 6/2000 | Johnson et al. | |
| 6,171,673 B1 | 1/2001 | Tanaka et al. | |
| 6,232,379 B1 | 5/2001 | Takita | |
| 6,247,603 B1 | 6/2001 | Farrell et al. | |
| 6,447,919 B1 | 9/2002 | Brown et al. | |
| 6,511,753 B1 | 1/2003 | Teranishi et al. | |
| 7,189,934 B2 | 3/2007 | Youngner | |
| 7,192,993 B1 | 3/2007 | Sarangapani et al. | |
| 7,431,989 B2 | 10/2008 | Sakhrani et al. | |
| 7,560,492 B1 | 7/2009 | Claude et al. | |
| 7,666,514 B2 | 2/2010 | Sakamoto et al. | |
| 7,723,405 B2 | 5/2010 | Braun et al. | |
| 7,811,666 B2 | 10/2010 | Dry | |
| 7,877,968 B2 | 2/2011 | Kim et al. | |
| 2001/0014711 A1 | 8/2001 | Levy | |
| 2003/0212232 A1 | 11/2003 | Majeti et al. | |
| 2004/0034941 A1 | 2/2004 | Iwato et al. | |
| 2004/0186211 A1 | 9/2004 | Howell et al. | |
| 2005/0164008 A1 | 7/2005 | Rukavina | |
| 2006/0024504 A1 | 2/2006 | Nelson et al. | |
| 2006/0153993 A1 | 7/2006 | Schmidt et al. | |
| 2006/0159645 A1 | 7/2006 | Miller et al. | |
| 2006/0211802 A1 | 9/2006 | Asgari | |
| 2007/0039832 A1 | 2/2007 | Heikenfeld | |
| 2007/0141306 A1 | 6/2007 | Kasai et al. | |
| 2007/0154626 A1 | 7/2007 | Sasaki et al. | |
| 2007/0166344 A1 | 7/2007 | Qu et al. | |
| 2007/0184733 A1 | 8/2007 | Manley | |
| 2007/0224391 A1 | 9/2007 | Krupenkin et al. | |
| 2007/0254000 A1 | 11/2007 | Guo et al. | |
| 2008/0195170 A1 | 8/2008 | Asgari | |
| 2009/0078153 A1 | 3/2009 | Shchukin et al. | |
| 2009/0098299 A1 | 4/2009 | Cheng | |
| 2009/0209922 A1 | 8/2009 | Boisjoly | |
| 2010/0009583 A1 | 1/2010 | Bringley et al. | |
| 2010/0021748 A1 | 1/2010 | Hu et al. | |

(56) References Cited

U.S. PATENT DOCUMENTS

| | | | |
|---|---|---|---|
| 2010/0210745 A1 | 8/2010 | McDaniel et al. | |
| 2010/0285084 A1 | 11/2010 | Yang et al. | |
| 2011/0136653 A1 | 6/2011 | Koebel et al. | |
| 2011/0165206 A1 | 7/2011 | Liu et al. | |
| 2011/0283778 A1 | 11/2011 | Angelescu et al. | |
| 2011/0287987 A1 | 11/2011 | Mordukhovich et al. | |
| 2011/0305881 A1 | 12/2011 | Schultz et al. | |
| 2012/0004357 A1* | 1/2012 | Roulleaux | C09D 5/16 524/451 |
| 2012/0052241 A1 | 3/2012 | King et al. | |
| 2012/0141052 A1 | 6/2012 | Drew et al. | |
| 2012/0172787 A1 | 7/2012 | McClain et al. | |
| 2013/0032316 A1 | 2/2013 | Dhiman et al. | |
| 2013/0110222 A1 | 5/2013 | Slager | |

FOREIGN PATENT DOCUMENTS

| | | | |
|---|---|---|---|
| CN | 101052667 A | 10/2007 | |
| CN | 101198542 A | 6/2008 | |
| CN | 101374607 A | 2/2009 | |
| CN | 101444777 A | 6/2009 | |
| CN | 101538395 A | 9/2009 | |
| CN | 101580753 A | 11/2009 | |
| CN | 101675156 A | 3/2010 | |
| CN | 101918621 A | 12/2010 | |
| CN | 102388180 A | 3/2012 | |
| DE | 19818956 A1 | 11/1998 | |
| EP | 0166998 A2 | 1/1986 | |
| EP | 0338418 A1 | 10/1989 | |
| EP | 0497204 A2 | 8/1992 | |
| EP | 0893164 A2 | 1/1999 | |
| EP | 1002825 A2 | 5/2000 | |
| EP | 1487590 B1 | 12/2004 | |
| EP | 2228053 A1 | 9/2010 | |
| EP | 2363438 A1 | 9/2011 | |
| FR | 2943066 A1 * | 9/2010 | C09D 5/16 |
| JP | S60-259269 A | 12/1985 | |
| JP | 62-063219 A | 3/1987 | |
| JP | S62-252477 A | 11/1987 | |
| JP | 01-170932 A | 7/1989 | |
| JP | 04-270649 A | 9/1992 | |
| JP | 05-229402 A | 9/1993 | |
| JP | 5240251 B2 | 9/1993 | |
| JP | H06-180882 A | 6/1994 | |
| JP | H06-48685 U | 7/1994 | |
| JP | 07-242769 A | 9/1995 | |
| JP | H08-12816 A | 1/1996 | |
| JP | H10-183049 A | 7/1998 | |
| JP | H11-64772 A | 3/1999 | |
| JP | H11-345441 A | 12/1999 | |
| JP | 2000-510353 A | 8/2000 | |
| JP | 2001-131413 A | 5/2001 | |
| JP | 2003-170540 A | 6/2003 | |
| JP | 2004-037764 A | 2/2004 | |
| JP | 2004-136630 A | 5/2004 | |
| JP | 2005-082848 A | 3/2005 | |
| JP | 2005-231084 A | 9/2005 | |
| JP | 2006-280843 A | 10/2006 | |
| JP | 2008-223003 A | 9/2008 | |
| JP | 2009-523890 A | 6/2009 | |
| JP | 2010-047890 A | 3/2010 | |
| JP | 2010-167929 A | 8/2010 | |
| JP | 6228012 B2 | 11/2017 | |
| KR | 2009-0026199 A | 3/2009 | |
| WO | WO-92/10532 A1 | 6/1992 | |
| WO | WO-93/17077 A1 | 9/1993 | |
| WO | WO-99/36490 A1 | 7/1999 | |
| WO | WO-01/78800 A1 | 10/2001 | |
| WO | WO-02/09647 A2 | 2/2002 | |
| WO | WO-03013827 A1 | 2/2003 | |
| WO | WO-2005091309 A1 | 9/2005 | |
| WO | WO-2005/121288 A1 | 12/2005 | |
| WO | WO-2006/091235 A1 | 8/2006 | |
| WO | WO-2006/118460 A1 | 11/2006 | |
| WO | WO-2007/130734 A2 | 11/2007 | |
| WO | WO-2008/013825 A2 | 1/2008 | |
| WO | WO-2008/017472 A2 | 2/2008 | |
| WO | WO-2008/049108 A1 | 4/2008 | |
| WO | WO-2008/120505 A1 | 10/2008 | |
| WO | WO-2010028752 A1 | 3/2010 | |
| WO | WO-2010/042804 A2 | 4/2010 | |
| WO | WO-2010/065960 A2 | 6/2010 | |
| WO | WO-2010116045 A1 | 10/2010 | |
| WO | WO-2011005200 A1 | 1/2011 | |
| WO | WO-2011/049896 A2 | 4/2011 | |
| WO | WO-2012/055821 A1 | 5/2012 | |
| WO | WO-2012/055825 A1 | 5/2012 | |
| WO | WO-2012/100099 A2 | 7/2012 | |
| WO | WO-2012/100100 A2 | 7/2012 | |
| WO | WO-2013/022467 A2 | 2/2013 | |
| WO | WO-2013/106588 A1 | 7/2013 | |
| WO | WO-2013/115868 A2 | 8/2013 | |

OTHER PUBLICATIONS

Afessa, B. et al., "Association Between a Silver-Coated Endotracheal Tube and Reduced Mortality in Patients With Ventilator-Associated Pneumonia," Chest, vol. 137, pp. 1015-1021 (May 2010).

Ahuja, A. et al., "Nanonails: A Simple Geometrical Approach to Electrically Tunable Superlyophobic Surfaces," Langmuir, vol. 24, pp. 9-14 (2008).

Badrossamay, Mohammad Reza, et al., "Nanofiber Assembly by Rotary Jet-Spinning," Nano Letters, vol. 10, No. 6, pp. 2257-2261, 11 pages (Jun. 9, 2010).

Bai, Joseph R. et al., "Core-Annular Flows," Annual Review Fluid Mechanics, vol. 29, pp. 65-90 (Jan. 1997).

Banerjee, I. et al., "Antifouling coatings: recent developments in the design of surfaces that prevent fouling by proteins, bacteria, and marine organisms," Advanced Materials, pp. 690-718 (2011).

Banerjee, S. et al., "Infection control during GI endoscopy," Gastrointest. Endoscopy, vol. 67, pp. 781-790 (May 2008).

Banhart, John, "Manufacture, characterisation and application of cellular metals and metal foams," Progress in Materials Science, vol. 46, pp. 559-632 (2001).

Barstad, R. M. et al., "Monocyte procoagulant activity induced by adherence to an artificial surface is reduced by end-point immobilized heparin-coating of the surface", Thrombosis and Haemostasis, vol. 79, pp. 302-305, Downloaded from www.thrombosis-online.com on (Mar. 17, 2014).

Barthlott, W. & Neinhuis, C., "Purity of the sacred lotus, or escape from contamination in biological surfaces," Planta, vol. 202, pp. 1-8 (Apr. 1997).

Bauer, et al., "The Insect-Trapping Rim of Nepenthes Pitchers", Plant Signaling & Behavior, 4(11):1019-1023, Nov. 1, 2009.

Beilenhoff, U. et al., "ESGE-ESGENA guideline: Cleaning and disinfection in gastrointestinal endoscopy Update 2008," Endoscopy, vol. 40, pp. 939-957 (Sep. 23, 2008).

Berger, R. G., "Flavours and Fragrances: Chemistry, Bioprocessing and Sustainability," Springer, 15 pages—Title Page, Copyright Page and Table of Contents Only (2007).

Bhardwaj, U. et al., "A review of the development of a vehicle for localized and controlled drug delivery for implantable biosensors," J. Diabetes Sci. and Technol., vol. 2, pp. 1016-1029 (Nov. 2008).

Bico, J. et al., "Rough wetting," Europhysics Letters, vol. 55, No. 2, pp. 214-220 (Jul. 15, 2001).

Bico, J. et al., "Wetting of textured surfaces," Colloids and Surfaces, A: Physicochemical and Engineering Aspects, vol. 206, pp. 41-46 (2002).

Bocquet, L. & Lauga, E., "A smooth future?," Nature Mater., vol. 10, pp. 334-337 (May 2011).

Bohn, et al., "Insect Aquaplaning: *Nepenthes* Pitcher Plants Capture Prey with the Peristome, a Fully Wettable Water-Lubricated Anisotropic Surface," PNAS, 101(39):14138-14143, Sep. 28, 2004, 6 pages.

Bos, R. et al., "Retention of bacteria on a substratum surface with micro-patterned hydrophobicity," FEMS Microbiology Letters, vol. 189, No. 2, pp. 311-315 (Aug. 15, 2000).

(56) References Cited

OTHER PUBLICATIONS

Cassie, A.B.D. & Baxter, S., "Large contact angles of plant and animal surfaces," Nature, vol. 155, pp. 21-22 (Jan. 6, 1945).
Cassie, et al., "Wettability of Porous Surfaces", Transactions of the Faraday Society, vol. 40, pp. 546-551, Jan. 1944, 6 pages.
Chaudhury, Manoj K. and Whitesides, George M., "Direct Measurement of Interfacial Interactions between Semispherical Lenses and Flat Sheets of Poly(dimethylsiloxane) and Their Chemical Derivatives," Langmuir, vol. 7, pp. 1013-1025 (1991).
Chen, S. et al., "Surface hydration: Principles and applications toward low-fouling/nonfouling biomaterials," Polymer, vol. 51, pp. 5283-5293 (Aug. 10, 2010).
Chinese Office Action issued by the State Intellectual Property Office of the People's Republic of China for Application No. 201280012205.0 dated May 13, 2015 (20 pages).
Chinese Office Action issued by the State Intellectual Property Office of the People's Republic of China for Application No. 201280012210.1 dated May 21, 2015 (30 pages).
Clark, Jr., Leland C. and Gollan, Frank, "Survival of Mammals Breathing Organic Liquids Equilibrated With Oxygen at Atmospheric Pressure," Science, vol. 152, pp. 1755-1756 (Jun. 24, 1966).
Costerton, J. et al., "Bacterial biofilms: a common cause of persistent infections," Science, vol. 284, No. 5418, pp. 1318-1322 (May 21, 1999).
Costerton, J.W. et al., "Bacterial biofilms in nature and disease," Ann. Rev. Microbiol., vol. 41, pp. 435-464 (1987).
Cribier, A. et al., "Percutaneous Transcatheter Implantation of an Aortic Valve Prosthesis for Calcific Aortic Stenosis," Circulation, vol. 106, pp. 3006-3008 (Nov. 25, 2002).
Crnich, C.J. & Maki, D.G., "The Promise of Novel Technology for the Prevention of Intravascular Device-Related Bloodstream Infection. I. Pathogenesis and Short-Term Devices," Clinical Infectious Diseases, vol. 34, pp. 1232-1242 (May 1, 2002).
Database WPI Weekly 198933, Thomson Scientific, London, GB, AN 1989-237086, XP002694116 & JP1170932A (Nippon Sheet Glass Co. Ltd.) 1 page (Jul. 6, 1989) (abstract).
De Beer, D. & Stoodley, P., "Microbial Biofilms," Prokaryotes, vol. 1, pp. 904-937 (2006).
De Gennes, P.-G. et al., "Capillarity and Wetting Phenomena: drops, bubbles, pearls, waves," Springer, New York, 151 pages (No Month Listed 2004).
Dieter, R.S., "Coronary artery stent infection," Clin. Cardiol., vol. 23, pp. 808-810 (Jan. 6, 2000).
Dismukes et al., "Prosthetic valve endocarditis: Analysis of 38 cases," Circulation, vol. 48, pp. 365-377 (Aug. 1973).
Drelich, et al., "Measurement of Interfacial Tension in Fluid-Fluid Systems", Encyclopedia of Surface and Colloid Science, pp. 3152-3166 (Jan. 2002).
Fadeev, A. Y. and McCarthy, T. J., "Surface Modification of Poly(ethylene terephthalate) to Prepare Surfaces with Silica-Like Reactivity," Langmuir, vol. 14, No. 19, pp. 5586-5593 (1998).
Fowkes, F.M., "Attractive forces at interfaces," Ind. Eng. Chem., vol. 56, pp. 40-52 (Dec. 1964).
Fuerstman, et al., "Coding/Decoding and Reversibility of droplet trains in Microfluidic networks," Science, vol. 315, No. 5813, pp. 828-832 (Feb. 9, 2007).
Gao, L. and McCarthy, T.J., "Teflon is Hydrophilic. Comments on Definitions of Hydrophobic, Shear versus Tensile Hydrophobicity, and Wettability Characterization," Langmuir, vol. 24, pp. 9183-9188 (Sep. 2, 2008).
Garg, N. et al., "Acute Coronary Syndrome Caused by Coronary Artery Mycotic Aneurysm Due to Late Stent Infection Localized With Radiolabeled Autologous Leukocyte Imaging," Clin. Nucl. Med., vol. 34, pp. 753-755 (Nov. 2009).
George, P.A. et al., "Self-assembling polystyrene-block-poly(ethylene oxide) copolymer surface coatings: resistance to protein and cell adhesion," Biomaterials, vol. 30, pp. 2449-2456 (May 2009).

Gristina, A.G. et al., "Biomaterial-centered sepsis and the total artifical heart. Microbial adhesion vs tissue integration," JAMA, vol. 259, pp. 870-874 (Feb. 1988).
Hall-Stoodley, L. et al., "Bacterial biofilms: from the natural environment to infectious diseases," Nature Reviews Microbiology, vol. 2, No. 2, pp. 95-108 (Feb. 2004).
Hatton, et al., "Assembly of large-area, highly ordered, crack-free inverse opal films," Proceedings of the National Academy of Science of the United States of America, vol. 107, No. 23, pp. 10354-10359 (Jun. 8, 2010).
Hearn, A.T. et al., "Endovascular stent infection with delayed bacterial challenge," American Journal of Surgery, vol. 174, pp. 157-159 (Aug. 1997).
Hejazi, et al., "Wetting Transitions in Two-, Three-, and Four-Phase Systems," Langmuir, vol. 28, pp. 2173-2180, (2012).
Hozumi et al., "Hydrophobization of Metal/Metal Oxide Surfaces Using Monolayer Films", Journal of the Surface Finishing Society of Japan, Oct. 9, 2009, vol. 60, No. 1, pp. 16-20. English translation.
Inazaki, S. et al., "Surface modification of polytetrafluoroethylene with ArF excimer laser irradiation," J. Photopoly. Sci. Technol. vol. 7, No. 2, pp. 389-396 (1994).
International Search Report and Written Opinion issued by the European Patent Office as International Searching Authority for International Application No. PCT/US2012/021929, dated Aug. 21, 2012 (23 pages).
International Search Report and Written Opinion issued by the European Patent Office as International Searching Authority for International Application No. PCT/US2013/021056 dated Jun. 6, 2013 (21 pages).
International Search Report and Written Opinion issued by the European Patent Office as International Searching Authority for International Application No. PCT/US2013/050403 dated Dec. 4, 2013 (21 pages).
International Search Report and Written Opinion issued by the International Searching Authority for International Application No. PCT/US14/25935 dated Jan. 23, 2015 (11 pages).
International Search Report and Written Opinion issued by the International Searching Authority for International Application No. PCT/US2013/050406 dated Nov. 20, 2013 (20 pages).
International Search Report and Written Opinion Issued by the U.S. Patent and Trademark Office as International Searching Authority for International Application No. PCT/US09/48880 dated Nov. 17, 2009 (14 pages).
International Search Report and Written Opinion Issued by the U.S. Patent and Trademark Office as International Searching Authority for International Application No. PCT/US11/44553 dated Oct. 31, 2011 (12 pages).
International Search Report issued by the European Patent Office as International Searching Authority for International Application No. PCT/US2012/021928, dated Aug. 10, 2012, 6 pages.
Ishino, et al., "Wicking Within Forests of Micropillars", EPL Journal, vol. 79, pp. 56005-p1-56005-p5, Sep. 2007, 5 pages.
Israelachvili, Jacob N., "Intermolecular and Surface Forces—Third Edition," Academic Press, 706 pages (2011).
Japanese Decision of Rejection mailed on Nov. 28, 2017, in Japanese Application No. 2014-552304, translation and original, 10 pages.
Karchmer, A.W. et al., "*Staphylococcus epidermidis* causing prosthetic valve endocarditis: microbiologic and clinical observations as guides to therapy," Ann. Intern. Med., vol. 98, pp. 447-455, (Apr. 1, 1983).
Keck et al., "Preparation of partially fluorinated aryl/alkyl vinylene ether polymers," Polymer International, vol. 62, Issue 10, pp. 1485-1491, Oct. 2013.
Khoo, X. et al., "Directed assembly of PEGylated-peptide coatings for infection-resistant titanium metal," J. Am. Chem. Soc., vol. 131, pp. 10992-10997 (2009).
Kim, et al., "Structural Transformation by Electrodeposition on Patterned Substrates (STEPS): A new Versatile Nanofabrication Method," Nano Letters, vol. 12, No. 2, pp. A-G (Mar. 2011).
Kobayashi, H. and Owen, M.J., "Surface tension of poly[(3,3,4,4,5,5,6,6,6-nonaflurohexyl) methylsiloxane]," Macromolecules, vol. 23, No. 23, pp. 4929-4933 (1990).

(56) References Cited

OTHER PUBLICATIONS

Koschwanez, H.E. et al., "In vitro and in vivo characterization of porous poly-L-lactic acid coatings for subcutaneously implanted glucose sensors," Journal of Biomedical Materials Research Part A, pp. 792-807 (Dec. 2008).
Lee, Woo, et al., "Fast fabrication of long-range ordered porous alumina membranes by hard anodization," Nature Mater., vol. 5, pp. 741-747 (Sep. 2006).
Li, Yang, et al., "Bioinspired Self-Healing Superhydrophobic Coatings," Angewandte Chemie, vol. 49, No. 35, pp. 6129-6133 (Aug. 16, 2010).
Lillehoj, et al., "A self-pumping lab-on-a-chip for rapid detection of botulinum toxin," Lab Chip, vol. 10, pp. 2265-2270 (Jun. 11, 2010).
Lin, T-K, et al., "Surface modification of polytetrafluoroethylene films by plasma pretreatment and graft copolymerization to improve their adhesion to bismaleimide," Polym. Int., vol. 58, No. 1, pp. 46-53 (Jan. 2009).
Liu et al., "Organogel-based Thin Films for Self-Cleaning on Various Surfaces," Advanced Materials, 5 pages, (2013).
Matsunaga, Mariko, et al., "Controlling the Stability and Reversibility of Micropillar Assembly by Surface Chemistry," J. Am. Chem. Soc., vol. 133, No. 14, pp. 5545-5553, 4 pages (Dec. 2, 2011).
Meuler, Adam J. et al., "Relationships between Water Wettability and Ice Adhesion," ACS Applied Materials and Interfaces, vol. 2, No. 11, 31 pages (Oct. 15, 2010).
MicroSurfaces, Inc., "Anti-Stiction Coatings in MEMS Devices," MicroSurfaces, Inc., retreived from website URL: http://memsurface.com/stiction.html, 2 pages (retrieved on Dec. 8, 2011).
Miller-Chou et al., "A review of polymer dissolution," Progress in Polymer Science, vol. 28, pp. 1223-1270, (2003).
Munro, W.A. et al., "Deterioration of pH electrode response due to biofilm formation on the glass membrane," Sensors and Actuators B-Chem, vol. 37, pp. 187-194 (Dec. 1996).
Nguyen, et al., "Quantitative Testing of Robustness on Superomniphobic Surfaces by Drop Impact", Langmuir, 26(23):18369-18373, Dec. 7, 2010, 5 pages.
Niimi, Y. et al., "The effects of heparin coating of oxygenator fibers on platelet adhesion and protein adsorption," Anesth. Analg., vol. 89, pp. 573-579 (May 12, 1999).
Noetzel, M.J. & Baker, R.P., "Shunt fluid examination: risks and benefits in the evaluation of shunt malfunction and infection," J. Neurosurg., vol. 61, pp. 328-332 (Aug. 1984).
Nosonovsky, "Multiscale Roughness and Stability of Superhydrophobic Biomimetic Interfaces", Langmuir, 23(6):3157-3161, Feb. 13, 2007, 5 pages.
Nosonovsky, et al., "Biomimetic Superhydrophobic Surfaces: Multiscale Approach", Nano Letters, vol. 7, No. 9, pp. 2633-2637, Aug. 17, 2007.
O'Toole, G., et al., "Biofilm Formation as Microbial Development," Annu. Rev. Microbiol., vol. 54, pp. 49-79, 35 pages (2000).
Park, K.D. et al., "Bacterial adhesion on PEG modified polyurethane surfaces," Biomaterials, vol. 19, No. 7-9, pp. 851-859 (Apr.-May 1998).
Poetes, et al., "Metastable Underwater Superhydrophobicity," Physical Review Letters, vol. 105, Issue 16, pp. 166104.1-166104.4 Published (Oct. 14, 2010).
Pokroy, B. et al., "Fabrication of BioInspired Actuated Nanostructures with Arbitrary Geometry and Stiffness," Adv. Mater., vol. 21, pp. 463-469 (Jan. 26, 2009).
Prakash and Gershenfeld, "Microfluidic Bubble Logic," Science, vol. 315, No. 5813, 5 pages (Feb. 9, 2007).
Prime, K.L. & Whitesides, G.M., "Self-assembled organic monolayers: model systems for studying adsorption of proteins at surfaces," Science, vol. 252, No. 5009, p. 1164-1167 (May 24, 1991).
Quere, D., "Wetting and roughness," Annu. Rev. Mater. Res., vol. 38, pp. 71-99 (Apr. 7, 2008).
Raza, et al., "Superhydrophobic Surfaces by Anomalous Fluoroalkylsilane Self-Assembly on Silica Nanosphere Arrays", Langmuir, 26(15):12962-12972, Aug. 3, 2010, 11 pages.
Rothemund, Paul W.K., "Folding DNA to create nanoscale shapes and patterns," Nature, vol. 440, 82 pages (Mar. 16, 2006).
Rothemund, Paul W.K., "Folding DNA to create nanoscale shapes and patterns," Nature, vol. 440, pp. 297-302, Mar. 16, 2006.
Rowe, David J., "Chemistry and Technology of Flavors and Fragrances," Blackwell Publishing Ltd, 12 pages—Title page, Copyright page and Table of Contents Only (2005).
Saido et al., "A Growth of Aspergillus Niger on Surface of Polymer Films was Observed by FT-IR and Scanning Electron Microscope", Materials Life, Oct. 8, 1991, vol. 3 No. 4, pp. 218-224. English translation.
Shaffer, T.H. et al., "Liquid Ventilation," Pediatric Pulmonology, vol. 14, pp. 102-109 (Oct. 1992).
Shaffer, T.H. et al., "State of the Art Review: Liquid Ventilation," Pediatric Pulmonology, vol. 14, pp. 102-109 (Oct. 1992).
Shafrin, E.G. & Zisman, W.A., "Constitutive relations in the wetting of low energy surfaces and the theory of the retraction method of preparing monolayers," J. Phys. Chem., vol. 64, pp. 519-524 (May 1960).
Skattum, L. et al., "Complement deficiency states and associated infections," Mol. Immunol., vol. 48, No. 14, pp. 1643-1655 (Aug. 2011).
Sohail, M.R. et al., "Risk factor analysis of permanent pacemaker infection," Clin. Infect. Dis., vol. 45, pp. 166-173 (Jul. 15, 2007).
Stober, W. and Fink, A., "Controlled growth of monodisperse silica spheres in the micron size range," Journal of Colloid and Interface Science, vol. 26, No. 1, pp. 62-69 (Jan. 1968).
Trevors, J.T., "Silver resistance and accumulation in bacteria," Enzyme and Microbial Technology, vol. 9, No. 6, pp. 331-333 (Jun. 1987).
Tuli, S. et al., "Risk factors for repeated cerebrospinal shunt failures in pediatric patients with hydrocephalus," J. Neurosurg., vol. 92, pp. 31-38 (Jan. 2000).
Tuteja, Anish, et al., "Designing Superoleophobic Surfaces," Science, vol. 318, No. 5856, pp. 1618-1622 (Dec. 7, 2007) www.sciencemag.org.
Tuteja, Anish, et al., "Robust omniphobic surfaces," PNAS, vol. 105, No. 47, pp. 18200-18205 (Nov. 25, 2008).
Varanasi, Kripa K. et al., "Frost formation and ice adhesion on superhydrophobic surfaces," Applied Physics Letters, vol. 97, pp. 234102-1-234102-3 (2010).
Vogel et al., "A Convenient Method to Produce Close- and Non-close-Packed Monolayers using Direct Assembly at the Air-Water Interface and Subsequent Plasma-Induced Size Reduction," Macromolecular Chemistry and Physics, vol. 212, pp. 1719-1734 (2011).
Vogel et al., "From soft to hard: the generation of functional and complex colloidal monolayers for nanolithography," Soft Matter, vol. 8, pp. 4044-4061 (2012).
Vogel et al., "Wafer-Scale Fabrication of Ordered Binary Colloidal Monolayers with Adjustable Stoichiometries," Advanced Functional Materials, vol. 21, pp. 3064-3073, (2011).
Voskerician, G. et al., "Biocompatibility and biofouling of MEMS drug delivery devices," Biomaterials, vol. 24, pp. 1959-1967 (2003).
Wasserscheid, P. and Welton, T., "Ionic Liquids in Synthesis," Wiley-VCH Verlag GmbH & Co., 380 pages (2002).
Wenzel, "Resistance of Solid Surfaces to Wetting by Water", Industrial and Engineering Chemistry, 28(8):988-994, Aug. 1936, 7 pages.
Williams, Kirt R., et al., "Etch Rates for Micromachining Processing-Part II," Journal of Microelectromechanical Systems, vol. 12, No. 6, pp. 761-778 (Dec. 2003).
Wilson, G.S. & Gifford, R., "Biosensors for real-time in vivo measurements," Biosens. Bioelectron., vol. 20, pp. 2388-2403 (Jan. 15, 2005).
Wong, P.K. et al., "Deformation of DNA molecules by hydrodynamic focusing," Journal of Fluid Mechanics, vol. 497, pp. 55-65 (2003).
Wong, Pak Kin, et al., "Closed-loop control of cellular functions using combinatory drugs guided by a stochastic search algorithm,"

(56) References Cited

OTHER PUBLICATIONS

Proceedings of National Academy of Science for the United States of America, vol. 105, No. 13, pp. 5105-5110 (Apr. 1, 2008).
Wong, T. S. et al., "Bioinspired self-repairing slippery surfaces with pressure-stable omniphobicity," Nature, vol. 477, No. 7365, pp. 443-447 (Sep. 22, 2011).
Wool, "Self-Healing Materials: A Review", Soft Matter, 4:400-418, Advance Article published online, Jan. 10, 2008, 19 pages.
Xu, Q. et al., "Approaching Zero: Using Fractured Crystals in Metrology for Replica Molding," J. Am. Chem. Soc., vol. 127, No. 3, pp. 854-855 (2005).
Zhao, L. et al., "Antibacterial coatings on Titanium Implants," Journal of Biomedical Materials Research Part B: Applied Biomaterials, vol. 91, No. 1, pp. 470-480 (2009).
Zhu et al., "Ice-phobic Coatings Based on Silicon-Oil-Infused Polydimethylsiloxane," American Chemical Society Applied Materials & Interfaces, vol. 5, pp. 4053-4062, (2013).
Shi et al., "Microstructure and friction properties of PVA/PVP hydrogels for articular cartilage repair as function of polymerization degree and polymer concentration," Wear, Jul. 30, 2013, vol. 305, pp. 280-285.
Akamatsu, "Water-repellent Coating on Glass," New Glass, Sep. 2006, vol. 21, No. 3, pp. 27-34. Full English translation with original. ISSN 0914-6563. (<https://www.newglass.jp/mag/TITL/maghtml/82e.html>).
Mori, "Silicone Surface Treatment," Journal of the Society of Rubber Industry of Japan (Nihon Gomu Kyokai shi), 1986, vol. 59, Issue 11, pp. 627-633. Issn: 0029-022X. Released Jul. 9, 2007. Full English translation with original. (<https://www.jstage.jst.go.jp/article/gomu1944/59/11 /59_11_627/_article/-char/en>).
Nakao, "Silicone Water Repellents," Journal of Synthetic Organic Chemistry, Japan, Jul. 1966, vol. 24, No. 7, pp. 598-608. Full English translation with original. ISSN 0037-9980. (<https://www.jstage.jst.go.jP/article/yukigoseikyokaishi1943/24/7/24_7_598/_article/-char/en>).

* cited by examiner a. Exposed to Medium X b. Pipe Flow

- Liquid A (Immiscible Test Fluid)
- Liquid B (Lubricant)
- Functionalized Porous/Textured Solid
- Medium X, where X = air/water/other immiscible fluids FIG. 11A  FIG. 11B  FIG. 11C
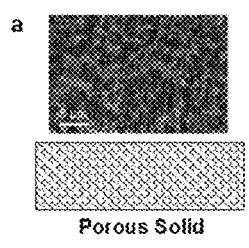
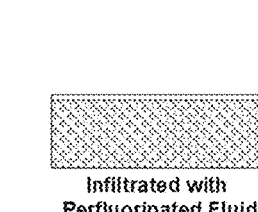
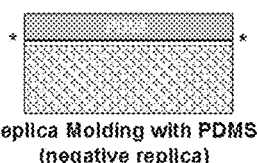
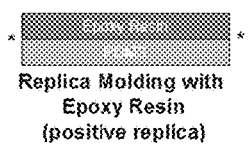
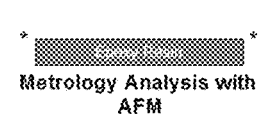
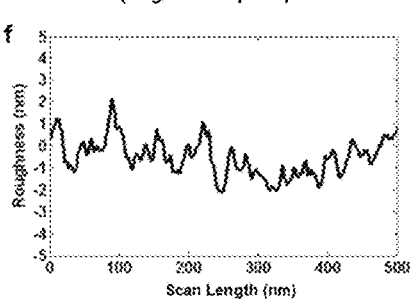
FIG. 11D  FIG. 11E  FIG. 11F

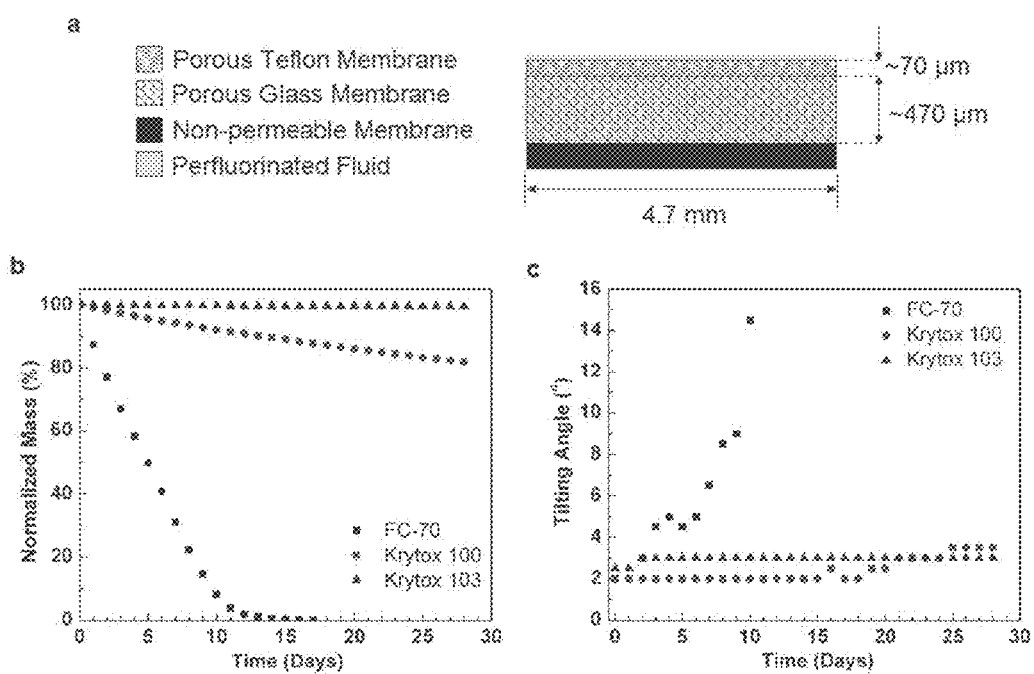

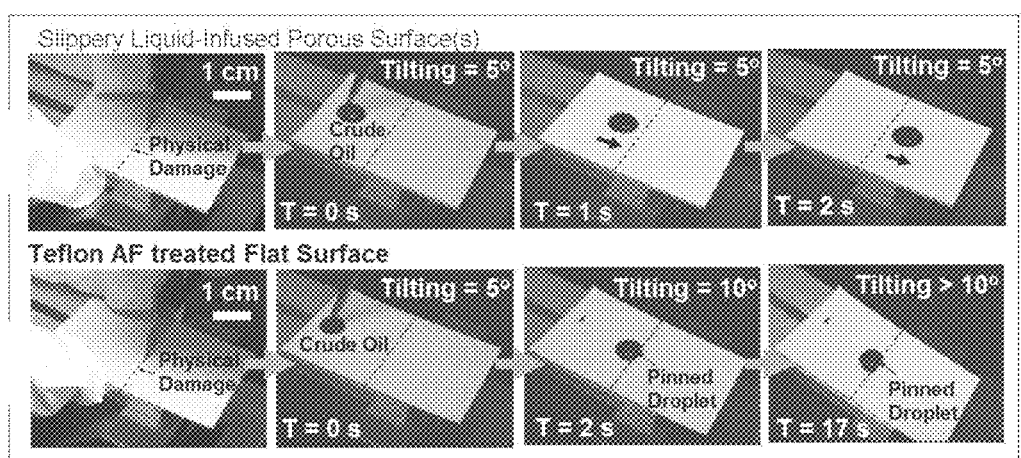

A. Liquid-slippery Surface  B. Nanostructured Surface

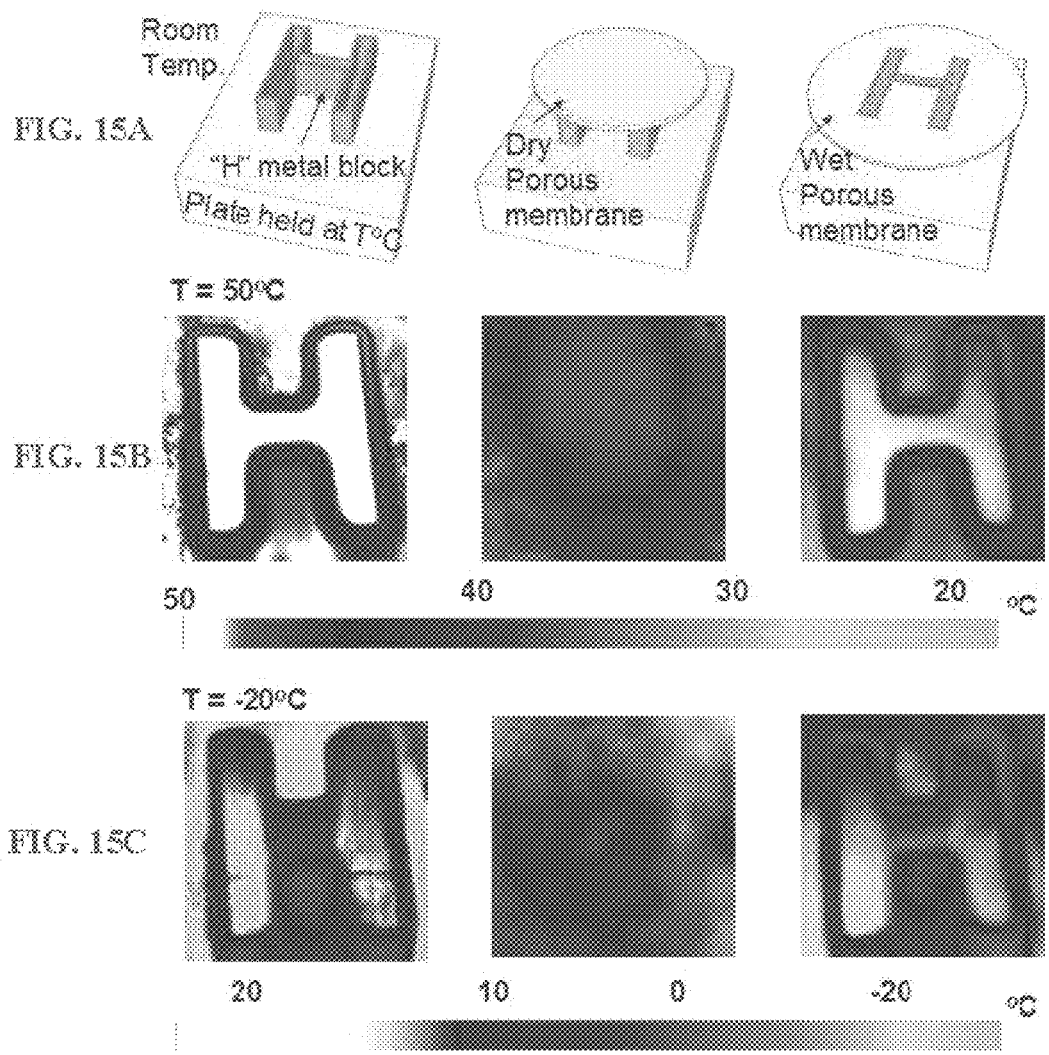

FIG. 17A    FIG. 17B    FIG. 17C
1. Liquid-Slippery Surface (Left, L-S) vs Flat Surface (Right, FLAT)
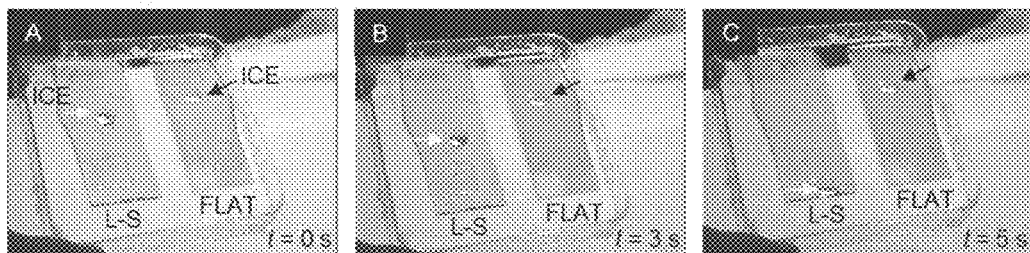
2. Liquid-Slippery Surface (Left, L-S) vs Nanostructured Surface (Right, N-S)
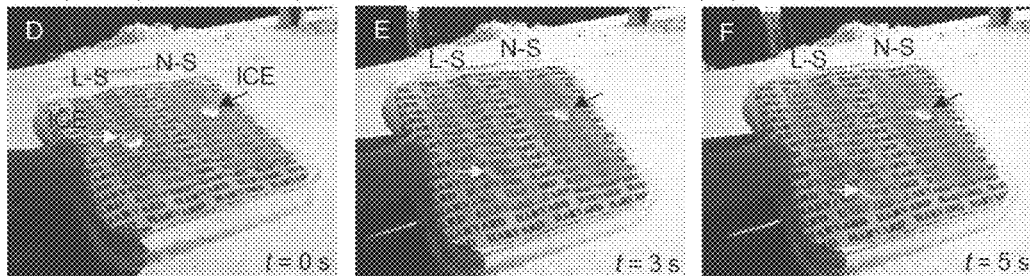
FIG. 17D    FIG. 17E    FIG. 17F 1. Liquid-Slippery Surface (L-S)
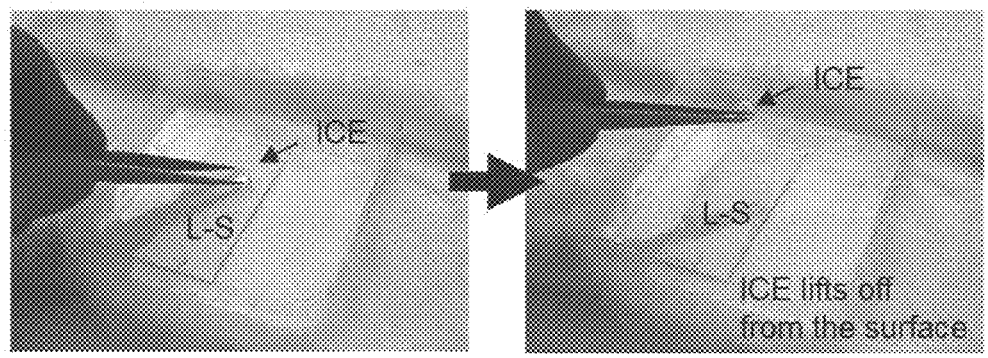
2. Nanostructured Surface (N-S)
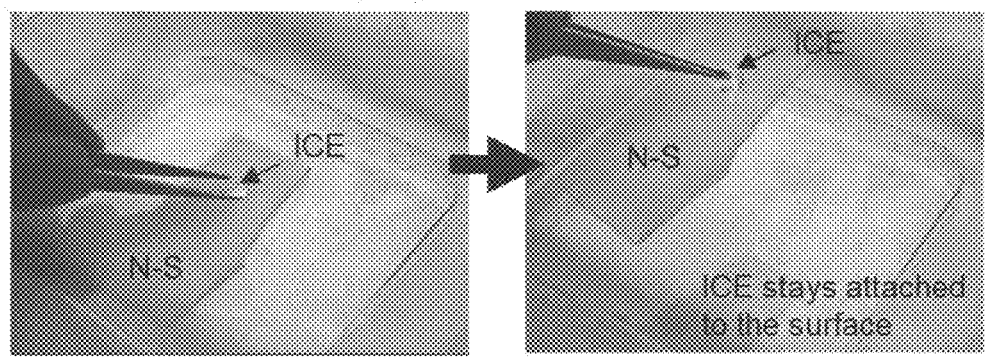
FIG. 18

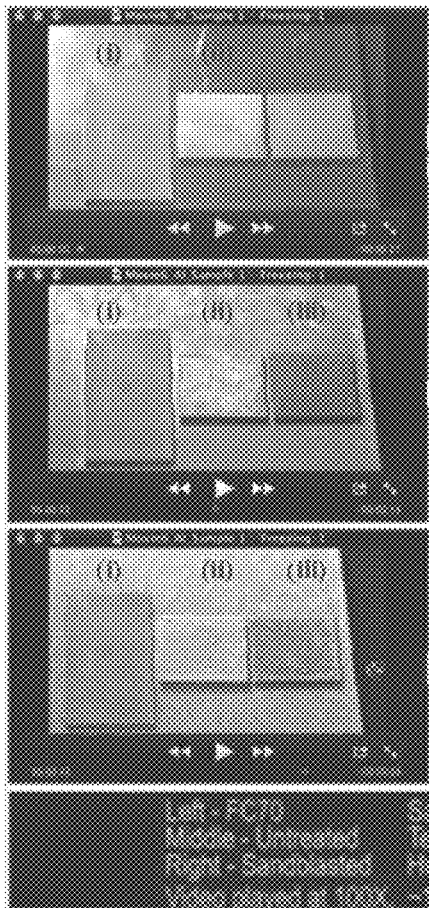
FIG. 29A
FIG. 29C
FIG. 29E
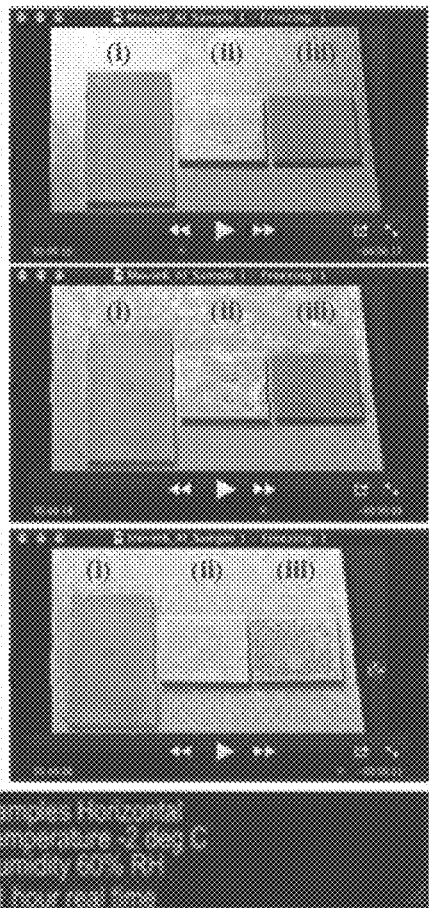
FIG. 29B
FIG. 29D
FIG. 29F

SANITATION SYSTEMS AND COMPONENTS THEREOF HAVING A SLIPPERY SURFACE

RELATED APPLICATIONS

This application is a continuation application of U.S. patent application Ser. No. 15/804,809, filed Nov. 6, 2017, which is a continuation application of U.S. patent application Ser. No. 15/134,070, filed Apr. 20, 2016, which is a continuation of U.S. patent application Ser. No. 13/980,856, filed Feb. 11, 2014, now U.S. Pat. No. 9,353,646, which is a national stage application of International Application No. PCT/US12/21928, filed Jan. 19, 2012, which claims priority to U.S. Provisional Patent Application No. 61/434,217, filed on Jan. 19, 2011; U.S. Provisional Patent Application No. 61/466,352, filed on Mar. 22, 2011; U.S. Provisional Patent Application No. 61/470,973, filed on Apr. 1, 2011; U.S. Provisional Patent Application No. 61/496,883, filed on Jun. 14, 2011; U.S. Provisional Patent Application No. 61/509,488, filed on Jul. 19, 2011; U.S. Provisional Patent Application No. 61/529,734 filed on Aug. 31, 2011; U.S. Provisional Patent Application No. 61/538,100, filed on Sep. 22, 2011, the contents of which are incorporated by reference herein in their entireties.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present disclosure relates generally to slippery surfaces, methods for forming them, and their uses.

BACKGROUND

Current development of liquid-repellent surfaces is inspired by the self-cleaning abilities of many natural surfaces on animals, insects, and plants. Water droplets on these natural surfaces roll off or slide off easily, carrying the dirt or insects away with them. The presence of the micro/nanostructures on many of these natural surfaces has been attributed to the water-repellency function. These observations have led to enormous interests in manufacturing biomimetic water-repellent surfaces in the past decade, owing to their broad spectrum of potential applications, ranging from water-repellent fabrics to friction-reduction surfaces.

SUMMARY

In one aspect, an article having a repellant surface, includes a substrate having a roughened surface; and a lubricating liquid wetting and adhering to the roughened surface to form a stabilized liquid overlayer, wherein the liquid covers the roughened surface at a thickness sufficient to form a liquid upper surface above the roughened surface, wherein the roughened surface and the lubricating liquid have an affinity for each other such that the lubricating liquid is substantially immobilized on the substrate to form a repellant surface.

In one or more embodiments, the article is capable of repelling a foreign material, or the article is capable of reducing the adhesion of the foreign material to the repellant surface.

In one or more embodiments, the lubricating liquid is selected to be chemically inert to the foreign material.

In one or more embodiments the affinity of the roughened surface for the lubricating liquid is great than the affinity of the roughened surface for the foreign material.

In any preceding embodiments, the foreign material is a fluid or a solid.

In any preceding embodiments, the roughened surface comprises raised features having at least one dimension of the scale of nanometers to micrometers.

In any preceding embodiments, the substrate comprises a porous material.

In any preceding embodiments, the optical refractive indices of the substrate and the lubricating liquid are substantially similar.

In any preceding embodiments, the substrate comprises a polymer, metal, sapphire, glass, carbon in different form, or ceramic.

In any preceding embodiments, roughened surface comprises fibers, particles, electrochemically deposited polymer a sand blasted surface, or a wet or dry etched surface.

In any preceding embodiments, roughened surface comprises a chemical functionalizing layer, and for example, the chemical functionalizing layer comprises a fluorinated compound such as a perfluorocarbon oil In any preceding embodiments, the lubricating liquid is a hydrophobic oil.

In any preceding embodiments, the article satisfies the following condition $$\gamma_{BX} \cos \theta_{BX} - \gamma_{AX} \cos \theta_{AX} > 0 \tag{e1}$$

wherein $\gamma_{AX}$ is the interfacial energies of the foreign agent with a surrounding medium; wherein $\gamma_{BX}$ is the interfacial energies of the lubricating liquid with the surrounding medium; wherein $\theta_{AX}$ is the equilibrium contact angle of the foreign material on a flat solid surface immersed under the surrounding medium; and wherein $\theta_{BX}$ is the equilibrium contact angle of the liquid of the lubricating liquid on a flat solid surface immersed under the surrounding medium.

In any preceding embodiments, the article satisfies the following two conditions when the article is exposed to Medium X, where X is air/gas/water/immiscible fluid:

$$R(\gamma_{BX} \cos \theta_{BX} - \gamma_{AX} \cos \theta_{AX}) - \gamma_{AB} > 0 \tag{e2}$$

$$R(\gamma_{BX} \cos \theta_{BX} - \gamma_{AX} \cos \theta_{AX}) + \gamma_{AX} - \gamma_{BX} > 0 \tag{e3}$$

wherein $\gamma_{AX}$ is the interfacial energies of the foreign agent with a surrounding medium; wherein $\gamma_{BX}$ is the interfacial energies of the lubricating liquid with the surrounding medium; wherein $\gamma_{AB}$ is the interfacial energies of the foreign material and the lubricating liquid interface; wherein $\theta_{AX}$ is the equilibrium contact angle of the foreign material on a flat solid surface immersed under the surrounding medium; wherein $\theta_{BX}$ is the equilibrium contact angle of the lubricating liquid on a flat solid surface immersed under the surrounding medium; and R is the roughness factor of the roughened surface.

In any preceding embodiments the article maintains its properties when in contact with the foreign material at pressures in excess of 5000 Pa, or the article maintains its properties when in contact with the foreign material at pressures in excess of $10^6$ Pa.

In any preceding embodiments, the article is capable of self-cleaning or the article is capable of self-healing.

In any preceding embodiments, the article further comprises a reservoir comprising an amount of lubricating liquid in fluid communication with the lubricating layer.

In any preceding embodiments, the porous material includes a solid substrate that is selected to have one or more of the following properties: electrical conductive, non-conductive, magnetic, non-magnetic, elastic, non-elastic, light-sensitive, non-light-sensitive, temperature-sensitive, or non-temperature sensitive.

In any preceding embodiments, the substrate is a flat substrate, a round substrate, a cylindrical substrate, or a geometrically complex substrate.

In another aspect, a flow channel, an optical component, a sign or commercial graphic, a building material, an element of a refrigeration system where preventing or reducing accumulation of ice, frost or condensate is advantageous, like coil, pipe, fin, cartridge of fins or wall, or heat exchanger are provided having a slippery, repellant and/or no-adhesive surface according to any of the preceding embodiments.

In another aspect, a device having at least one surface exposed to wind or water resistance, wherein the device is selected from the group consisting of a wind mill, a container, a solar cell, and avionic device, a marine vessel, roofing material, a fabric, a fingerprint resistant surface, for example contained in a lens, goggle, a touch screen, or a window, and an underwater device are provided having a slippery, repellant and/or no-adhesive surface according to any of the preceding embodiments.

In another aspect, a fluid transport device is provided having at least a portion of a fluid contacting surface having a slippery, repellant and/or no-adhesive surface according to any of the preceding embodiments.

In another aspect, a method for producing a slippery surface for repelling a foreign material or reduction adhesion of a foreign material is provided. The method includes providing a roughened surface; and introducing a lubricating liquid to wet and adhere said lubricating liquid to the roughened surface to form an over-coated layer, wherein the roughened surface and the lubricating liquid have an affinity for each other such that the lubricating liquid is substantially immobilized on the substrate to form a repellant surface.

In one embodiment, the substrate comprises a porous material.

In any preceding embodiment, the foreign material is a fluid or a solid.

In any preceding embodiment, said providing and introducing are carried out to satisfy the following condition $$\gamma_{BX} \cos \theta_{BX} - \gamma_{AX} \cos \theta_{AX} > 0 \quad (e1)$$

wherein $\gamma_{AX}$ is the interfacial energies of the foreign agent with a surrounding medium; wherein $\gamma_{BX}$ is the interfacial energies of the lubricating liquid with the surrounding medium; wherein $\theta_{AX}$ is the equilibrium contact angle of the foreign material on a flat solid surface immersed under the surrounding medium; and wherein $\theta_{BX}$ is the equilibrium contact angle of the liquid of the lubricating liquid on a flat solid surface immersed under the surrounding medium.

In any preceding embodiment, said providing and introducing are carried out to satisfy the following two conditions when the slippery surface is exposed to Medium X, where X is air/gas/water/immiscible fluid:

$$R(\gamma_{BX} \cos \theta_{BX} - \gamma_{AX} \cos \theta_{AX}) - \gamma_{AB} > 0 \quad (e2)$$

$$R(\gamma_{BX} \cos \theta_{BX} - \gamma_{AX} \cos \theta_{AX}) + \gamma_{AX} - \gamma_{BX} > 0 \quad (e3)$$

wherein $\gamma_{AX}$ is the interfacial energies of the foreign agent with a surrounding medium; wherein $\gamma_{BX}$ is the interfacial energies of the lubricating liquid with the surrounding medium; wherein $\gamma_{AB}$ is the interfacial energies of the foreign material and the lubricating liquid interface; wherein $\theta_{AX}$ is the equilibrium contact angle of the foreign material on a flat solid surface immersed under the surrounding medium; wherein $\theta_{BX}$ is the equilibrium contact angle of the lubricating liquid on a flat solid surface immersed under the surrounding medium; and R is the roughness factor of the roughened surface.

In any preceding embodiment, further comprising providing a reservoir comprising an amount of lubricating liquid.

In any preceding embodiment, the slippery surface is formed over a flat substrate, a round substrate, a cylindrical substrate, or a geometrically complex substrate.

In any preceding embodiment, the roughened surface is provided on a surface of a flow channel, on a surface of an optical component, on a surface of a sign or a commercial graphic, on a surface of a building material, on a surface of a cooling element, on a surface of a heat exchanger, on a surface of a wind mill, on a surface of a turbine, on a surface of a solar cell on a surface of an avionic device, d on a surface of a marine vessel, or on a surface of an underwater device, on a surface of a fabric.

In another aspect, a method of transporting a fluid under pressurized condition is described including providing a flow path with a roughened surface and a lubricating liquid that wets and adheres to the roughened surface to form an over-coated layer; and sending a fluid along said flow path; wherein the roughened surface has a greater affinity towards the lubricating liquid as compared to the fluid; and wherein the lubricating liquid and the fluid are substantially chemically inert with each other.

In one or more embodiments, the flow path is a microfluidic channel, or pipe.

In any preceding embodiment, the fluid is a non-polar fluid, polar fluid, or combinations thereof, or water, oil, or other complex fluids.

In any preceding embodiment, further comprising providing additional lubricating liquid to replenish any loss of the lubricating liquid during operation.

In another aspect, a method of improving a defrosting cycle of a cooling system includes providing a cooling element with a roughened surface and a lubricating liquid that wets and adheres to the roughened surface to form an over-coated layer; connecting said cooling coil into a defrost system of said cooling system; heating said cooling coil to melt frost formed on said cooling coil; and wherein the roughened surface has a greater affinity towards the lubricating liquid as compared to frost; and wherein the lubricating liquid and frost are substantially chemically inert with each other.

In one or more embodiments, the method further includes providing an air flow to said cooling coil during or after said heating.

In one or more embodiments, the method further includes providing additional lubricating liquid to replenish any loss of the lubricating liquid during operation.

In another aspect, a method for building a pest repellent building includes providing one or more walls of a building with a roughened surface and a lubricating liquid that wets and adheres to the roughened surface to form an over-coated layer; wherein the roughened surface has feature sizes that are smaller or larger than the size of a gripping mechanism of said pest; and wherein the lubricating liquid and said pest are substantially chemically inert with each other.

In one or more embodiments, one or more walls substantially encloses the perimeter of the building and extends from the ground of the building to a height that is several times larger than the size of the pest.

In one or more embodiments, the method further includes providing additional lubricating liquid to replenish any loss of the lubricating liquid during operation.

In another aspect, a method for cleaning a surface of an article includes providing a surface of an article with a roughened surface and a lubricating liquid that wets and adheres to the roughened surface; and providing a fluid that collects contaminant accumulated on said article during use of the article; wherein the roughened surface has a greater affinity towards the lubricating liquid as compared to the fluid; and wherein the lubricating liquid and the fluid are substantially chemically inert with each other.

In one or more embodiments, the article is a building, a billboard, a sign, a fabric, a sink, or a toilet bowl.

In one or more embodiments, the contaminant include dirt, smog, fecal matter, spray paints, food, or combinations thereof.

In another aspect, a method of preventing marine biofouling on a water vessel includes providing a surface of a marine vessel with a roughened surface and a lubricating liquid that wets and adheres to the roughened surface to form an over-coated layer; and deploying said marine vessel into a marine environment; wherein the roughened surface has a greater affinity towards the lubricating liquid as compared to marine contaminants and the marine environment; wherein the lubricating liquid and the marine contaminants are substantially chemically inert with each other; and wherein the lubricating liquid and the marine environment are substantially chemically inert with each other.

In one or more embodiments, the marine contaminants include mussels, sea squirts, barnacles, tubeworm, tubeworm larva, diatom, or combinations thereof.

In one or more embodiments, the marine environment includes salt and sweet water.

In one or more embodiments, the method further includes providing additional lubricating liquid to replenish any loss of the lubricating liquid during operation.

In another aspect, a method of creating a self-cleaning, anti-sticking optical surface includes providing a surface of an optical device with a roughened surface and a lubricating liquid that wets and adheres to the roughened surface to form an over-coated layer; and providing a fluid that collects contaminant accumulated on said optical device during use; wherein the roughened surface has a greater affinity towards the lubricating liquid as compared to the fluid; and wherein the index of refraction of the lubricating liquid is substantially similar to the index of refraction of the roughened surface; and wherein the lubricating liquid and the fluid are substantially chemically inert with each other.

In one or more embodiments, the optical device is in a mobile communication device, fingerprint reader, automatic transfer machine, goggle, camera, infrared imaging system, a lens, a touch screen, or a window.

In one or more embodiments, the contaminant includes dirt, smog, oil, fingerprint, skin debris, fog, frost, ice or combinations thereof.

In any of the preceding embodiments, the lubricating liquid is a pure liquid, solution, or a complex fluids consist of a liquid phase and a solid phase.

In one or more aspects, the surface is selected from the group consisting of a slide, plate, film, work surface, well, well plate, Petri dish, tile, jar, flask, beaker, vial, test tube, column, container, cuvette, bottle, drum, vat, tank, and combinations thereof.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 11A through 11E show a replication process to reproduce the morphology of the slippery liquid-infused porous surface(s) surface, where the corresponding surface characterization shown in FIG. 11F indicates ultra-smoothness of the slippery liquid-infused porous surface(s), in accordance with certain embodiments;

FIGS. 12A through 12C show evaporation characteristics of Liquid B in porous membrane in accordance with certain embodiments;

FIG. 13C shows time-lapse images demonstrating the restoration of liquid repellency of a slippery liquid-infused porous surface(s) after physical damage, as compared to a typical hydrophobic flat surface on which oil remains pinned at the damage site in FIG. 13D, in accordance with certain embodiments;

FIGS. 15A to 15C shows schematic (FIG. 15A) and near infrared range wavelength image (i.e., wavelength >800 nm) at 50° C. (FIG. 15B) and −20° C. (FIG. 15C) of a metal block, "H", that was placed on top of a temperature-controlled plate (left), with a dry porous membrane placed over the "H" (center) and, with a porous membrane wetted with perfluorinated liquid (right) placed over the "H" (right) in accordance with certain embodiments;

FIGS. 17A through 17F show the demonstration of ice-slippery behavior of the surface of the present disclosure in outdoor environment under freezing temperature (i.e., −4° C. at a relative humidity of ~45%) in accordance with certain embodiments;

FIG. 18 shows the demonstration of ice-adhesion comparison between the surface of the present disclosure and a nanostructured surface, showing significant reduction in adhesion of ice as compared to the nanostructured surface in accordance with certain embodiments;

FIGS. 29A through 29F show a series of still images taken from a movie in which freezing tests were conducted on a slippery liquid-infused porous surface(s) aluminum alloy surface (i), a flat, unmodified aluminum alloy (ii), and a rough (sandblasted) unmodified aluminum alloy (iii) at various time points. The setup for this test is shown in FIG. 35. The alloys were in a humidity chamber on a cold plate set at −2° C. at 60% relative humidity. Water mist, droplets, frost, and ice gradually formed on each of the three surfaces and the freezing behavior was observed and captured in the still shots at 0 seconds (FIG. 29A), 1000 seconds (FIG. 29B), 1300 seconds (FIG. 29C), 1800 seconds (FIG. 29D), 2200 seconds (FIG. 29E), and 2600 seconds (FIG. 29F);

FIGS. 41A through 41D: condensation/freezing cycle from room temperature to −10° C. at 5° C./min. FIGS. 41E and 41F: melting (defrost) cycle from −10° C. to 25° C. at ~10° C./min. Ice forms mostly around the edges of slippery liquid-infused porous surface(s)-Al by bridging from the surrounding aluminum substrate while it forms uniformly all over the aluminum substrate. The sizes of the ice crystals are much larger on slippery liquid-infused porous surface(s)-Al than on aluminum, which makes contact area of ice per mass much smaller on slippery liquid-infused porous surface(s)-Al than on aluminum facilitating the removal of ice during defrost cycles. Several defects on the surface of slippery liquid-infused porous surface(s)-Al led to the pinning of droplets while they were sliding which eventually led to the formation of large ice crystals on slippery liquid-infused porous surface(s)-Al. The sample was mounted with 75 degree tilt angle. The widths of the substrates were approximately 1 inch;

FIG. 42A: Al and slippery liquid-infused porous surface(s)-Al under 60% RH at −2° C. (time=0), FIG. 42B: after 37 minutes. Frost covered 87.6% of the surface area of Al, while frost formation only takes from the edges of slippery liquid-infused porous surface(s)-Al (shown as yellow dashed lines) by bridging from the surrounding aluminum plate of the cold plate. The surface covered by frost on slippery liquid-infused porous surface(s)-Al is only 4.5%, FIG. 42C: after 100 minutes. Thick frost covered 96.1% of the surface of Al. Although 30.8% of the surface of slippery liquid-infused porous surface(s)-Al is covered with frost, they are mainly due to the edge effect. The substrates were mounted vertically. The substrates were approximately 3 inch×3 inch in size;

DETAILED DESCRIPTION OF THE INVENTION

Figure 1:
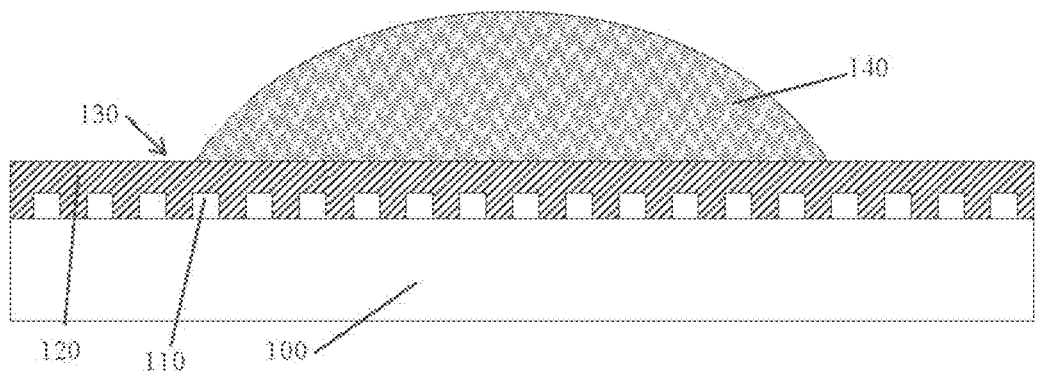
FIG. 1 is a schematic of a self-healing slippery liquid-infused porous surface (slippery liquid-infused porous surface(s)) in accordance with certain embodiments.

The present disclosure describes slippery surfaces referred to herein as slippery liquid-infused porous surface(s). In certain embodiments, the slippery surfaces of the present disclosure exhibit anti-adhesive and anti-fouling properties. The slippery surfaces of the present disclosure are able to prevent adhesion of a wide range of materials. Exemplary materials that do not stick onto the surface include liquids, solids, and gases (or vapors). For example, liquids such as water, oil-based paints, hydrocarbons and their mixtures, organic solvents, complex fluids such as crude oil, protein-containing fluids and the like can be repelled. The liquids can be both pure liquids and complex fluids. In certain embodiments, slippery liquid-infused porous surface(s) can be designed to be omniphobic, where slippery liquid-infused porous surface(s) exhibits both hydrophobic and oleophobic properties. As another example, solids like bacteria, insects, fungi and the like can be repelled. As another example, solids like ice, paper, sticky notes, or inorganic particle-containing paints, dust particles can be repelled or cleaned.

Such materials that can be prevented from sticking to the slippery surfaces disclosed herein are referred to herein as "Object A." Object A that is in liquid form is referred to as "Object A in liquid form," or "liquefied Object A," or "Liquid A." Object A that is in solid form is referred to as "Object A in solidified form," or "solidified Object A" or "Solid A." In certain embodiments, Object A can contain a mixture of both solids and fluids.

A wide range of materials can be repelled by the slippery surfaces of the present disclosure. For example, Object A can include polar and non-polar Liquids A and their solidified forms, such as hydrocarbons and their mixtures (e.g., from pentane up to hexadecane and mineral oil, paraffinic extra light crude oil; paraffinic light crude oil; paraffinic light-medium crude oil; paraffinic-naphthenic medium crude oil; naphthenic medium-heavy crude oil; aromatic-intermediate medium-heavy crude oil; aromatic-naphthenic heavy crude oil, aromatic-asphaltic crude oil, etc.), ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), acids (e.g., concentrated hydrofluoric acid, hydrochloric acid, nitric acid, etc) and bases (e.g., potassium hydroxide, sodium hydroxide, etc), and ice, etc. Object A can include biological objects, such as insects, small animals, protozoa, bacteria, viruses, fungi, bodily fluids and tissues, proteins and the like. Object A can include solid particles suspended in liquid. Object A can include non-biological objects, such as dust, colloidal suspensions, spray paints, food items, common household materials, and the like. Object A can include adhesives and adhesive films. The list is intended to be exemplary and the slippery surfaces of the present disclosure are envisioned to successfully repel numerous other types of materials.

In certain embodiments, the slippery surface of the present disclosure has a coefficient of friction that is lower than that of polytetrafluoroethylene (PTFE or TEFLON) surface. In certain embodiments, the coefficient of friction may be less than 0.1, less than 0.05, or even less than 0.04. In certain embodiments, the coefficient of friction can be measured by sliding two different surfaces against each other. The value of the coefficient will depend on the load applied onto the surfaces, the sliding velocity, and the materials of the surfaces. For example, a reference surface, such as a polished steel, could be used to slide against the target surfaces, such as Teflon, or the slippery liquid-infused porous surface(s) of the present disclosure could be used to slide against itself (e.g., slippery liquid-infused porous surface(s)/slippery liquid-infused porous surface(s)) to obtain the coefficients of friction (both static and dynamic).

A schematic of the overall design of Slippery Liquid-Infused Porous Surfaces (slippery liquid-infused porous surface(s)) is illustrated in FIG. 1. As shown, the article includes a solid surface 100 having surface features 110 that provide a certain roughness (i.e., roughened surface) with Liquid B 120 applied thereon. Liquid B wets the roughened surface, filling the hills, valleys, and/or pores of the roughened surface, and forming an ultra-smooth surface 130 over the roughened surface. Due to the ultra-smooth surface resulting from wetting the roughened surface with Liquid B, Object A 140 does not adhere to the surface.

Before describing in detail the particular components of slippery liquid-infused porous surface(s), a slippery liquid-infused porous surface(s) includes at least the following three factors: 1) the lubricating liquid (Liquid B) can infuse into, wet, and stably adhere within the roughened surface, 2) the roughened surface can be preferentially wetted by the lubricating liquid (Liquid B) rather than by the liquid to be repelled (Object A), and 3) the lubricating fluid (Liquid B) and the object or liquid to be repelled (Object A) are immiscible and do not chemically interact with each other.

The first factor can be satisfied by using micro- or nanotextured, rough substrates whose large surface area, combined with chemical affinity for Liquid B, facilitates complete wetting by, and adhesion of, the lubricating fluid. More specifically, the roughness of the roughened surface, R, is selected such that $R \geq 1/\cos \theta_{BX}$, where R is defined as the ratio between the actual and projected areas of the surface, and $\theta_{BX}$ is the equilibrium contact angle of Liquid B on a flat solid substrate immersed under medium X (X=water/air/other immiscible fluid medium). In certain embodiments, R may be any value greater than or equal to 1, such as 1.5, 2, or even 5

To satisfy the second factor, the roughened surface can be preferentially wetted by the lubricating fluid (Liquid B) rather than by the immiscible liquid/complex fluids/undesirable solids one wants to repel (Object A). This can ensure that Object A remains on top of a stable lubricating film of Liquid B.

To satisfy the third factor, the enthalpy of mixing between Object A and Liquid B should be sufficiently high (e.g., water/oil; insect/oil; ice/oil, etc.) that they phase separate from each other when mixed together, and/or do not undergo substantial chemical reactions between each other. In certain embodiments, Object A and Liquid B are substantially chemically inert with each other so that they physically remain distinct phases/materials without substantial mixing between the two.

Figure 2A:
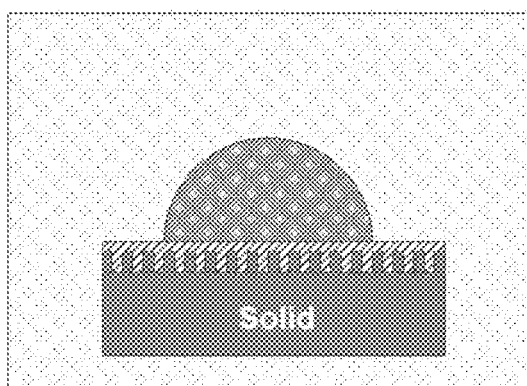
FIG. 2A shows Liquid A droplet over slippery liquid-infused porous surface(s) where Liquid B of the slippery liquid-infused porous surface(s) is exposed to both Liquid A and immiscible Medium X in accordance with certain embodiments.
Figure 2B:
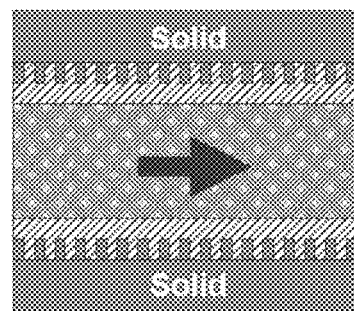
FIG. 2B shows Liquid A contacting slippery liquid-infused porous surface(s) where Liquid B of the slippery liquid-infused porous surface(s) is substantially exposed only to Liquid A in accordance with certain embodiments.

It is contemplated that slippery liquid-infused porous surface(s) may be incorporated in an environment (1) where Liquid B is exposed substantially only to Object A (e.g., flow pipe, etc.) (see FIG. 2B) or (2) where Liquid B is exposed to both Object A and another fluid environment, such as medium X (e.g., atmosphere, water, etc.) (see FIG. 2A). FIG. 2 shows Object A in the liquid form as Liquid A.

When slippery liquid-infused porous surface(s) is incorporated in the first environment (e.g., inside the interior of a pipe/tubing and alike) (see FIG. 2B), the working combinations of the substrate surface/lubricant/immiscible test fluid may be chosen by satisfying the condition shown in Equation (e1).

$$\Delta_{E0} = \gamma_{BX} \cos \theta_{BX} - \gamma_{AX} \cos \theta_{AX} > 0 \quad (e1)$$

where $\gamma_{AX}$, and $\gamma_{BX}$ represent the interfacial energies of the Object A-medium X interface, and Liquid B-medium X interface, respectively. Also, $\theta_{AX}$, and $\theta_{BX}$ are the equilibrium contact angles of Object A and Liquid B on a flat solid surface immersed under medium X environment, respectively.

On the other hand, when slippery liquid-infused porous surface(s) is incorporated in the second environment (e.g., exposed to both Liquid A and a second fluid or air environment) (see FIG. 2A), satisfying the following two conditions can provide a suitable slippery liquid-infused porous surface(s).

$$\Delta E_1 = R(\gamma_{BX} \cos \theta_{BX} - \gamma_{AX} \cos \theta_{AX}) - \gamma_{AB} > 0 \quad (e2)$$

$$\Delta E_2 = R(\gamma_{BX} \cos \theta_{BX} - \gamma_{AX} \cos \theta_{AX}) + \gamma_{AX} - \gamma_{BX} > 0 \quad (e3)$$

where $\gamma_{AB}$ represent the interfacial energies of the Object A-Liquid B interface.

In addition, the density difference between the Object A and Medium X can also play a role for the object repellency. For example, in order for Object A to slide off from slippery liquid-infused porous surface(s) by gravity, the density of Object A, $\rho_A$, may desirably be greater than that of the Medium X, $\rho_X$ (i.e., $\rho_A > \rho_X$). Moreover, the size of Object A may be on the order of, or greater than, its capillary length. Specifically, capillary length is a characteristic length scale that quantifies the dominance of gravity over surface force on an object, which can be quantitatively expressed as $(\gamma/\rho g^{1/2})$, where $\gamma$, $\rho$, and g are surface tension, density of the liquid, and gravity, respectively.

The different parameters noted in (e1), (e2) and (e3) (i.e. $\theta_{AX}$, $\theta_{BX}$, $\gamma_{AX}$, $\gamma_{BX}$, $\gamma_{AB}$, R) can be obtained or estimated utilizing the following standard techniques. While the following standard techniques are described, other techniques can be utilized, which will be apparent to those of skill in the art.

Measurement of $\theta_{AX}$, $\theta_{BX}$: Advancing and Receding Angles, Static Angles The behavior of liquids on surfaces is described by an equilibrium contact angle. An equilibrium contact angle, $\theta$, is the angle at which a liquid/vapor interface meets a solid surface, which is determined by the interactions across the three interfaces, e.g., solid/liquid/vapor. Experimentally, the most stable equilibrium contact angle of a liquid droplet on a real solid surface can be difficult to attain. Liquid droplets sitting on the solid surface exhibit a variety of contact angles bound by two extreme values. The upper limit is known as the apparent advancing contact angle ($\theta_A$), whereas the lower limit is referred as the apparent receding contact angle ($\theta_R$). The difference between these values is known as contact angle hysteresis (i.e., $\Delta\theta = \theta_A - \theta_R$, where $\theta_A \geq \theta \geq \theta_R$), which characterizes the liquid repellency of a surface. Conventionally, equilibrium contact angle can be roughly estimated by the average of the advancing and receding angles (i.e., $\theta = (\theta_A + \theta_R)/2$), or by a static contact angle, $\theta_{static}$ (i.e., $\theta = \theta_{static}$).

In practice, contact angle measurement can be performed by a number of different well-established techniques, such as the sessile drop method and the Wilhelmy method. In particular, the sessile drop method is among the most popular technique for contact angle measurement. In this technique, a liquid droplet is deposited on a targeted solid surface, where the liquid profile is captured by an optical system of a goniometer and geometrically fitted to obtain the contact angle. The contact angle measured from a static liquid droplet deposited on the surface is known as the static contact angle, $\theta_{static}$. Using the same system, advancing contact angle, $\theta_A$, can be measured while the volume of the drop is increasing until the wetting line starts to advance. Receding contact angle, $\theta_R$, can be measured by decreasing the volume of the drop and determining the contact angle just before the wetting line recedes. Alternatively, the advancing and the receding angles of the liquid drop can also be determined by gradually tilting the solid surface until the liquid drop starts to move.

Measurement of Fluid-Fluid Interfacial Tension: $\gamma_{AX}$, $\gamma_{BX}$, $\gamma_{AB}$ Fluid-fluid interfacial tension can be measured by many well-established techniques, such as the Wilhelmy plate method, the Du Noüy ring method, and the pendant drop method (e.g., see Drelich et al., in *Encyclopedia of Surface and Colloid Science, pp.* 3152-3166, Marcel Dekker Inc, 2002, the contents of which is incorporated by reference herein in its entirety). Among all of the techniques, the pendant drop method is among the most popular and versatile technique, which can be easily extended to a two-liquid system. The pendant drop method measures the shape of a fluid-fluid interface and quantifies the shape distortion due to the competition between the fluid-fluid interfacial tension and gravity. In practice, a drop of denser fluid (e.g., Object A) is suspended by a syringe needle in immiscible medium X (i.e., air/water/Liquid B). Owing to the influence of gravity, the denser liquid droplet will be deformed as the liquid volume increases. The shape profile of the liquid droplet is captured by an optical system and subsequently analyzed by a computer software when the liquid volume is increased to the maximum possible size (i.e., before the liquid drop is detached from the syringe needle). The interfacial tension of the fluid-fluid interface, $\gamma$, can then be deduced from the formula, $\gamma = \Delta \mu g D^2/H$, where $\Delta\rho$ is the density difference between the two immiscible fluids, g is gravity, D is equatorial diameter of the liquid droplet, and H is a drop shape dependent parameter which is a function of the shape profile of the droplet.

Measurement of Surface Roughness: R

Roughness of a surface can be quantitatively estimated by a number of indirect and direct approaches. For example, one of the simplest indirect methods to quantify surface roughness is the use of Wenzel's relationship to estimate the roughness by measuring the apparent contact angle of a surface. Specifically, the Wenzel's relationship can be described by the formula, $\cos \theta^* = R \cos \theta$, where $\theta^*$ and $\theta$ are the measured apparent contact angle of the roughened surface, and the equilibrium contact angle of a substantially flat surface (of same material), respectively.

For direct measurements, the surface roughness can be quantitatively measured by using an atomic force microscope or by a scanning electron microscope. Specifically, the use of atomic force microscope (AFM) allows for simple, and direct 3-dimensional mapping of the surface morphology. In practice, a suitable AFM probe is selected for the measurements depending on the aspect ratio of the surface features (note: aspect ratio is defined as the ratio between the height and the width of the surface features). As a rule of thumb, sharp AFM probes (i.e., radius of tip curvature <10 nm) of very high aspect ratio (i.e. >10) would allow for relatively precise measurements of surfaces with general morphologies. Alternatively or in addition, the use of scanning electron microscope can also be used for the measurement of the top view and cross sectional view of the surface morphologies for the estimation of the surface roughness.

In certain embodiments, the roughness of a 3-D porous material can be estimated by measuring the surface morphology of the top-most layer of the porous material. Particularly, the estimation may be particularly well-suited when complete wetting of a surface is predominately induced by the roughness at the surface layer of the material that is in intimate contact with the fluid.

The roughness can also be estimated from the surface area measurements performed by gas adsorption experiments.

Roughened Surface

As used herein, the term "roughened surface" includes both the surface of a three-dimensionally porous material as well as a solid surface having certain topographies, whether they have regular, quasi-regular, or random patterns.

In certain embodiments, the roughened surface may have a roughness factor, R, greater than 1, where the roughness factor is defined as the ratio between the real surface area and the projected surface area. For complete wetting of Liquid B to occur, it is desirable to have the roughness factor of the roughened surface to be greater or equal to that defined by the Wenzel relationship (i.e., $R \geq 1/\cos \theta$, where $\theta$ is the contact angle of Liquid B on a flat solid surface). For example, if Liquid B has a contact angle of 50° on a flat surface of a specific material, it is desirable for the corresponding roughened surface to have a roughness factor greater than ~1.5.

Figures 3A, 3B:
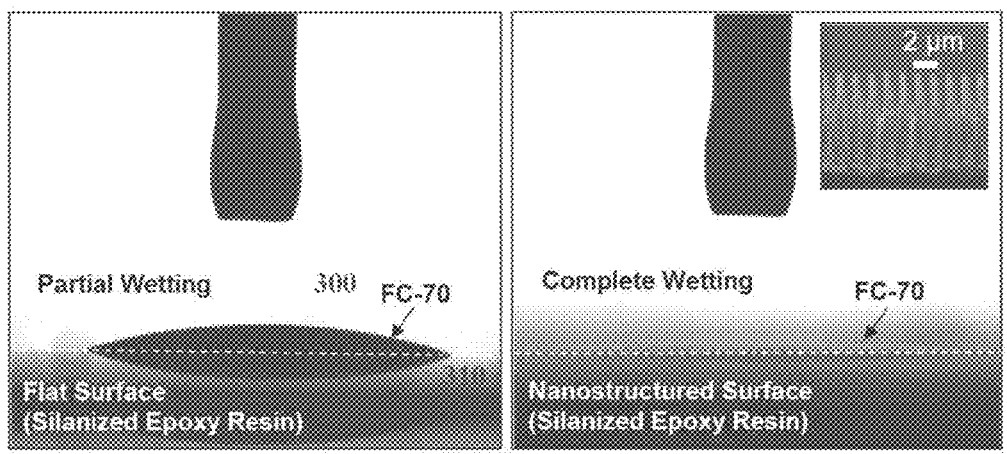
FIGS. 3A and 3B show the wetting behaviors of an exemplary fluorinated Liquid B on (FIG. 3A) flat surface and (FIG. 3B) nanostructured surface (inset shows an electron micrograph of the nanostructures) in accordance with certain embodiments.

In certain embodiments, the presence of a roughened surface can promote wetting and spreading of Liquid B over the roughened surface, as is demonstrated in FIG. 3. FIG. 3A shows a droplet 300 of Liquid B (FC-70, a high boiling point, water-insoluble perfluorinated trialkylamine) on a flat, unstructured surface 310 prepared from a silanized epoxy resin. The dashed line represents the location of the upper surface of the substrate. While the droplet spreads on the surface, it retains its droplet shape and has a finite contact angle. FIG. 3B shows the same Liquid B on an exemplary roughened surface of the same composition. The presence of the roughened surface promotes the spreading out and filling in of the droplet into the valleys of the roughened surface. As shown, the nanostructures greatly enhance the wetting of the Liquid B on the surface, creating a uniformly-coated slippery functional layer over the topographies.

In certain embodiments, the roughened surface can be manufactured from any suitable materials. For example, the roughened surface can be manufactured from polymers (e.g., epoxy, polycarbonate, polyester, nylon, Teflon, etc.), metals (e.g., tungsten, aluminum), sapphire, glass, carbon in different forms (such as diamond, graphite, black carbon, etc.), ceramics (e.g., alumina, silica), and the like. For example, fluoropolymers such as polytetrafluoroethylene (PTFE), polyvinylfluoride, polyvinylidene fluoride, fluorinated ethylene propylene, and the like can be utilized. In addition, roughened surface can be made from materials that are functional properties such as conductive/non-conductive, and magnetic/non-magnetic, elastic/non-elastic, light-sensitive/non-light-sensitive materials. A broad range of functional materials can make slippery liquid-infused porous surface(s).

Exemplary Roughened Surfaces

Figure 4:
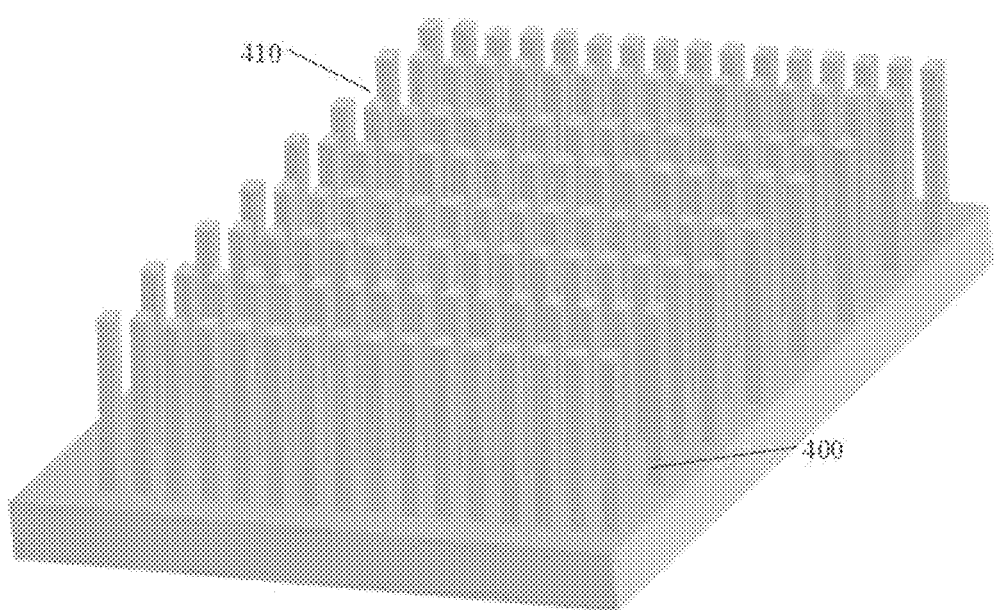
FIG. 4 is a schematic of a structured surface over which the slippery surface is formed in accordance with certain embodiments.

FIGS. 4 and 5 show some exemplary roughened surfaces. In certain embodiments, the roughened surface may be formed over any desired shapes. For example, the roughened surface may be formed over a two-dimensionally flat surface 400 by providing certain raised structures or protrusions 410 (see FIG. 4). In another example, roughened surface may be formed by forming pores 520 over a two-dimensionally flat surface to form a porous material (see FIG. 5A). In another example, a three-dimensionally interconnected network of regular or random pores may be utilized (see FIGS. 5B and 5C).

In certain embodiments, the roughened surface is a hierarchical surface containing surface features on multiple length scales. By way of example, the surface can have a first topological feature having dimensions on the microscale and a second topological feature on the nanoscale. The first topological feature supports the second smaller topological feature. The second topological features are referred to as "primary structures" as they are meant to denote the smallest feature sizes of the hierarchical structure. The primary structures can include structures, such as nanofibers, nanodots, and the like. Such nanoscale "primary structures" can have at least one kind of feature sizes that are a few to tens or hundreds of nanometers in size, such as less than 5 nm to 200 nm. For example, nanofibers having diameters of approximate 5, 10, 25, 50, or even 100 nm. In such cases, when "primary structures" having feature sizes of about 100 nm diameter is utilized, "secondary structures" having feature sizes that are larger than 100 nm, such as 150 nm, 300 nm, 500 nm, or 1000 nm, and larger can be utilized. Additional higher order structures, such as "tertiary structures" and the like, which each has larger feature sizes than the lower order structures are contemplated.

Particularly, hierarchical structures shown in FIGS. 6A to 6F having different combinations of bumps, nanofibers, rods, or spheres, posts, mushrooms, and the like may provide a high degree of three-dimensional porosity that may be well-suited for use as porous surfaces described herein. A detailed discussion of hierarchical surfaces suitable for use as a roughened surface is found in International Application No. PCT/US11/44553 entitled "Hierarchically structures surfaces to control wetting by liquids", filed on Jul. 19, 2011, which is incorporated in their entirety by reference.

Raised Structures as Roughened Surface

In certain embodiments, the roughened surface may have a periodic array of surface protrusions (e.g., posts, peaks, etc.) or any random patterns or roughness (see FIG. 4). In some embodiments, the size scale of the features producing a roughened surface ranges from 10 nm to 100 μm with geometries ranging from regular posts/open-grid structures to randomly oriented spiky structures. In some embodiments, the widths of the raised structures are constant along their heights. In some embodiments, the widths of the raised structures increase as they approach the basal surface from the distal ends. The raised structures can be raised posts of a variety of cross-sections, including, but not limited to, circles, ellipses, or polygons (such as triangles, squares, pentagons, hexagons, octagons, and the like), forming cylindrical, pyramidal, conical or prismatic columns. Their surface can be smooth or corrugated in a regular or irregular way, e.g., as in the scalloping that is found in a Bosch process. Although the exemplary substrates described above illustrate raised posts having uniform shape and size, the shape, orientation and/or size of raised posts on a given substrate can vary.

The raised structures can be produced by any known method for fabricating raised structures onto substrates. Non-limiting examples include conventional photolithography, projection lithography, e-beam writing or lithography, focused-ion beam lithography, depositing nanowire arrays, growing nanostructures on the surface of a substrate, soft lithography, replica molding, solution deposition, solution polymerization, electropolymerization, electroplating, electroless deposition, vapor deposition, contact printing, etching, transfer patterning, microimprinting, self-assembly, and the like.

For example, a silicon substrate having a post array can be fabricated by photolithography using the Bosch reactive ion etching method (as described in Plasma Etching: Fundamentals and Applications, M. Sugawara, et. al, Oxford University Press, (1998), ISBN-10: 019856287X, the contents of which is incorporated by reference herein in its entirety). Further exemplary methods are described in PCT/US09/48880, the contents of which is incorporated by reference herein in its entirety.

Patterned surfaces can also be obtained as replicas (e.g., epoxy replicas) by a soft lithographic method (see, e.g., J. Aizenberg and B. Pokroy, PCT/US2009/048880, the contents of which is incorporated by reference herein in its entirety). Polymer films with patterned surfaces can be fabricated by means known in the art (e.g., roll-to-roll imprinting or embossing).

In certain embodiments, the roughened surface can be made, for example, by replica molding procedure described in B. Pokroy, A. K. Epstein, M. C. M. Persson-Gulda, J. Aizenberg, *Adv. Mater.* 21, 463 (2009), the contents of which is incorporated by reference herein in its entirety. Negative replicas of pre-generated patterns can be made from polydimethylsiloxane, PDMS (e.g., Dow-Sylgard 184) by pouring mixture of prepolymer and curing agent (e.g., 10:1 ratio) on the patterns followed by thermal curing in an oven. After cooling, the negative PDMS mold can be peeled off and used for fabricating the final replica by pouring the desired material (e.g. UV-curable epoxy resin) into the negative mold. After solidifying the material, the negative mold can be peeled off, leaving the replica of the original pattern. Then, the surface of the replica can be chemically functionalized with low surface energy coating such as (tridecafluoro-1,1,2,2-tetrahydrooctyl)-trichlorosilane or other reagents having appropriate reactive end groups and straight or branched hydrocarbon or fluorocarbon chains or their combinations.

Three-Dimensionally Porous Materials as Roughened Surface

In certain embodiments, the roughened surface may be the porous surface layer of a substrate with arbitrary shapes and thickness. The porous surface can be any suitable porous network having a sufficient thickness to stabilize Liquid B, such as a thickness from above 100 nm, or the effective range of intermolecular force felt by the liquid from the solid material. Below 100 nm thick, the liquid may start to lose its liquid property. The substrates can be considerably thicker, however, such as metal sheets and pipes. The porous surface can have any suitable pore sizes to stabilize the Liquid B, such as from about 10 nm to about 2 mm. Such a roughened surface can also be generated by creating surface patterns on a solid support of indefinite thickness.

In certain embodiments, the pore size of the porous material can roughly be on the order of the capillary length of Liquid B or smaller. Such size may allow stabilizing Liquid B in the porous material. Capillary length, $\lambda_c$, can be defined as $\lambda_c = \sqrt{\gamma/\rho g}$, where $\gamma$ is the surface tension of Liquid B, $\rho$ is the density of Liquid B, and g is gravity.

Taking the exemplary case of utilizing fluorinated liquids as Liquid B, the surface tension of fluorinated liquids is in the range of about 10-20 mN/m at a typical density of about 1800 kg/m$^3$ or above. Typical pore sizes can range from about 50 nm to about 100 μm or up to about 1 mm, such as about 750 μm-1 mm.

In certain embodiments, the roughened surface can have feature sizes that are nanoscopic in size, such as less than 1 μm or less than 100 nm. Such feature sizes may be particularly useful in repelling insects that utilize hooks that have sizes on the range of about 5-10 μm to assist in climbing on the slippery liquid-infused porous surface(s). In addition, the presence of the Liquid B may also effectively prevent the attachment of insects or animals that utilize micro/nano-structures to adhere to the surfaces through intermolecular forces (e.g., beetle, fly, spider, and gecko etc.).

In certain embodiments, the roughened surface can have pores that are comparable or smaller than the Object A to be repelled. For examples, pore sizes that are smaller than sizes of insects' hooks (e.g., on the range of about 5-10 μm) may further aid in inhibiting insects from climbing on the slippery liquid-infused porous surface(s).

Exemplary porous materials include solid substrates having holes (e.g., high aspect ratio holes, cylinders, columns, etc.), three-dimensionally interconnected network of holes and one or more materials (e.g., 3-D ordered colloidal assemblies, block copolymers, etc.), random array of fibrous materials (e.g., filter paper, fabrics, electrospun films, etc.), and the like.

Many porous materials are commercially available, or can be made by a number of well-established manufacturing techniques. For example, PTFE filter materials having a randomly arranged three-dimensionally interconnected network of holes and PTFE fibrils are commercially available. FIGS. 5A to 5D illustrate three non-limiting exemplary embodiments of suitable porous materials.

Figure 5A:
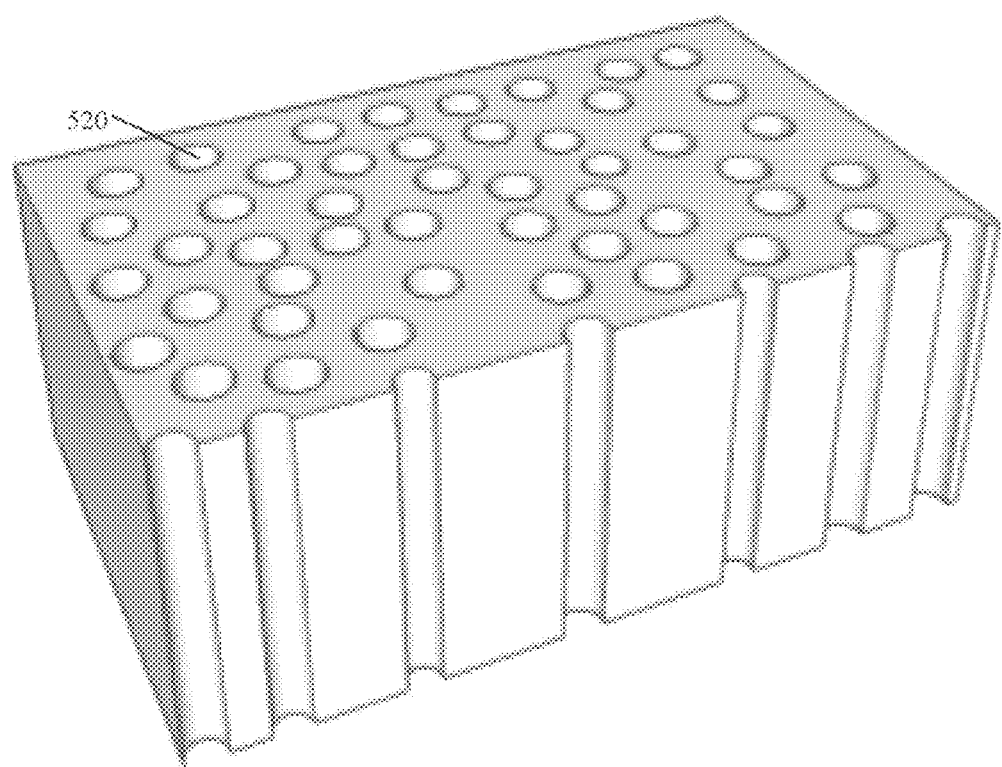
FIG. 5A is a schematic of a columnar porous material over which the slippery surface is formed in accordance with certain embodiments.

For example, as shown in FIG. 5A, porous alumina can be manufactured by the process of anodization, where an aluminum substrate is electrochemically oxidized under constant electrical potential. The pore size, inter-pore spacing, and the aspect ratio of the pores can be tuned by adjusting the operating parameters of the electrochemical oxidation process. Such a process generates porous through-holes into the substrate, where the size of the porous holes are on the order of 50 nm with aspect ratio larger than 10000 (See, Lee et al., *Nature Mater.* 5, 741-47, 2006, the contents of which is incorporated by reference herein in its entirety.).

In some embodiments, mechanical or (electro)chemical methods can be used to roughen metal surfaces. Roughening and non-wetting materials can be spray coated directly onto metal surfaces. Boehmite (γ-AlO(OH)) formation on aluminum surface by boiling in water can also be used to roughen metallic surfaces such as aluminum. Rotary jet spinning of hydrophobic polymer nanofibers and layered deposition of an appropriate primer can also be used to roughen substrates for use in slippery liquid-infused porous surface(s).

Figure 5B:
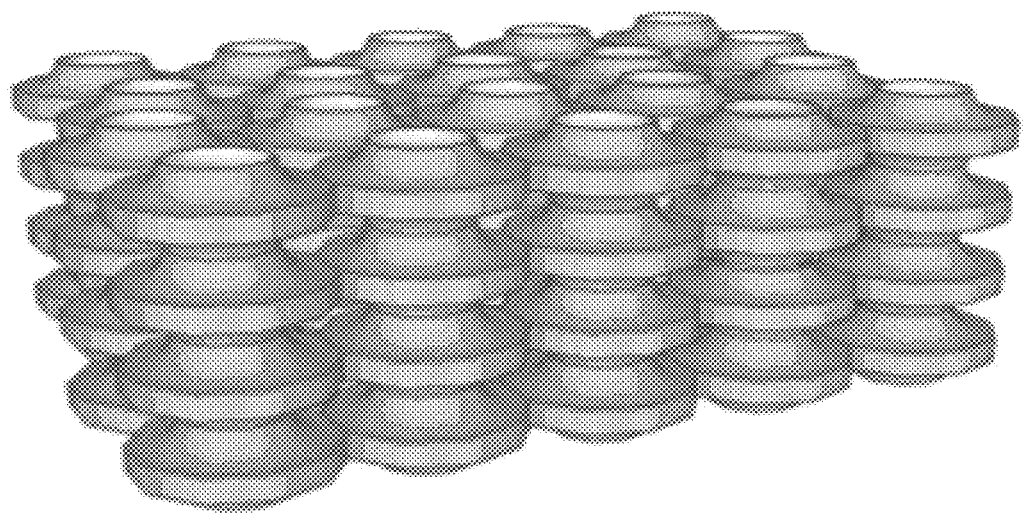
FIG. 5B is a schematic of an inverse opal porous material over which the slippery surface is formed in accordance with certain embodiments.

In yet another example, as shown in FIG. 5B, long range ordered porous structures of silica can be produced by evaporative co-assembly method of sacrificial polymeric colloidal particles together with a hydrolyzed silicate sol-gel precursor solution. Such a method may be able to generate a crack-free porous surface on the order of centimeters or larger, with pore sizes of about 100 nm to about 1000 nm and porosity of about 75%. (See, Hatton, et al., *Proc. Natl. Acad. Sci.* 107, 10354-10359, 2010 and U.S. patent application Ser. No. 13/058,611, filed on Feb. 11, 2011, the contents of which is incorporated by reference herein in its entirety.).

Figure 5C:
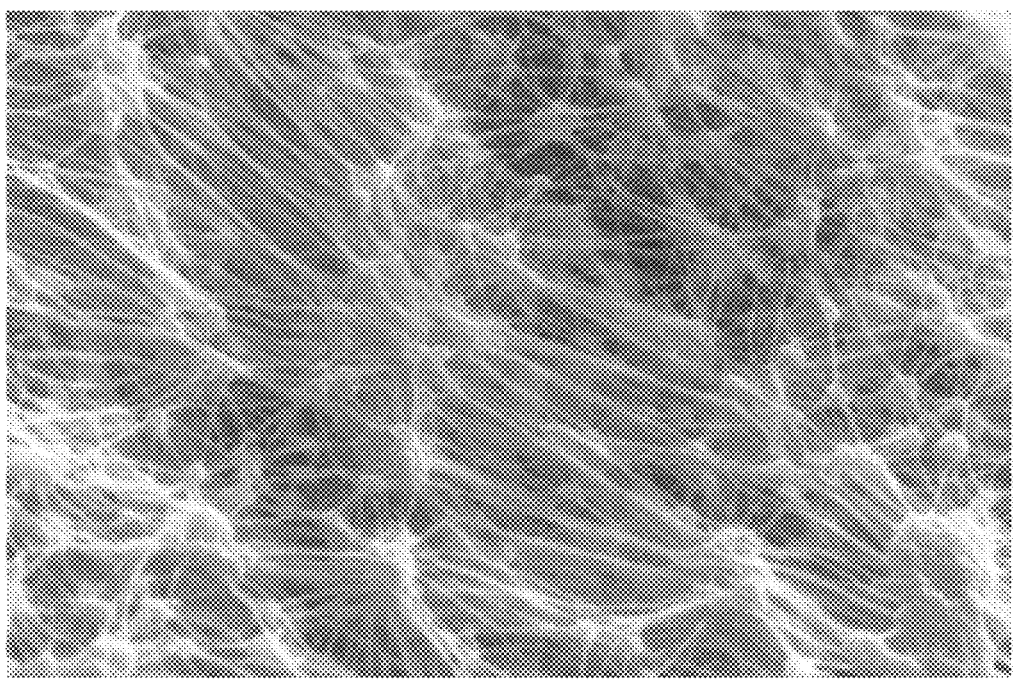
FIG. 5C is an image of a random network porous material over which the slippery surface is formed in accordance with certain embodiments.

In another example, as shown in FIG. 5C, to manufacture polymer-based porous membrane (such as PTFE), one of the methods can include mixing PTFE powders with lubricants (e.g., naphtha) to form a paste. Then, the paste can be molded into the desired shape by methods such an extrusion molding. The molded PTFE membrane can then be heated up to less than its melting point to drive off the lubricants. Thereafter, a porous PTFE membrane can be formed. (See, U.S. Pat. No. 5,476,589, the contents of which is incorporated by reference herein in its entirety.).

Figure 5D:
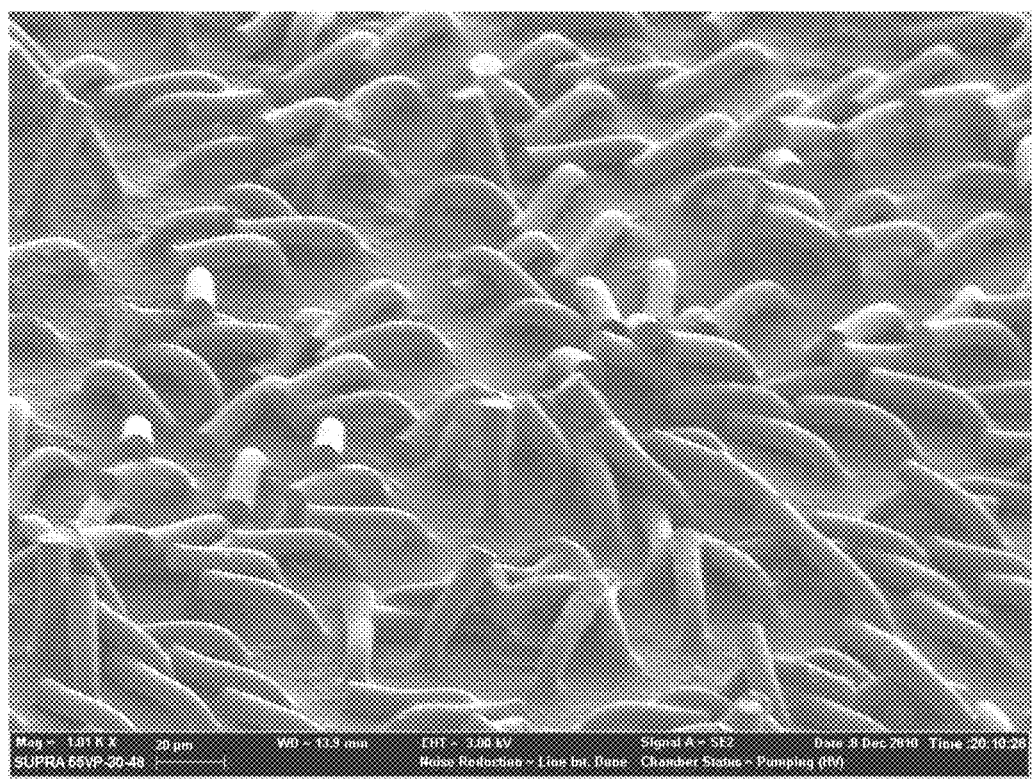
FIG. 5D is an image of self-assembled polymeric microstructures induced by solvent drying in accordance with certain embodiments.

In certain embodiments, the polymeric replica of raised structures can be self-assembled and collapsed into a random network of porous structures (e.g., similar to a mesh of "spaghetti" structures) through an evaporation-induced assembly process initiated by a drying solvent, e.g., ethanol (see FIG. 5D). The resulting assembled structures can be infiltrated with Liquid B to form slippery liquid-infused porous surface(s).

Any other suitable technique for obtaining a porous roughened surface can be utilized. In certain embodiments, the porous roughened surface may be commercially available materials, such as a filter material. In certain embodiments, the porous roughened surface may be formed as part of a pre-existing process for forming a desired device or part of a device.

Accordingly, to favor complete wetting of the roughened surface by Liquid B to form a chemically homogeneous and physically smooth over-coated layer, it is desirable for the roughened surface to have high chemical affinity to Liquid B, high surface roughness, or both. Given a known Liquid B, its chemical affinity towards the roughened surface can be measured by a contact angle, θ. The lower is the contact angle; the stronger is the chemical affinity of Liquid B towards the roughened surface.

By convention, when θ<90°, a liquid is said to have a high chemical affinity to the solid surface; otherwise the liquid is said to have a low chemical affinity when θ>90°. Depending on the chemical affinity of the liquids, the surface roughness needs to be engineered accordingly in order to form a completely wetted film. Given a known contact angle of the liquid on a flat solid, the roughness requirement of the solid, R, to form a completely wetted liquid film can be defined by the Wenzel's relationship (i.e., R≥1/cos θ). Detailed examples of roughened/porous solids and the corresponding chemical functionalization have been described in the U.S. Patent Application Nos. 61/434,217 and 61/466,352.

The following are some additional non-limiting examples on the manufacturing of functionalized roughened/porous solids applicable to the fabrication of slippery liquid-infused porous surface(s).

1. Spraying

In one example, the roughened, porous material can be generated by a spraying method, where emulsions consisting of micro/nanoparticles are sprayed onto a solid surface (either flat/roughened). These particles assemble into roughened solid layer upon solvent drying. One suitable spraying technique is described in Poetes et al., *Phys Rev. Lett.* 105, 166104 (2010), the contents of which is incorporated by reference herein in its entirety. Such a solid layer can then be infiltrated by Liquid B (which can also be applied by additional spraying).

2. Electrodeposition

In yet another example, the porous material can be generated in-situ on a metal surface by an electrodeposition method, such as the STEP method (STEP=structural transformation by electrodeposition on patterned substrates, See, U.S. Provisional Patent Application Ser. No. 61/365,615, filed on Jul. 19, 2010 and PCT/US11/44553, filed on Jul. 19, 2011, and Kim, et al., *Nano Lett.*, DOI: 10.1021/nl200426g, (2011), the contents of which is incorporated by reference herein in its entirety.

In certain embodiments, the porous surface can be prepared by using an electrodeposition process. The electrodeposition condition can be controlled so that nanofibers of electrically conductive polymer can be formed over an electrically conductive surface. The electrodeposition conditions can further be controlled to provide a desired nanofiber diameter and spacing. In certain embodiments, the electrodeposition condition can be controlled to provide any other desirable morphology that can provide additional means to stabilize Liquid B.

The morphology of the conducting organic polymers can be controlled by varying the deposition conditions such as the concentration of monomer, the types of electrolytes and buffers, the deposition temperature and time, and the electrochemical conditions such as applied potential. For example, increasing the concentration of monomer in the electrochemical solution, the applied potential, and/or the temperature generally leads to a faster polymerization rate and many parasitic nucleation sites during growth resulting in a morphology that is similar to a cauliflower (see FIG. 6A). In contrast, lower concentrations of monomer, lower applied potential, and lower temperatures can lead to nanofibril growth with substantially uniform diameters (see FIG. 6B). Further decrease in concentration of monomer or applied potential can lead to short rods of polymer nanofibers with low surface coverage (see FIG. 6C). In another example, increasing the type of electrolytes and buffers to obtain a more acidic solution can lead to the formation of a cauliflower shape (see FIG. 6A) or overgrowth of polymers (see FIG. 6D). In another example, the applied voltage can be cycled leading to different oxidation states of the deposited polymer layer which is often manifested as a color change (e.g., from dark blue to a green then to a pale yellow color with increasing applied voltage). In yet another example, the applied voltage can be pulsed at a constant voltage to form polymers only on the tip of the underlying micropost structures, leading to a mushroom-like morphology (see FIG. 6E). In yet another example, the fibrous surface can be made on an array of raised features, to form a hierarchical roughness (see FIG. 6F). Accordingly, the morphology of conducting organic polymers can be finely controlled from nanometers to over micrometer scales, and surface coatings with precisely controlled morphology can be produced by simple modifications, which promise the customization of various surface properties by design and control of the morphology.

3. Abrasive Blasting

Many solid surfaces can be made roughened by the process of abrasive blasting. During this process, a stream of abrasive particles propelled by high pressure gas/liquid are hitting onto the targeted solid surfaces, thereby removing the surface materials from the solids through physical bombardment. Some examples of abrasive blasting are bead blasting, sand blasting, wet abrasive blasting, and hydro-blasting. The solid surfaces that are treated by abrasive blasting can then be post-treated with other methods, such as spray coating (described in U.S. Patent Application No. 61/466,352, p. 12, [0079]), to enhance their chemical affinity towards a specific lubricant. As a specific example demonstrated by Steiner and co-workers (Poetes et al., *Phys Rev. Lett.* 105, 166104 (2010)), an aluminum substrate was roughened by the process of bead blasting, which was followed by spray-coating a primer (DuPont 459-804) and a Teflon suspension (DuPont 852-200). This process creates a highly roughened surface with fluorinated surface chemistry (i.e., Teflon), which would display strong chemical affinity to lubricants such as perfluorinated fluids (e.g., 3M™ Fluorinert™ or Dupont™ Krytox® oils).

4. Dry Etching

Dry etching techniques make use of reactive plasma/ gaseous species to remove targeted solid materials. Both directional (anisotropic) and non-directional (isotropic) etching can be achieved depending on the operating conditions (e.g., pressure, gas flow, power etc.). For example, isotropic etching of materials is usually carried out under low vacuum environment, as compared to the anisotropic etching in which high vacuum environment is required. Different reactive gaseous species are available to etch a variety of materials, such as silicon, glass, silicon nitride, aluminum, tungsten, and polymers etc. (See, e.g., K. R. Williams et al., *J. MEMS,* 12, pp. 761-778 (2003)). High-aspect-ratio structures (i.e., height/width $\gg 1$) with well-defined side-wall profiles (e.g., vertical/slanted side-wall) can be generated by the anisotropic etching methods; whereas isotropic etching techniques can be utilized to generate low-aspect-ratio structures (i.e., height/width $<\sim 1$) with undercutting or rounded side-wall profiles. Examples of anisotropic etching methods, such as the Bosch process, have been described in the U.S. Provisional Patent Application 61/466,352. For examples of isotropic etching, Tuteja et al. (Tuteja et al., *Science* 318, 1618-1622 (2007)) showed that mushroom-like textures can be fabricated on silicon using patterned silicon-dioxide as a masking material and xenon difluoride ($XeF_2$) as a gas etchant under a low vacuum environment. Similar structures can be produced on aluminum or polymers using appropriate etchants and masking materials.

5. Metal Foams/Porous Metals

Metal foams are porous metallic substrates. These porous substrates can be formed typically by the solidification process of a mixture of pre-melted metals with injected gas/gas-releasing blowing agents, or by compressing metal powders into special tooling to form different shapes and forms (e.g., sheet, cylindrical shape, hollow cylinders etc.). Metal foams can be manufactured either in closed-cell or open-cell structures (i.e., interconnected network of metals). Metal foams of different materials, such as aluminum, titanium, nickel, zinc, copper, steel, iron, or other metals and alloys, have been produced by various methods, such as direct foaming and powder compact melting methods, which have been extensively discussed in J. Banhart, *Prog. Mater. Sci* 46, 559-632 (2001). These foams have found extensive applications in automotive/aerospace industries, ship building, railway industry, as well as biomedical industry.

6. Polymer Fiber Spinning

Porous surfaces can be manufactured through the process of electro-spinning or rotary jet spinning. Specifically, electro-spinning uses electric charge to draw micro/nanoscale fibers from a liquid, such as polymer solution. These fibers can be directly drawn onto a targeted solid substrate to form polymeric porous surfaces with controlled fiber density. Many polymeric materials can be used during this process such as nylon, polyurethanes, polycarbonate, polyacrylonitrile, polyvinyl alcohol, polymethacrylate, polyaniline, polystyrene, polyamide, collagen, polypropylene, polyethylene napthalate, etc. In rotary jet spinning, highspeed rotating polymer solution jets are extruded to form aligned fibers. Fiber morphology, diameter, and web porosity can be controlled by varying nozzle geometry, rotation speed, and polymer solution properties, which have been extensively discussed in Badrossamay et al., *Nano Lett.* 2010, 10 (6), pp 2257-2261.

Figure 45A:
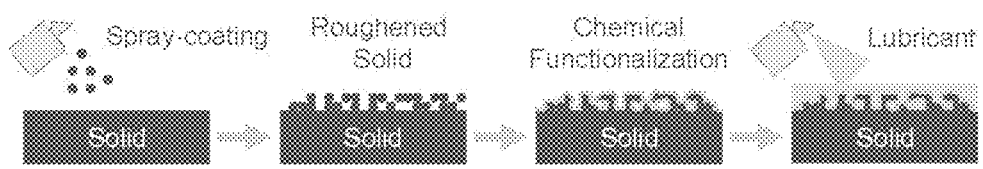
FIGS. 45A through 45C provide exemplary manufacturing techniques to form slippery liquid-infused porous surface(s). First, a solid material can be made roughened by spray-coating as shown in FIG. 45A; chemical/physical etching as shown in FIG. 45B; and solution/vapor phase deposition of materials onto the solid as shown in FIG. 45C. After the solid is roughened, the surface can be chemical-functionalized to enhance the chemical affinity of the lubricant.
Figure 45B:
Figure 45C:

FIGS. 45A-45C provide a schematic illustration summarizing the previous discussion of the various manufacturing methods that can be employed to prepare the roughened porous substrate. Referring to FIG. 45A, the roughened porous surface can be generated by a spraying method, where emulsions consisting of micro/nanoparticles are sprayed onto a flat solid surface. These particles assemble into roughened solid layer upon solvent drying. Such a solid layer can then be infiltrated by lubricating fluid (which can also be applied by additional spraying). Non-limiting examples of micro/nanoparticles that can be sprayed onto a flat solid surface to form roughened, porous material include titanium dioxide, silicon dioxide, nanodiamonds, metals such as silver, gold, platinum, copper, gold, palladium, zinc, and titanium, hydroxyapatite (HAp) nanoparticles.

In one or more embodiments, as shown in FIG. 45B, the roughened, porous substrate is generated using an etchant method. The substrate is roughened by etching. The etchant is carried by a preformed pipe and deposited onto the substrate to create a roughened surface. Once the surface is roughened, it is functionalized with a liquid (not shown) or vapor silane, and infiltrated with a lubricating liquid.

In other embodiments as shown in FIG. 45C, the roughened, porous substrate is made by growing a nanostructured material on the surface. A nanostructured material is grown on the surface of the substrate to create a roughened surface that is functionalized with a liquid (not shown) or vapor silane and infused with a lubricating liquid. Non-limiting examples of these nanostructures include PPy nanofibers, carbon nanotubes, and the like. One the nanostructures are in place, the surface can be chemically functionalized by silanization and infiltrated with a lubricating liquid.

Certain Advantages of Porous Roughened Surfaces

Use of a three-dimensionally porous roughened surface may provide several advantages. At least the following advantages can be noted.

1. Arbitrary Geometries

First, since the physical structures are already embedded within the bulk material, further structuring of the surface may not be needed. In such cases, the porous material can be a self-supporting, free-standing membrane which can be attached/glued/adhered to the external or internal surfaces of materials with any kind of geometry (see FIG. 7A).

Figure 7A:
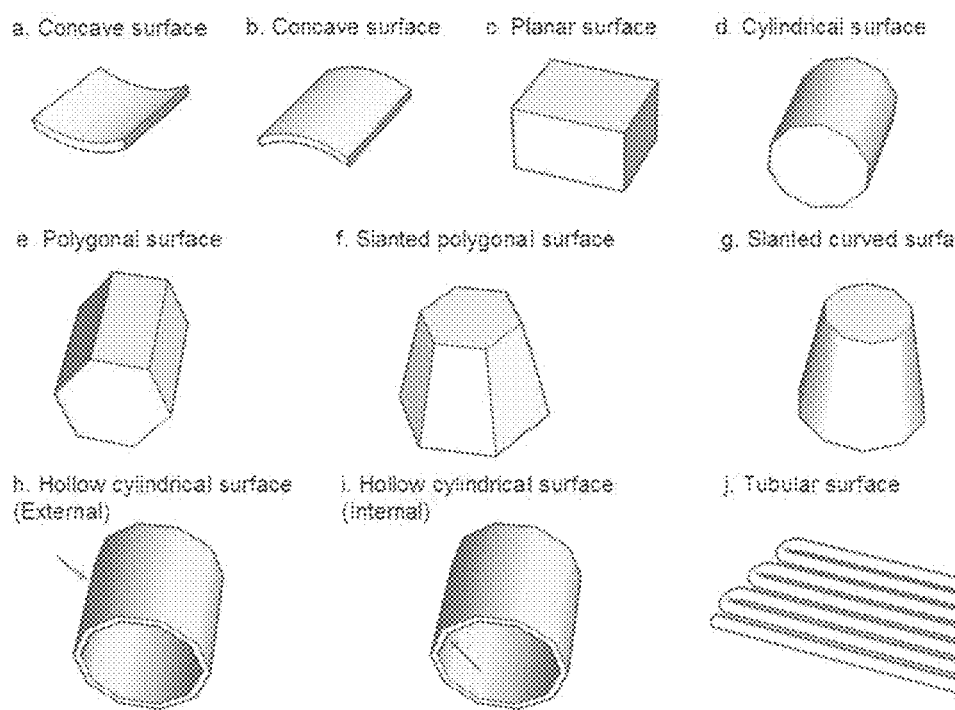
FIG. 7A shows several different planar and non-planar surfaces over which slippery liquid-infused porous surface(s) can be formed in accordance with certain embodiments.
Figure 7B:
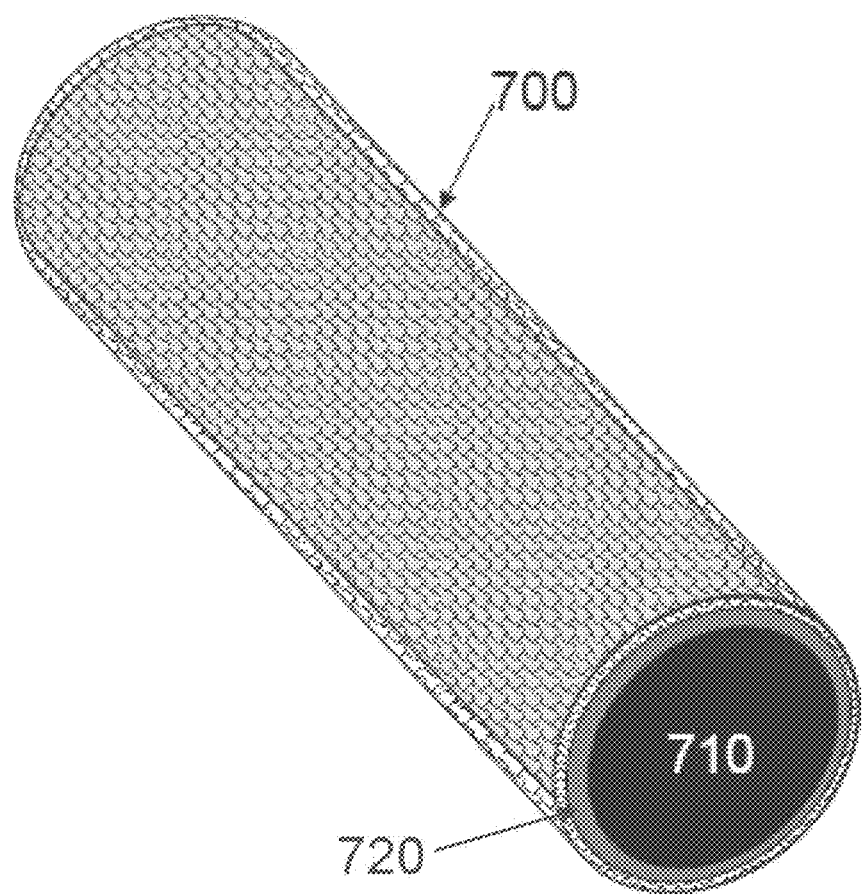
FIG. 7B shows slippery liquid-infused porous surface(s) formed over a cylindrical solid core in accordance with certain embodiments.
Figure 7C:
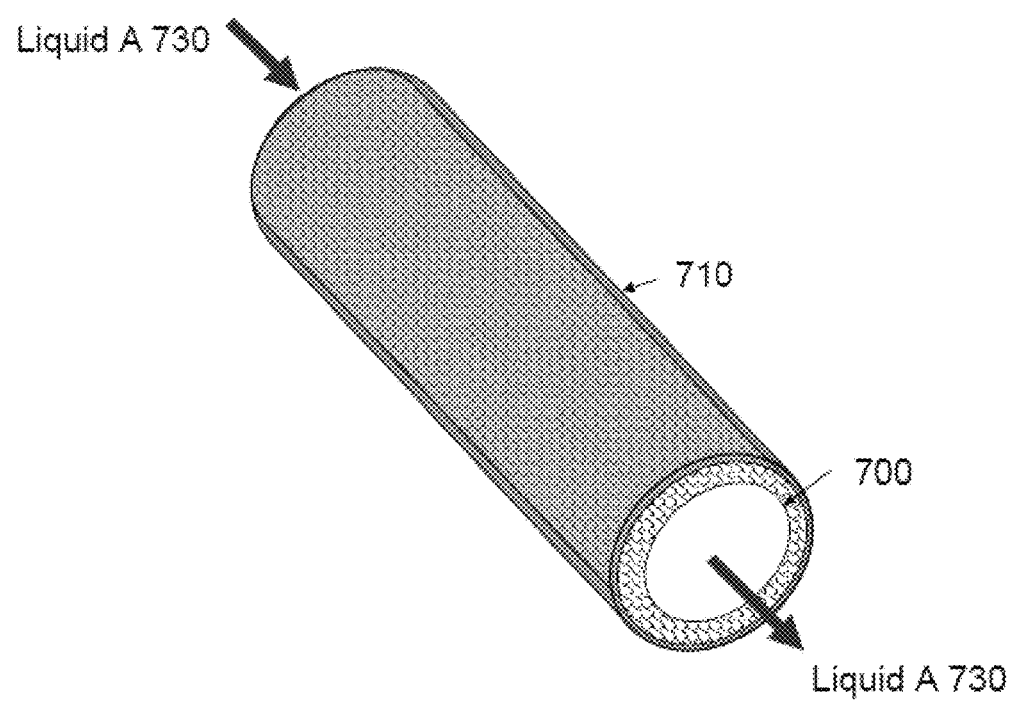
FIG. 7C shows slippery liquid-infused porous surface(s) formed on the sidewall of the interior of a tubing/pipe and the like in accordance with certain embodiments.
Figure 7D:
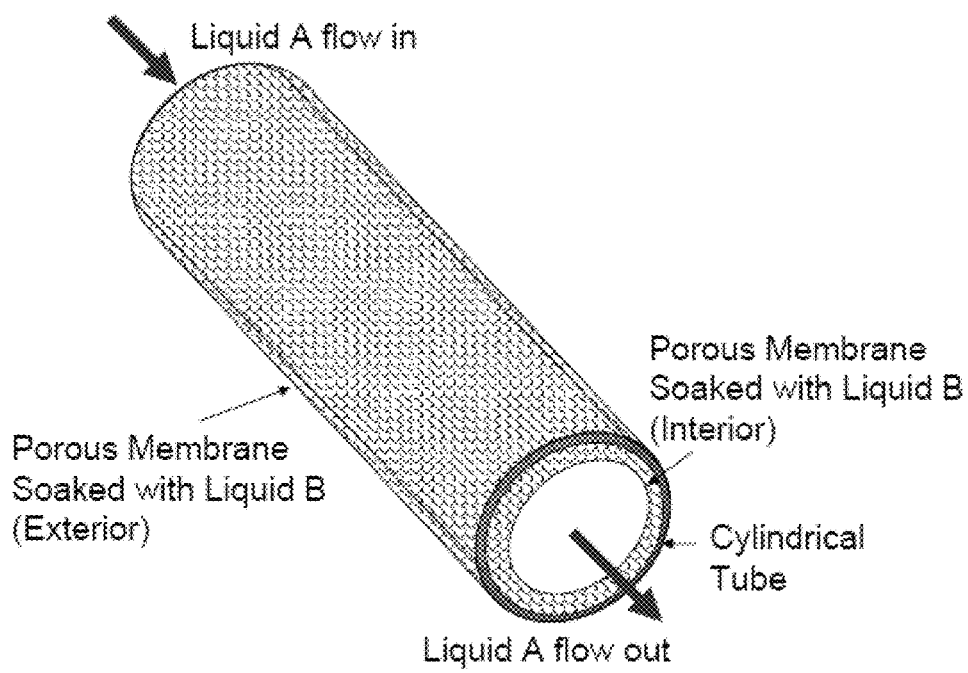
FIG. 7D shows slippery liquid-infused porous surface(s) formed on the sidewall of both of the interior and exterior of a tubing/pipe and the like in accordance with certain embodiments.
Figure 7E:
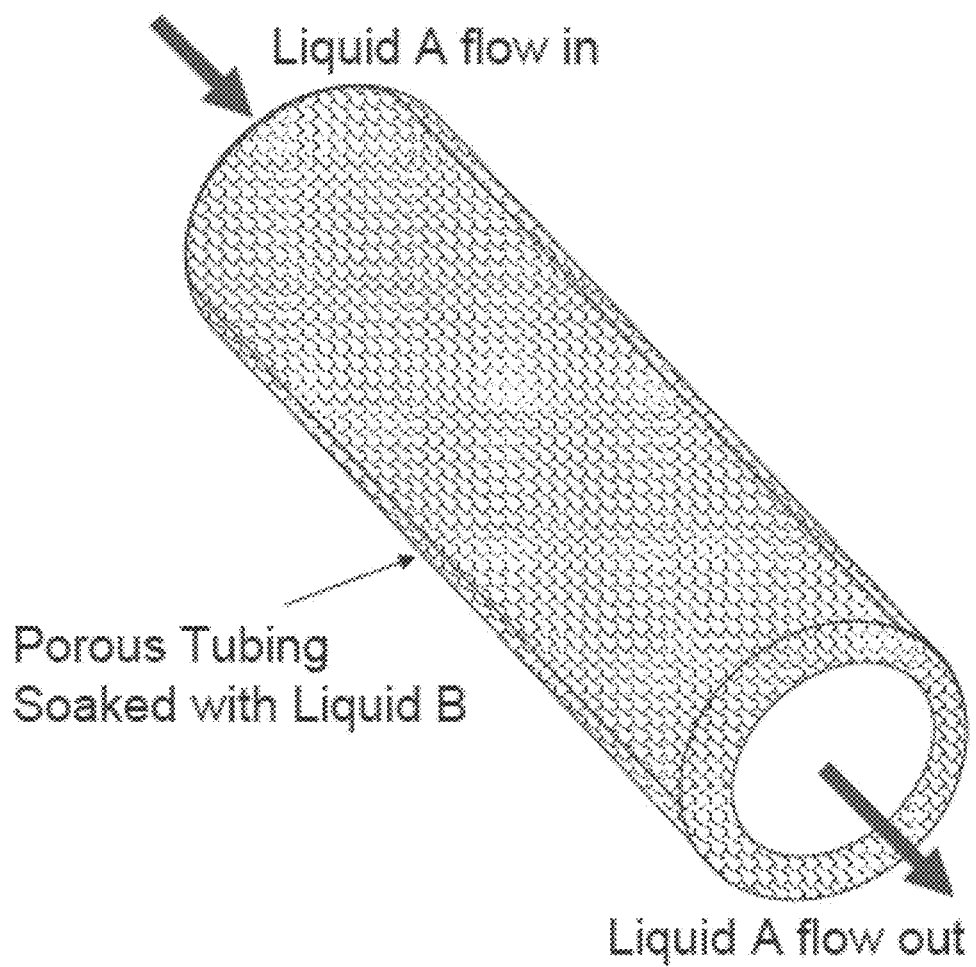
FIG. 7E shows slippery liquid-infused porous surface(s) formed on the Liquid-B-soaked porous tubing and the like in accordance with certain embodiments.

In certain embodiments, the roughened surface can be formed over or applied to a variety of planar or non-planar surface (see FIGS. 7A and 7B). For example, FIG. 7B shows a slippery liquid-infused porous surface(s) 700 attached to the outer surface of a cylindrical solid core 710 with a reservoir 720 for Liquid B. Alternatively, slippery liquid-infused porous surface(s) can also be attached to the inner surfaces of the tubes, pipes, and other irregularly shaped substrates. For example, as shown in FIG. 7C, slippery liquid-infused porous surface(s) 700 can be applied to the inner surface of a cylindrical tube 710 for low drag flow of Liquid A 730. In addition, as shown in FIG. 7D, slippery liquid-infused porous surface(s) can be applied onto both the inner and outer surfaces of a tube/needle with the same/different kind of lubricants (denoted as Liquid B and B' in FIG. 7D) for low drag flow of Liquid A and remain slippery/non-sticking to the outside environments where the tube/needle is exposed to. Also, as shown in FIG. 7E, slippery liquid-infused porous surface(s) can be applied onto a Liquid-B-soaked porous tubing for low drag flow of Liquid A and remain slippery/non-sticking to the outside environments where the porous tube/needle is exposed to. Tubular structures having any arbitrary cross-section, either constant or variable, can also be used in the same context described in the above examples.

Figure 46:
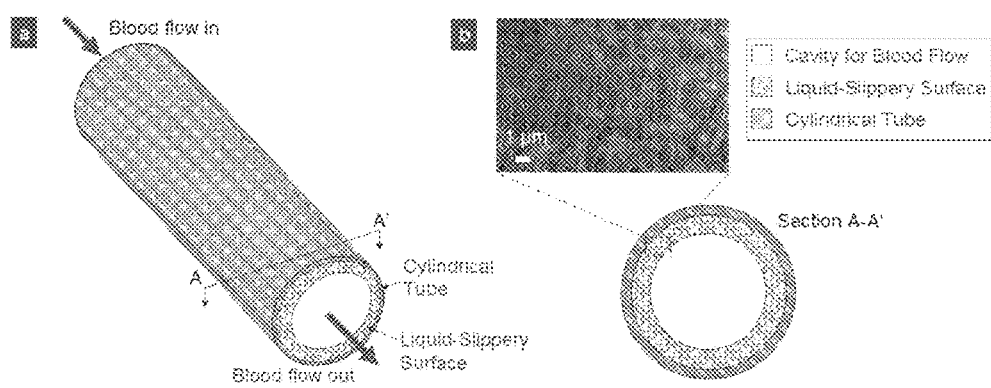
FIG. 46 is a schematic that shows how slippery liquid-infused porous surfaces can be incorporated into a catheter tube.

Non-limiting examples of shapes, forms, and configurations slippery liquid-infused porous surfaces can take include generally tubular (e.g., for a cannula, connector, catheter, needle, capillary tube, or syringe) (see view j of FIG. 7A), planar (e.g., for application to a microscope slide, plate, film, or laboratory work surface) (see view c of FIG. 7A, or arbitrarily shaped (e.g., well, well plate, Petri dish, tile, jar, flask, beaker, vial, test tube, column, container, cuvette, bottle, drum, vat, or tank) (see views a-b and d-i of FIG. 7A). FIG. 46 is a schematic that shows how slippery liquid-infused porous surfaces can be incorporated into a catheter tube. In this embodiment, a slippery liquid-infused porous surfaces forms a continuous layer on the inner surface of the tube.

In certain embodiments, the porous surface can be manufactured over any suitable materials and geometries, such as refrigerator coils, large metal sheets, shingles, siding sheets, spheres, ball-bearing, medical devices, outdoor and road signs, inside of pipes (e.g., metallic or metalized water or oil pipes; plastic pipes), inside and outside of needles, inside and outside of bottles or containers, windows, lens, screens (e.g., on mobile devices, fingerprint reader, computer monitor, or automatic teller machine), tubings, hollow metallic structures, patterned electrodes, meshes, wires, porous conductive surfaces, fabrics, clothes, shoes, and the like.

In one or more of the above embodiments, non-limiting examples of surface to which slippery liquid-infused porous surfaces is applied include a cannula, connector, catheter (e.g., central line, peripherally inserted central catheter (PICC) line, urinary, vascular, peritoneal dialysis, and central venous catheters), catheter connector (e.g., Leur-Lok and needleless connectors), clamp, skin hook, cuff, retractor, shunt, needle, capillary tube, endotracheal tube, ventilator, associated ventilator tubing, drug delivery vehicle, syringe, microscope slide, plate, film, laboratory work surface, well, well plate, Petri dish, tile, jar, flask, beaker, vial, test tube, tubing connector, column, container, cuvette, bottle, drum, vat, tank, organ, organ implant, or organ component (e.g., intrauterine device, defibrillator, corneal, breast, knee replacement, and hip replacement implants), artificial organ or a component thereof (e.g., heart valve, ventricular assist devices, total artificial hearts, cochlear implant, visual prosthetic, and components thereof), dental tool, dental implant (e.g., root form, plate form, and subperiosteal implants), biosensor (e.g., glucose and insulin monitor, blood oxygen sensor, hemoglobin sensor, biological microelectromechanical devices (bioMEMs), sepsis diagnostic sensor, and other protein and enzyme sensors), bioelectrode, endoscope (hysteroscope, cystoscope, amnioscope, laparoscope, gastroscope, mediaslinoscope, bronchoscope, esophagoscope, rhinoscope, arthroscope, proctoscope, colonoscope, nephroscope, angioscope, thoracoscope, esophagoscope, laryngoscope, and encepbaloscope) wound dressing (e.g., bandages, sutures, staples), and combinations thereof.

2. High Pressure Stabilities

In certain embodiments, slippery liquid-infused porous surface(s) may provide high pressure stabilities without losing any of the beneficial properties of slippery liquid-infused porous surface(s) described herein. In certain embodiments, slippery liquid-infused porous surface(s) may provide high resistance to changes in pressure without losing any of the beneficial properties of slippery liquid-infused porous surface(s) described herein.

In certain embodiments, use of a porous material for the roughened surface may provide extremely high pressure stabilities. For example, use of a porous material (e.g., Teflon membrane) may be able to tolerate absolute pressure up to about $6.8 \times 10^7$ Pa while maintaining its slippery characteristics. Without wishing to be bound by theory, the improved pressure tolerance of the 3D porous material can be attributed to the incompressibility of the lubricating layer, as well as the resistance of liquid impalement into the porous structure.

Figure 8:
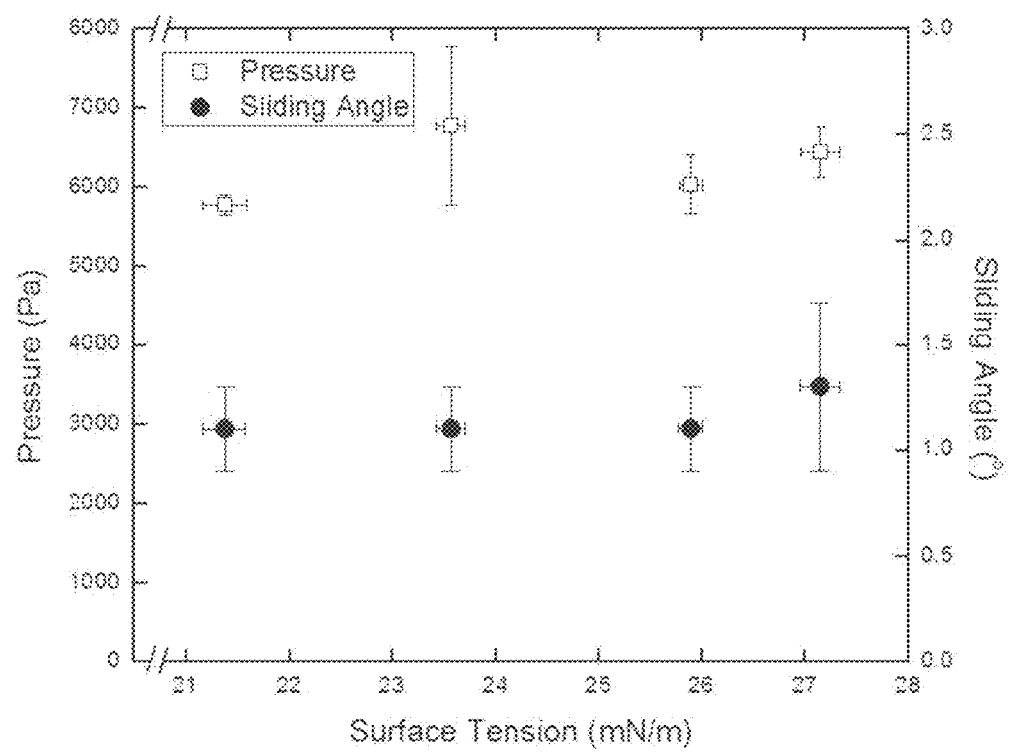
FIG. 8 is a chart showing the high pressure stability of the surface of the present disclosure as demonstrated by the repellency of low surface tension liquids at ultra-low sliding angles (i.e., <2°) after high pressure liquid impact (i.e., pressure difference >5000 Pa) in accordance with certain embodiments (Test liquids=octane, decane, tridecane, and hexadecane)

FIG. 8 shows the applied pressure (left axis) and the sliding angle at which Object A (Test liquids are octane, decane, tridecane, and hexadecane) slides off the slippery liquid-infused porous surface(s) (right axis) as a function of the surface tension. As shown, slippery liquid-infused porous surface(s) retains its slippery function under pressures of more than $1 \times 10^3$ or $1 \times 10^4$ when in contact with with a test fluid (as shown in FIG. 8), or reaching, $1 \times 10^5$, $1 \times 10^6$, $1 \times 10^7$, or even $6.8 \times 10^7$ Pa under pressurized environment.

In certain embodiment, these pressure stabilities can be achieved when the applied pressure is lower than the solidification pressure of Liquid B (e.g. order of GPa for perfluorotri-n-pentylamine). For example, Liquid B may be selected to have characteristics of high pressure stability by selecting fluids that have solidification pressure that is higher than the anticipated applied pressure during application.

In certain embodiments, the roughened surface can be selected so that the underlying roughened surface structures do not impose sharp points where stresses are concentrated around those sharp features. The presence of sharp points may introduce stress concentration points so that as Object A impinges on the slippery liquid-infused porous surface(s) at high pressures, Liquid B is locally displaced also due to the sharp points, Object A then encounters the sharp points, breaks apart, and wets the underlying roughened surface before Liquid B has a chance to heal itself.

In certain embodiments, use of a porous material for the roughened surface may provide extremely high resistance to pressure changes that may occur. For example, while using a plurality of raised nanostructures shown in FIG. 4 as the roughened surface may be able to sustain a maximum rate of pressure change on the order of $10^5$ Pa per second, use of a porous material (e.g., Teflon membrane, FIG. 5C) may be able to tolerate pressure change up to about $6\times10^6$ Pa per second without displacing Liquid B. Without wishing to be bound by theory, the improved resistance to pressure changes can be attributed to the enhanced capillary interactions between the intricate, large surface area 3D porous network and Liquid B.

In certain embodiments, Liquid B and the roughened surface can be selected so that they can sustain rapid pressure changes. For example, the slippery surface of the present disclosure may be able to withstand a pressure change of more than $1\times10^5$, $5\times10^5$, $1\times10^6$, $5\times10^6$, or even more than $6\times10^6$ Pa per second 3. Facile Replenishment of Liquid B Another advantageous feature of using porous materials may be the presence of the capillary network within the bulk materials, which can further enhance transport of Liquid B through the pores. The porous structure can provide a replenishing fluid at the surface and may be useful to address evaporation or other materials loss of Liquid B from the slippery liquid-infused porous surface(s) surface. For example, in the case where a portion of Liquid B is reduced at the surface of the materials due to evaporation, sudden pressure purging, physical damage or the like, Liquid B can be replenished by the capillary action in these networks. Replenishing Liquid B is drawn through the porous body of the substrate by capillary wicking to refresh the upper surface of slippery liquid-infused porous surface(s). In certain embodiments, the porous material itself can be utilized as a fluid reservoir to store Liquid B for subsequent capillary refilling purpose.

Figure 9A:
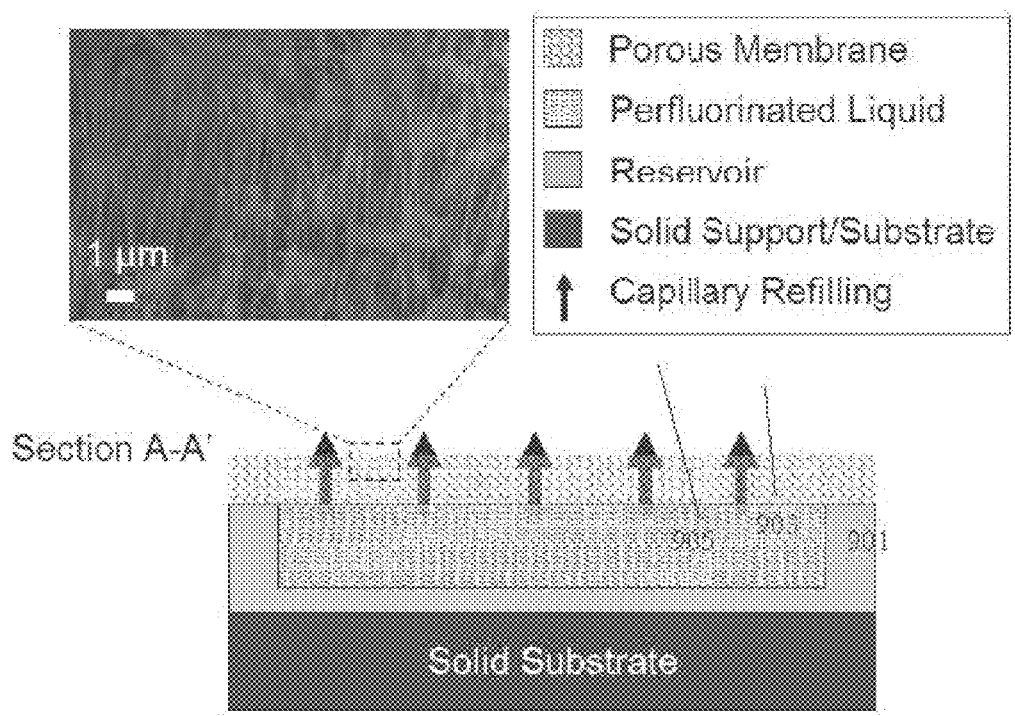
FIG. 9A shows slippery liquid-infused porous surface(s) coupled to a Liquid B reservoir that can replenish evaporating or removed Liquid B in accordance with certain embodiments.

In certain embodiments, as shown in FIG. 9A, to further prolong the life time of the slippery surface of the present disclosure, the porous material 905 can be connected to an external fluid reservoir 903 sitting on a solid substrate 901, where the capillary networks within the porous material 905 can help transfer (e.g., via wicking) the Liquid B from the fluid reservoir 903 to the porous material 905.

Figure 9B:
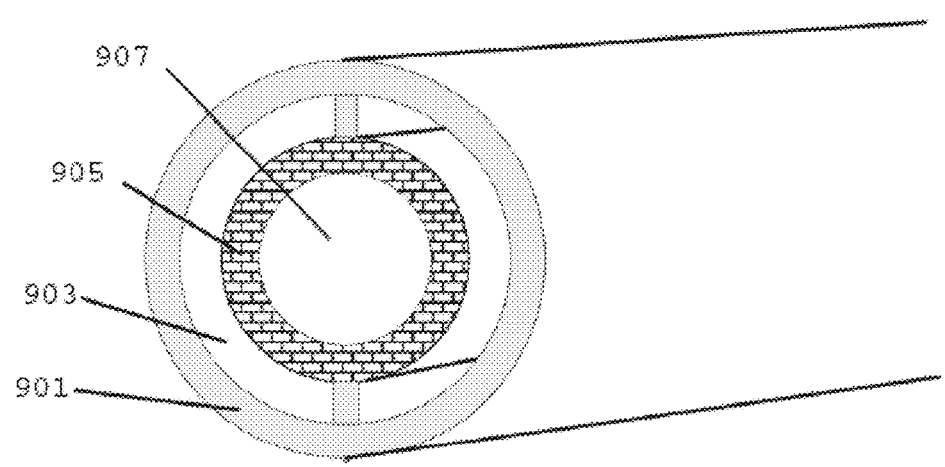
FIG. 9B shows slippery liquid-infused porous surface(s) formed inside a cylindrical tube with a Liquid B reservoir that can replenish evaporating or removed Liquid B in accordance with certain embodiments.

FIG. 9B shows an alternate embodiment where slippery liquid-infused porous surface(s) having a porous material 905 as the roughened surface is formed in an inner surface of a cylindrical tube. As shown, the cylindrical tube 901 has a first annular region 903 serving as a fluid reservoir for Liquid B, followed by an inner annular region of slippery liquid-infused porous surface(s) having a porous material 905, which surrounds a hollow region 907 for the flow of Liquid A. In operation, Liquid B in annular region 903 transfers into (e.g., via wicking) the porous material 905 to form a slippery liquid-infused porous surface(s) and Liquid A can flow through the hollow region with little to no drag at the interface between 905 and 907.

Figure 9C:
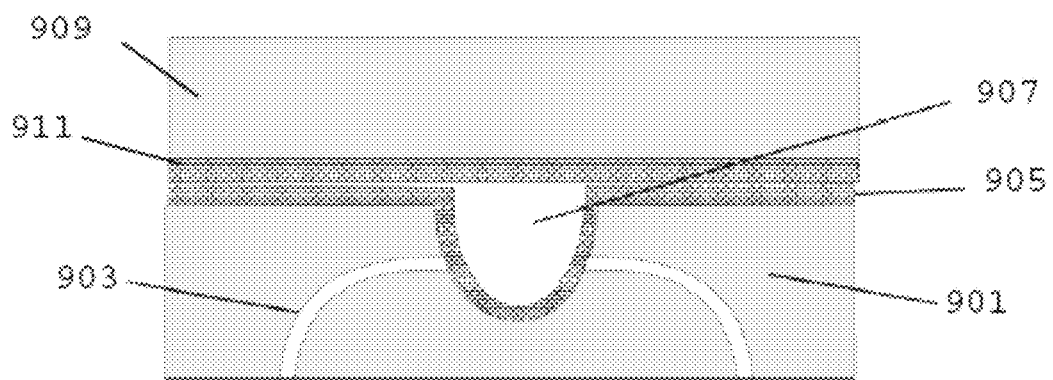
FIG. 9C shows slippery liquid-infused porous surface(s) formed along the surface of an arbitrary shaped flow path coupled to a channel for replenishing evaporating or removed Liquid B in accordance with certain embodiments.

FIG. 9C shows yet another embodiment where slippery liquid-infused porous surface(s) is formed in an inner surface of an arbitrarily shaped flow path. As shown, the bottom substrate 901 has a channel 903 serving as a fluid replenishment source for Liquid B that is coupled to the porous material 905 of slippery liquid-infused porous surface(s). Porous material 905 is formed by combining a bottom substrate 901 having a depressed region joined with a top substrate 909 having a substantially flat porous material 911 formed thereon. The combination of the top and bottom substrate portions form a hollow region 907 for the flow of Liquid A.

Figure 9D:
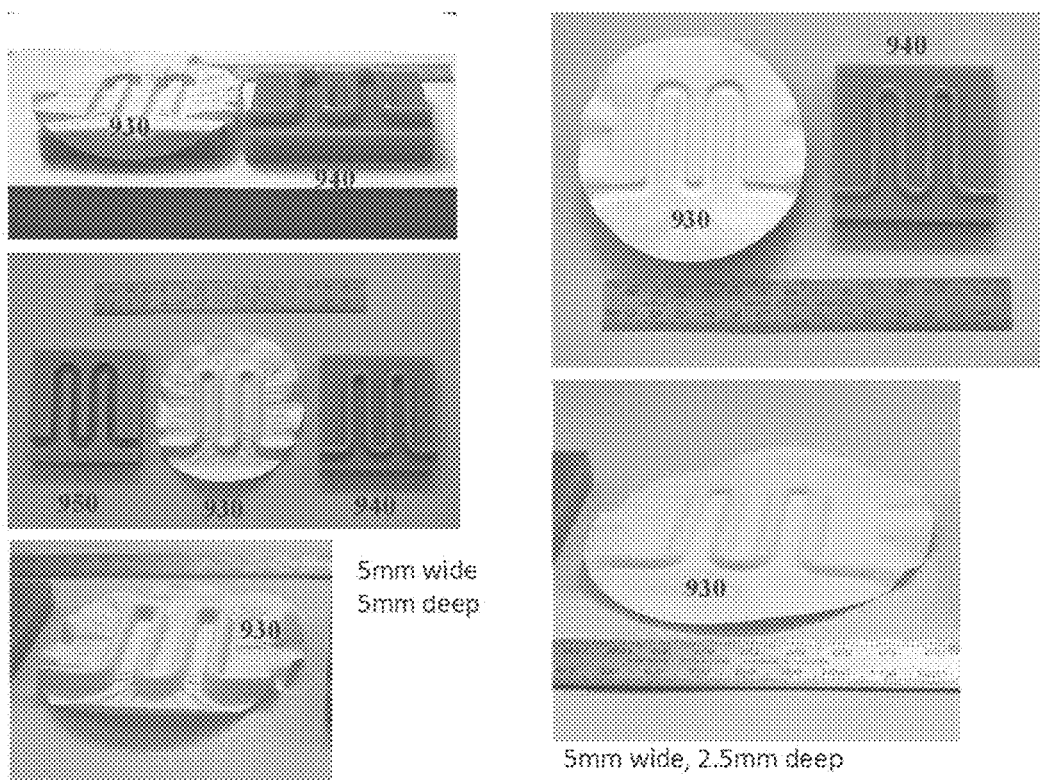
FIG. 9D shows images of showing the formation of the bottom substrate portion of FIG. 9C in accordance with certain embodiments.

FIG. 9D shows some optical photographs on how the bottom substrate 901 and slippery liquid-infused porous surface(s) 905 of FIG. 9C can be formed. As shown, a TEFLON filter paper 930 having a three-dimensionally random network of pores can be placed between a male mold 940 and female mold 950 defining an arbitrary flow path and the male mold 940 and female mold 950 can be pressed together to replicate the flow path pattern on the TEFLON filter paper 930. The templated TEFLON filter paper 930 can be placed inside the female mold 950, which now serves as bottom substrate 901 of FIG. 9C, and a substantially flat substrate 909 having another substantially flat TEFLON filter paper, serving as slippery liquid-infused porous surface(s) 911, can be applied thereon (not shown) to form the flow path 907 shown in FIG. 9C. The female mold 950 may further contain channel 903 (not shown) that serves to replenish Liquid B as needed.

Figure 10:
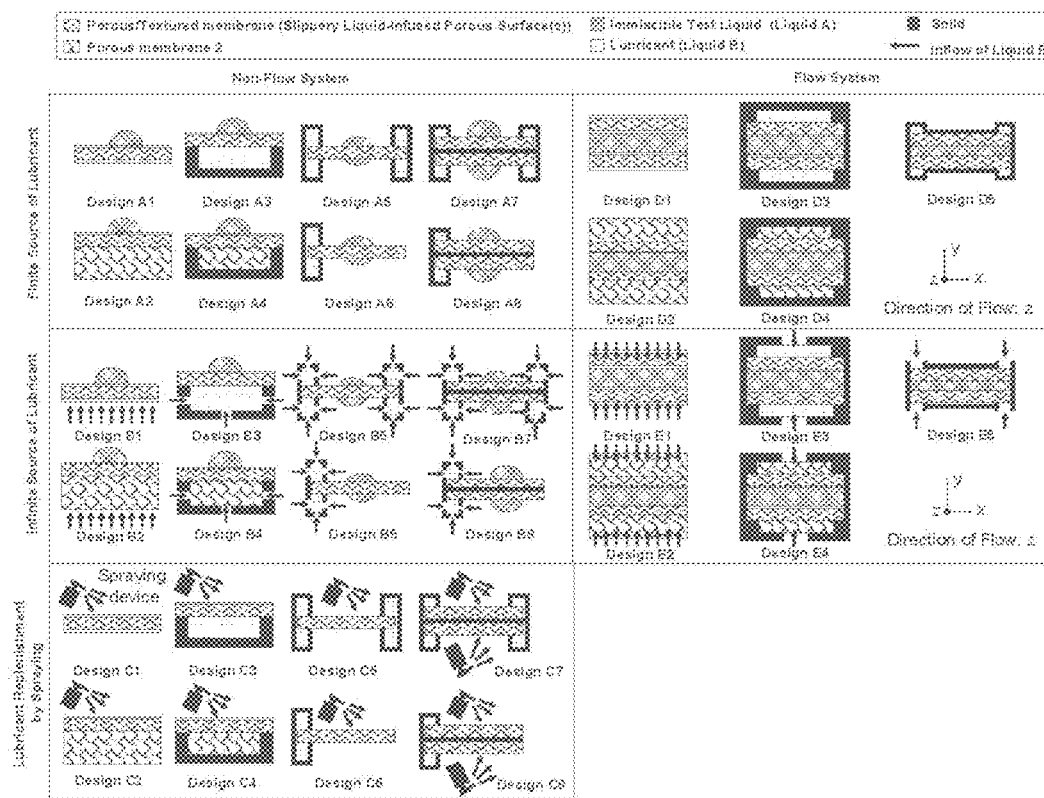
FIG. 10 shows cross section schematics of the examples of self-replenishment mechanisms of Liquid B of slippery liquid-infused porous surface(s), which can be combined or modified as needed, in accordance with certain embodiments.

FIG. 10 shows several other non-limiting embodiments of slippery liquid-infused porous surface(s) and how Liquid B can be replenished to the slippery liquid-infused porous surface(s) in each of those embodiments. The left column corresponds to systems where slippery liquid-infused porous surface(s) is exposed to both Medium X and Liquid A (shown as a droplet). The right column corresponds to systems where slippery liquid-infused porous surface(s) is exposed to substantially only Liquid A (shown as a plug between two slippery liquid-infused porous surface(s)). In either system, Liquid B can be replenished to slippery liquid-infused porous surface(s) as needed. The top row shows scenarios where there is a finite amount of Liquid B. The middle row shows scenarios where there is a large source (e.g., practically infinite source from the viewpoint of the amount of Liquid B needed to replenish the slippery liquid-infused porous surface(s)) of Liquid B. The bottom row shows scenarios where Liquid B can be replenished by spraying Liquid B as needed, either manually or automatically. As shown, many different configurations and their derivatives are possible.

It should be noted that while the embodiments described herein refers to a porous material, any other suitable roughened surface described herein can be utilized.

Other Embodiments

In certain embodiments, the solid surface may be substantially flat. This situation may be applicable when the critical surface energy of the flat surface is higher than the surface tension of the functional Liquid B. For instance, a substantially flat surface may be able to adhere a thin layer of Liquid B due to surface forces.

Object A

Physical Size of Object A Relative to its Capillary Length

In certain embodiments, Object A may slide off from slippery liquid-infused porous surface(s) by gravity when the surface is tilted at an angle with respect to the horizontal, given that the size of Object A, either in liquid form or in solidified form, is larger than a characteristic size. Specifically, the effect of gravity on Object A may be more dominant when its size is much larger than the capillary length of Liquid A. Specifically, capillary length is a characteristic length scale that quantifies the dominance of body force over surface force on an object, which can be quantitatively expressed as $(\gamma/\rho g)^{1/2}$, where $\gamma$, $\rho$, and g are surface tension and density of the liquid, and gravity, respectively. For example, size of Solid A or of Liquid A may be at least 3 times larger than the capillary length of Liquid A.

As noted previously, a wide range of materials can be repelled by the slippery surfaces of the present disclosure. For example, Object A can include polar and non-polar Liquids A and their solidified forms, such as hydrocarbons and their mixtures (e.g., from pentane up to hexadecane and mineral oil, paraffinic extra light crude oil; paraffinic light crude oil; paraffinic light-medium crude oil; paraffinic-naphthenic medium crude oil; naphthenic medium-heavy crude oil; aromatic-intermediate medium-heavy crude oil; aromatic-naphthenic heavy crude oil, aromatic-asphaltic crude oil, etc.), ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), acids (e.g., concentrated hydrofluoric acid, hydrochloric acid, nitric acid, etc) and bases (e.g., potassium hydroxide, sodium hydroxide, etc), wine, soy sauce and the like, ketchup and the like, olive oils and the like, grease, soap water, surfactant solutions, and frost or and ice, etc. Object A can include biological objects, such as insects, blood, small animals, protozoa, bacteria (or bacterial biofilm), viruses, fungi, bodily fluids and tissues, proteins and the like. Object A can include solid particles (e.g., dust, smog, dirt, etc.) suspended in liquid (e.g., rain, water, dew, etc.). Object A can include non-biological objects, such as dust, colloidal suspensions, spray paints, fingerprints, food items, common household items, and the like. Object A can include adhesives and adhesive films. The list is intended to be exemplary and the slippery surfaces of the present disclosure are envisioned to successfully repel numerous other types of materials.

In certain embodiments, more than one different Object A can be repelled. In certain embodiments, the combination of two or more Object A may together be more readily repelled as compared to just one Object A.

Liquid B

Liquid B (alternatively referred to as the "lubricant" through the specification) can be selected from a number of different materials, and is chemically inert with respect to the solid surface and Object A. Liquid B flows readily into the surface recesses of the roughened surface and generally possesses the ability to form an ultra-smooth surface when provided over the roughened surface. In certain embodiments, Liquid B possesses the ability to form a substantially molecularly flat surface when provided over a roughened surface. The liquid can be either a pure liquid, a mixture of liquids (solution), or a complex fluid (i.e., a liquid+solid components). For instance, FIGS. 11A-11F show a replication process to reproduce the morphology of the slippery liquid-infused porous surface(s) surface. First, a porous solid was infiltrated with Liquid B (e.g., perfluorinated fluid). Then polydimethylsiloxane (PDMS) was cured over the Liquid B layer to obtain a negative replica of the slippery liquid-infused porous surface(s) surface. Then, epoxy resin (e.g., UVO 114) was used to obtain a positive replica using the PDMS negative replica. Then metrology analysis was carried out with an atomic force microscope. As shown, the average roughness of the positive replica surface was less than 1 nm, where the roughness represents an upper bound for the actual roughness of Liquid B as this reaches the physical roughness limits for flat PDMS and UVO 114 epoxy resin (see Xu et al., *J. Am. Chem. Soc.* 127, 854-855, 2005; Matsunaga et al., *J. Am. Chem. Soc.* 133, 5545-5553, 2011). Nonetheless, it is evident from the roughness analysis that Liquid B overcoats the surface topographies of the porous solid, forming a nearly molecularly smooth surface.

In certain other embodiments, Liquid B possesses the ability to form a substantially molecularly or even atomically flat surface when provided over a roughened surface.

Materials

Liquid B can be selected from a number of different liquids. For example, perfluorinated hydrocarbons or organosilicone compound (e.g. silicone elastomer) and the like can be utilized. In particular, the tertiary perfluoroalkylamines (such as perfluorotri-n-pentylamine, FC-70 by 3M, perfluorotri-n-butylamine FC-40, etc), perfluoroalkylsulfides and perfluoroalkylsulfoxides, perfluoroalkylethers, perfluorocycloethers (like FC-77) and perfluoropolyethers (such as KRYTOX family of lubricants by DuPont), perfluoroalkylphosphines and perfluoroalkylphosphineoxides as well as their mixtures can be used for these applications, as well as their mixtures with perfluorocarbons and any and all members of the classes mentioned. In addition, long-chain perfluorinated carboxylic acids (e.g., perfluorooctadecanoic acid and other homologues), fluorinated phosphonic and sulfonic acids, fluorinated silanes, and combinations thereof can be used as Liquid B. The perfluoroalkyl group in these compounds could be linear or branched and some or all linear and branched groups can be only partially fluorinated.

Density

In certain embodiments, Liquid B has a high density. For example, Liquid B has a density that is more than 1.0 g/cm$^3$, 1.6 g/cm$^3$, or even 1.9 g/cm$^3$. In certain embodiments, the density of Liquid B is greater than that of Object A to enhance liquid repellency. High density fluids reduce the tendency of any impacting liquid to 'sink' below the surface of Liquid B and to become entrained therein. For Object A that is smaller than its capillary length (assume Object A is in liquid form), it is possible that the Liquid B has a density lower than that of the Object A, where the slippery liquid-infused porous surface(s) formed by Liquid B can remain functional.

Solidification Temperature

In certain embodiments, Liquid B has a low freezing temperature, such as less than −5° C., −25° C., or even less than −80° C. Having a low freezing temperature will allow Liquid B to maintain its slippery behavior at reduced temperatures and to repel a variety of liquids or solidified fluids, such as ice and the like, for applications such as anti-icing surfaces.

Evaporation Rate

In certain embodiments, Liquid B can have a low evaporation rate, such as less than 1 nm/s, less than 0.1 nm/s, or even less than 0.01 nm/s. Taking a typical thickness of Liquid B to be about 10 μm and an evaporation rate of about 0.01 nm/s, the surface can remain highly liquid-repellant for a long period of time without any refilling mechanisms.

In certain embodiments, the lifetime of the surface can be further extended by using a self-refilling mechanism as described above with reference to FIGS. 9A to 9D and FIG. 10.

Viscosity of Liquid B

Experimentally, it is observed that Liquid A can become highly mobile on the surface of Liquid B when the kinematic viscosity of Liquid B is less than 1 cm$^2$/s. Since liquid viscosity is a function of temperature (i.e., liquid viscosity reduces with increasing temperature), choosing the appropriate lubricant that operates at the aforementioned viscosity (i.e., <1 cm$^2$/s) at specific temperature range is desirable. Particularly, various different commercially available Liquid B can be found at the specified viscosity, such as perfluorinated oils (e.g., 3M™ Fluorinert™ and DuPont™ Krytox® oils), at temperatures ranging from less than −80° C. to greater than 260° C. For example, the temperature dependence of liquid viscosity of DuPont Krytox oils is shown in the Table A as a specific example (note: data is provided by the manufacturer of DuPont Krytox oils).

TABLE A

Temperature dependence of liquid viscosity of DuPont Krytox Oils.

| Temperature (° C.) | Viscosity (cm²/s) | | | | | | | |
|---|---|---|---|---|---|---|---|---|
| | Krytox 100 | Krytox 101 | Krytox 102 | Krytox 103 | Krytox 104 | Krytox 105 | Krytox 106 | Krytox 107 |
| 20 | 0.124 | 0.174 | 0.38 | 0.82 | 1.77 | 5.22 | 8.22 | 15.35 |
| 40 | 0.055 | 0.078 | 0.15 | 0.30 | 0.60 | 1.60 | 2.43 | 4.50 |
| 100 | — | 0.02 | 0.03 | 0.05 | 0.084 | 0.18 | 0.25 | 0.42 |
| 204 | — | — | — | — | — | 0.031 | 0.041 | 0.06 |
| 260 | — | — | — | — | — | — | 0.024 | 0.033 |

The viscosities of both Liquid A (the one repelled) and B (infusing) both have an effect on the performance of slippery liquid-infused porous surface(s). Because the liquid repellency of slippery liquid-infused porous surface(s) is conferred by the presence of the Liquid B, the viscosity of Liquid B can affect the physical characteristics of liquid repellency of slippery liquid-infused porous surface(s), such as the velocity of Liquid A. The more viscous the Liquid B the less mobile the given Liquid A is.

Figure 36:
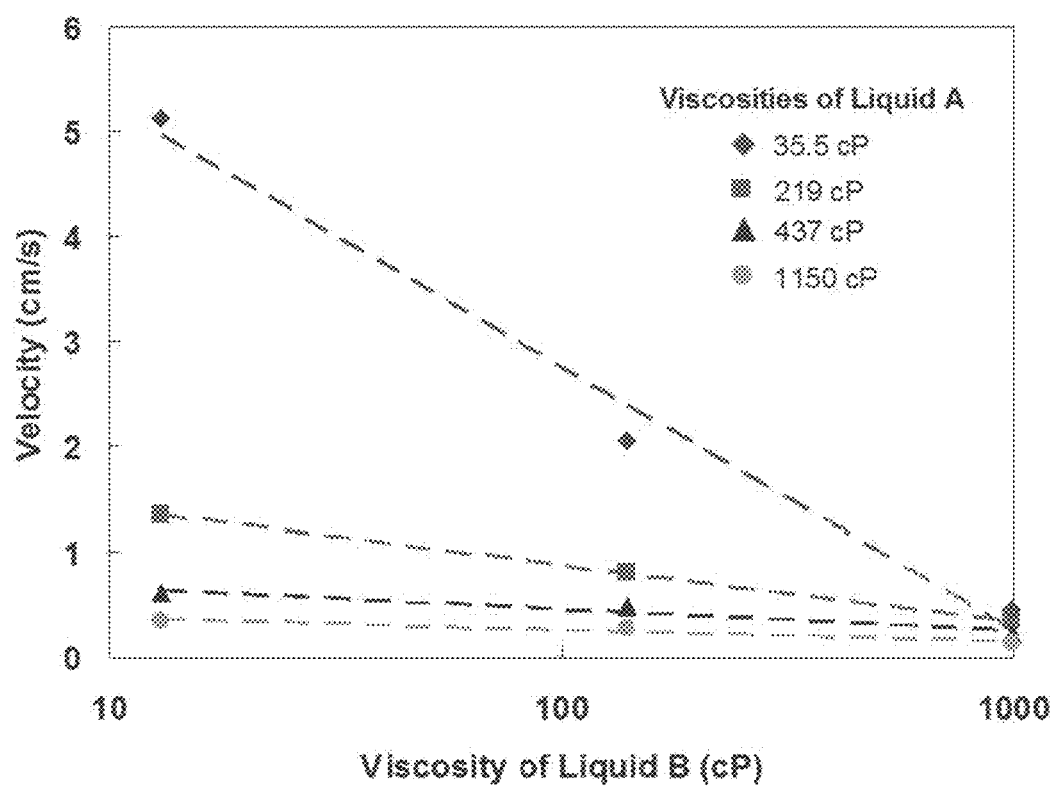
FIG. 36 is a graph showing the dependence of liquid repellency of slippery liquid-infused porous surface(s) on the viscosity of Liquid (here, Krytox 100, 103, and 105 (DuPont)). For constant viscosity of Liquid A (here, 25 µL of glycerol), Liquid A's mobility increases as the viscosity of Liquid B decreases. Likewise, for constant viscosity of Liquid B, the mobility of Liquid A increases with reducing viscosity of Liquid A. These results indicate that viscous dissipation plays a major role in the liquid mobility of slippery liquid-infused porous surface(s)

For a Liquid A of constant viscosity, its velocity on slippery liquid-infused porous surface(s) reduces with increasing viscosity of Liquid B. For example, referring to FIG. 36, for a 50 μL of Liquid A of absolute viscosity of 1 cP, its velocities on slippery liquid-infused porous surface(s) with Liquid B of viscosities of 13 cP, 140 cP, and 990 cP are ~17 cm/s, ~5.8 cm/s, and ~0.98 cm/s, respectively. Therefore, to enhance the velocity of Liquid A on slippery liquid-infused porous surface(s), it is desirable to use a Liquid B having a lower viscosity. This general trend is consistent for Liquid A of viscosities ranging from 1 cP to 1000 cP.

High Temperature Omniphobicity

Surface coatings that are capable of repelling high temperature fluids are important, e.g., for fuel transport and district heating systems. Since surface tensions of fluids reduce with increasing temperature, the development of surface coatings that repel fluids at high temperatures is very challenging. Thus, it is important to be able to characterize the liquid repellency performance of slippery liquid-infused porous surface(s) at various temperatures.

Figure 21:
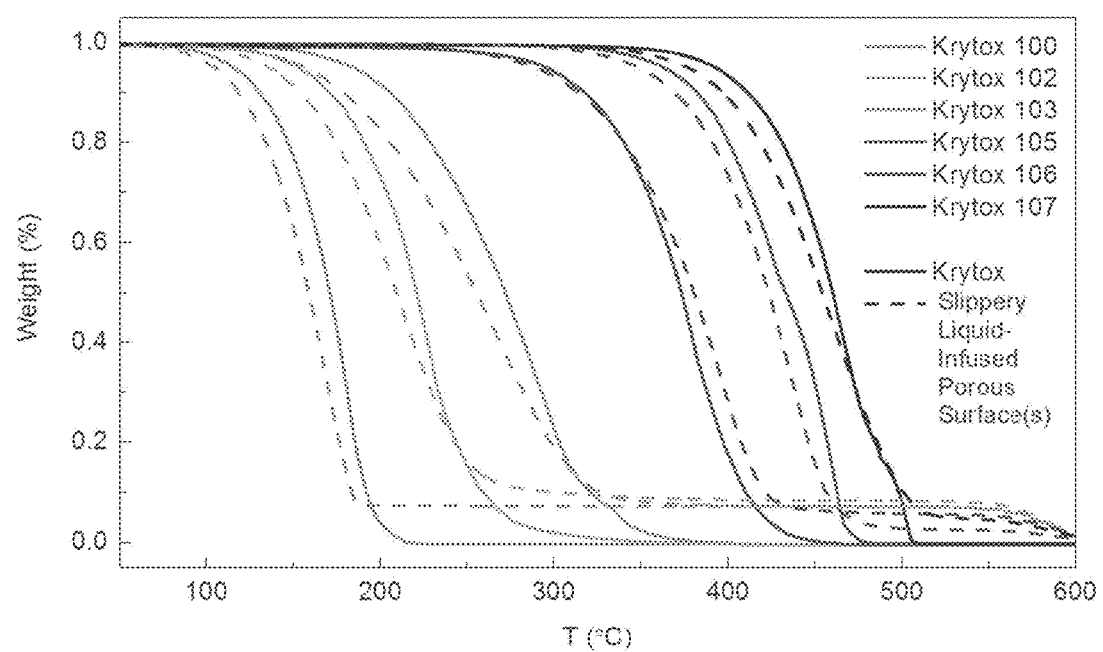
FIG. 21 is a thermogravimetric analysis of commercially available lubricants and the resulting slippery liquid-infused porous surface(s), indicating the high temperature stability of the repellent materials over 200° C.
Figure 37:
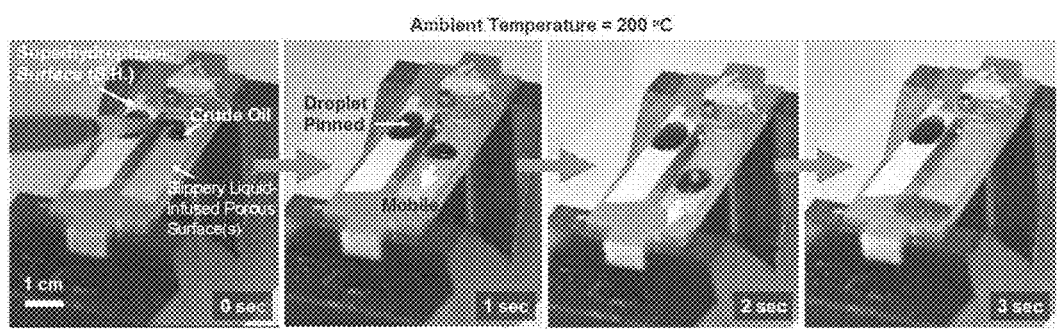
FIG. 37 is a series of photographs demonstrating high temperature transport of crude oil on slippery liquid-infused porous surface(s). The crude oil droplet remains pinned on the superhydrophobic surface, but is highly mobile on the slippery liquid-infused porous surface(s) at ambient temperatures of up to 200° C.

Because slippery liquid-infused porous surface(s) consists of two components—Liquid B and the porous or roughened solid—the temperature stability of slippery liquid-infused porous surface(s) is highly dependent upon the choice of Liquid B and the substrate. Commercially available Liquid Bs have varying liquid viscosities and therefore allow slippery liquid-infused porous surface(s) to repel material at various temperatures (see Table A). Thermogravimetric analysis can be used to assess the temperature stability of slippery liquid-infused porous surface(s). As shown in FIG. 21, Teflon/Krytox-based slippery liquid-infused porous surface(s) remained stable over a range of 200° C., depending upon the Liquid B used. Additionally, slippery liquid-infused porous surface(s) is capable of repelling a broad range of crude oils at a temperature exceeding 200° C. (see FIG. 37).

Film Thickness

Liquid B can be deposited to any desired thickness. Thickness of Liquid B on the order of the surface roughness peak-to-valley distance of the porous substrate provides good liquid-solid interaction between the substrate and Liquid B. When the solid substrate is tilted at a position normal to the horizontal plane, liquid layer with thickness below a characteristic length scale can maintain good adherence to the roughened surface, whereas liquid layers above the characteristic length can flow, creating flow lines (surface defects) and disrupting the flatness of the fluid surface. For example, non-limiting thicknesses for the fluid layer (as measured from the valleys of the roughened surface are on the order of 5-20 μm when the peak to valley height is ~5 μm.

Application of Liquid B

In certain embodiments, Liquid B can be applied by pipetting drops of the liquid onto the roughened surface, or by dipping the roughened surface into a reservoir carrying Liquid B. In some embodiments, Liquid B can be flushed over the roughened surface (e.g. in tubes and pipes). In some embodiments, Liquid B can be sprayed or otherwise spread onto the roughened surface. Liquid B and the roughened surface can be both generated by a double-spraying process, where emulsions consisting of nano/microparticles are first sprayed onto a flat solid surface to form a substantially roughened solid layer, and then Liquid B can be sprayed onto this freshly formed layer for further infiltration. In addition, Liquid B may infiltrate into the pores of the roughened surface by capillary action and form an ultra-smooth film on top of the roughened surface. In certain embodiments, when sufficient quantity of Liquid B is provided, Liquid B may wet the entire roughened surface structure and form an ultra-smooth film over the underlying roughened surface.

Combination of Liquid B and Roughened Surface

Any suitable combination of the roughened surface and Liquid B described above can be employed. Some particular characteristics during selection of the combination of Liquid B and the roughened surface can provide additional features that may be desirable in certain applications.

Durability of Slippery Liquid-Infused Porous Surface(s)

The durability of slippery liquid-infused porous surface(s) may be dependent on the lifetime of the Liquid B within the roughened surface. The lifetime of Liquid B may be a function of the vapor pressure of the liquid, which depends on the chemical composition of the fluid (see Table B). Fluid viscosity can also play a role. In general, the higher is the viscosity of Liquid B, the longer is its lifetime.

TABLE B

Chemical and physical properties of the perfluorinated fluids.

| Trade Name | Chemical Composition | Kinematic Viscosity | Evaporate Rate (% weight/day) |
|---|---|---|---|
| 3M ™ Fluorinert ™ FC-70 | perfluorotri-n-pentylamine | 0.12 cm²/s at 25° C. | 9.13 |

TABLE B-continued

Chemical and physical properties of the perfluorinated fluids.

| Trade Name | Chemical Composition | Kinematic Viscosity | Evaporate Rate (% weight/day) |
|---|---|---|---|
| Dupont ™ Krytox ® 100 | Perfluoropolyethers | 0.12 cm$^2$/s at 20° C. | 0.59 |
| Dupont ™ Krytox ® 103 | Perfluoropolyethers | 0.82 cm$^2$/s at 20° C. | <0.05 |

In addition, as noted above, one of the advantages of using porous membrane is that Liquid B could be continuously replenished through capillary wicking by placing a liquid reservoir underneath or next to the membrane. Various reservoir designs can be implemented depending on a specific application, as discussed with respect to FIG. 10. If an application requires operation within a defined time frame, then a fixed amount of lubricant can be incorporated within the reservoir based on the measured evaporation rates of the lubricants.

To estimate typical lifetimes, the evaporation rates for the perfluorinated liquids (i.e., FC-70 and Krytox® oils, see FIGS. 12A-12C) were measured. The evaporation data were measured under ambient conditions (i.e., 22±1° C. with 53±5% relative humidity) when Liquid B is incorporated within the porous solid to reflect the actual operating conditions. A reservoir with a fixed amount of perfluorinated fluid is connected to slippery liquid-infused porous surface(s) during the measurement (see FIGS. 12A-12C). Specifically, the measured evaporation rates for FC-70, Krytox® 100, and Krytox® 103 are 9.13%/day, 0.59%/day, and <0.05%/day, respectively (see FIG. 12B), indicating that if the chemical composition and viscosity of the liquid are chosen appropriately, the evaporation rate of the lubricant can be minimized. Based on these measurements, approximately ~550 xm thick Krytox® 103 may be needed for the continuous operation of slippery liquid-infused porous surface(s) on the order of years (assuming the wetting performance begins to degrade after a 30% mass loss, as indicated by the measurements with FC-70, shown in FIG. 12C). In addition, it is experimentally observed that slippery liquid-infused porous surface(s) (with porous Teflon and Krytox 100) remains highly functional after being submerged under immiscible fluid environments, such as water, for more than 3 months.

Self-Healing Characteristics

Figure 13A:
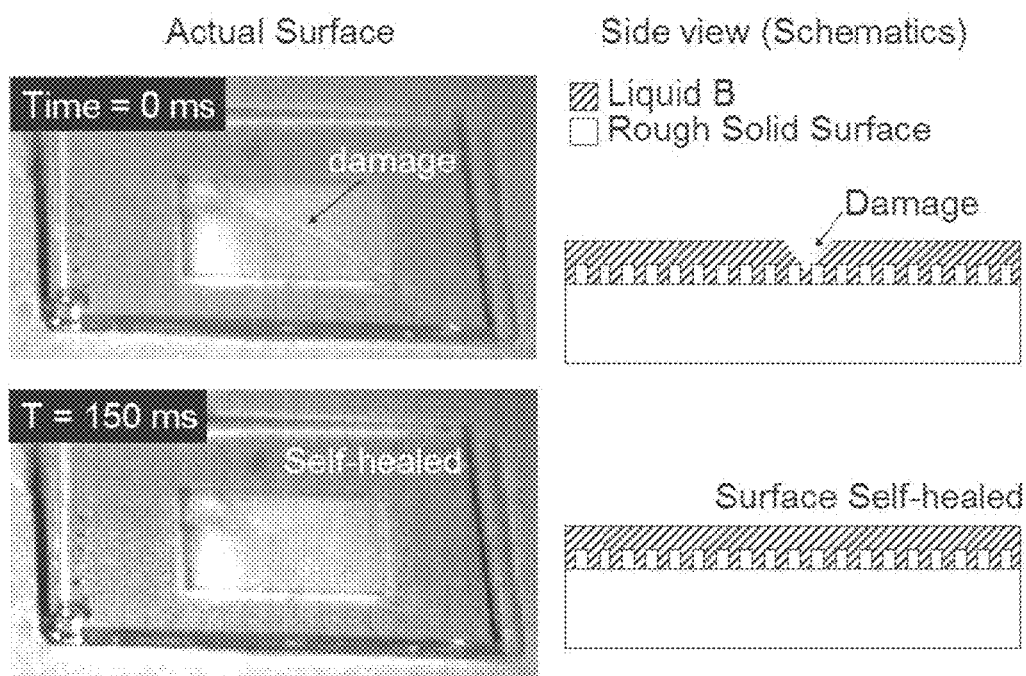
FIG. 13A shows images of slippery liquid-infused porous surface(s) demonstrating self-healing properties, where the self-healing time scale is on the order of 100 ms in accordance with certain embodiments.
Figure 13B:
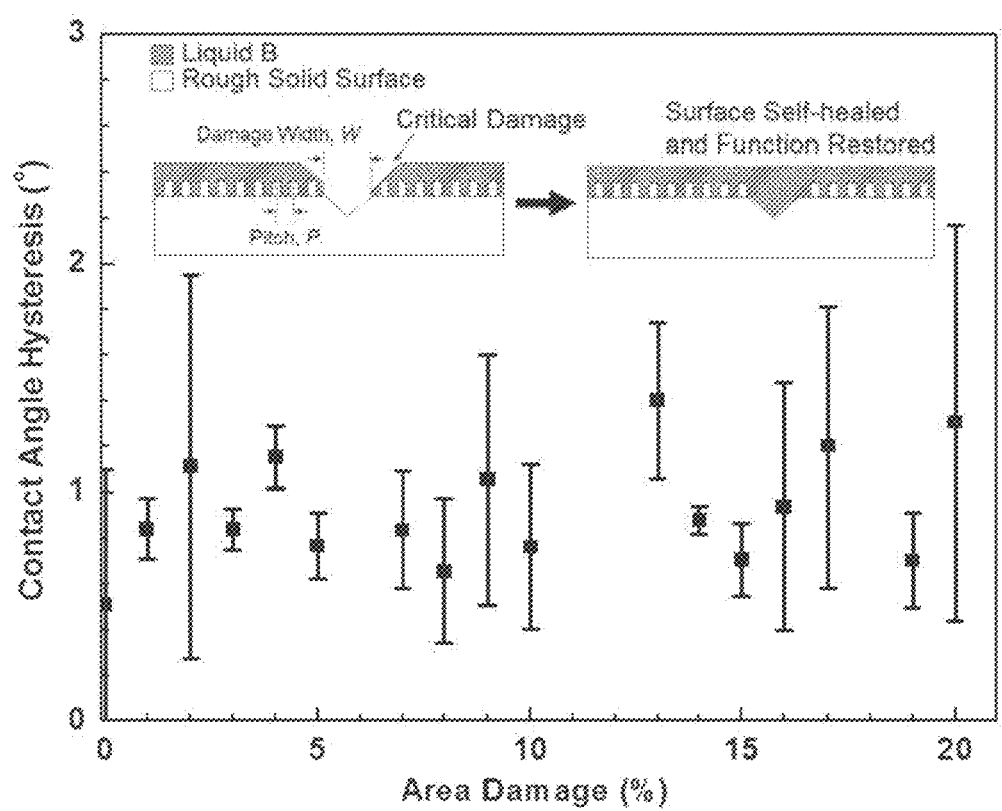
FIG. 13B is a chart showing restoration of liquid repellency function after critical physical damages (Test liquid=decane, $\gamma_{LV}$=23.6±0.1 mN/m) in accordance with certain embodiments.

In certain embodiments, Liquid B and the roughened surface can be selected so that they have fast self-healing properties. As used herein, "self-healing" refers to re-formation of an ultra-smooth (and even substantially molecularly flat) surface after physical impact (e.g., damage). For example, the surface may be able to self-heal on a time scale that is faster than 100 s, 10 s, 1 s, or even 100 ms. The self-healing behavior of the liquid repellant surfaces can be a function of the interaction between Liquid B and the roughened surface, thickness of the film, as well as the viscosity of the Liquid B. Typical kinematic viscosities of Liquid B are in the range of 0.10 cm$^2$/s to 10 cm$^2$/s. Referring to FIGS. 13A and 13B (described in greater detail in EXAMPLE 1 below), particle impact or scratching can damage the surface by, for example, breaking or removing the topological features of the surface in a small area. Typically the impact can also displace Liquid B, resulting in a scratch or pit and exposing the substrate surface. Due to the wicking capability and good wetting properties of Liquid B, however, the liquid layer can flow back to refill the pit or scratch and to regenerate the smooth fluid surface. A reservoir with extra fluid can be available to 'top off' the fluid layer thickness to maintain the desired thickness.

FIGS. 13C and 13D show time-lapse images of slippery liquid-infused porous surface(s) (FIG. 13C) as compared to a typical hydrophobic flat surface (FIG. 13D) after physical damage. In the images, the dotted line depicts the location where a physical damage was made by scratching the respective surfaces with a blade. As shown in FIG. 13D, after damage, oil remains pinned at the damage site for typical hydrophobic flat surface at tilting angles greater than 10° and even after 17 seconds. In contrast, as shown in FIG. 13C, slippery liquid-infused porous surface(s) heals itself in less than two seconds (i.e., the time it took oil to traverse past the damage site at 5° tilting angle) and oil continues to roll past the damage site for slippery liquid-infused porous surface(s) as if physical damage was never made.

Refractive Index Matching

In certain embodiments, the roughened surface and Liquid B can be selected as to promote enhanced transparency at desired wavelengths. For example, the roughened surface and Liquid B can be selected to have similar refractive indices so that the combination of roughened surface and Liquid B forms a transparent material in wavelengths, such as visible, infrared, or even UV wavelengths.

As used herein, "similar indices of refraction" means to have indices of refraction which can be differed from each other at least by ~0.3. In certain embodiments, due to their substantially similar indices of refraction, slippery liquid-infused porous surface(s) can be substantially transparent in desired ranges of wavelengths (e.g., UV, visible, infrared, and the like wavelengths), such as more than 70%, 80%, 90% or even 95% transparent.

Figures 14A, 14B:
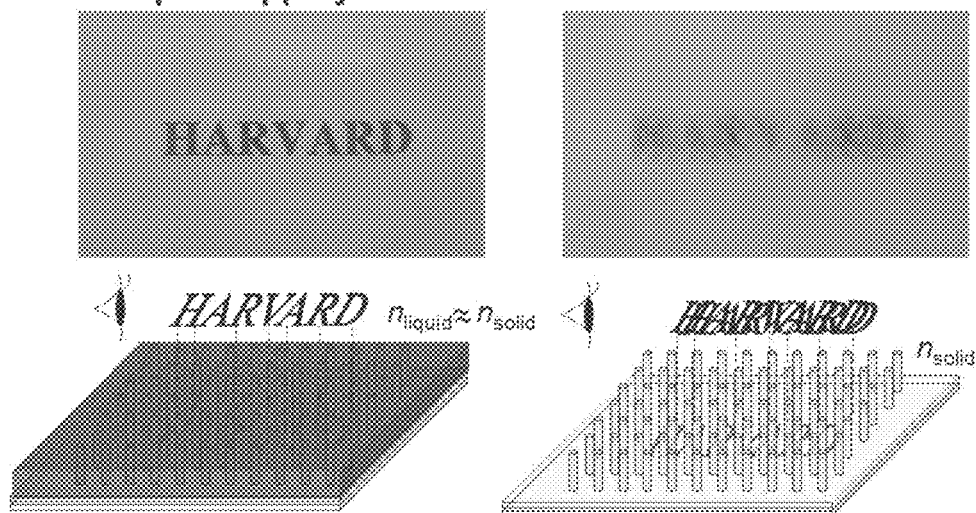
FIGS. 14A and 14B show images of the surface of the present disclosure demonstrating enhanced optical transparency of the (A) liquid-slippery surface (slippery liquid-infused porous surface(s)) as compared to the regular (B) nanostructured surface in visible light range in accordance with certain embodiments.

For example, FIG. 14A shows a substantially transparent slippery liquid-infused porous surface(s) as compared the roughened surface alone that is shown in FIG. 14B. In FIG. 14B, the high aspect ratio surface at a solid/air interface (e.g., typically having different refractive indices) results in significant light scattering, thereby reducing light transmission. In contrast, as shown in FIG. 14A, by matching their indices of refraction, light scattering can be reduced and light transmission can be improved. For example, by utilizing materials that have similar indices of refraction and have a clear, transparent property, a surface having substantially transparent characteristics can be formed. Additionally, the optical transparency of the surface is minimally affected even after physical scratching (i.e., scratch-resistant) due to the aforementioned self-healing property.

Figure 14C:
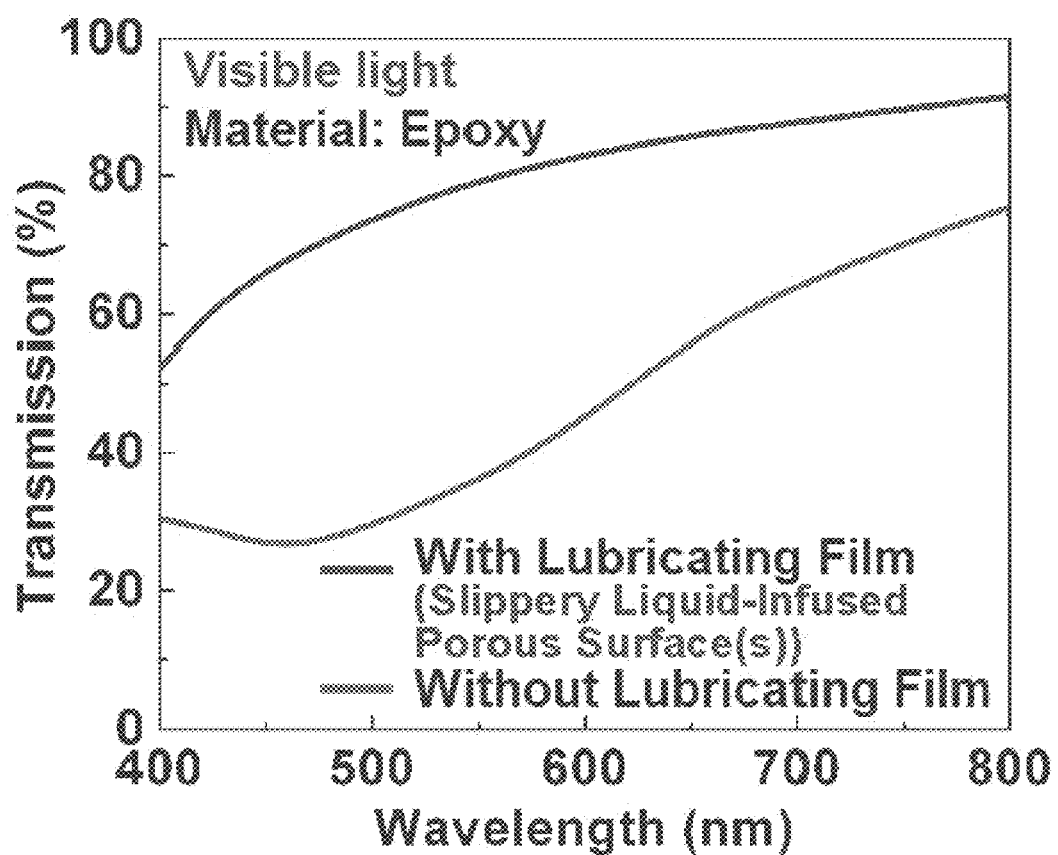
FIG. 14C shows optical transmission measurements for epoxy-resin-based slippery liquid-infused porous surface(s) in the visible light range (400-800 nm) in accordance with certain embodiments.

FIG. 14C shows the optical transmission measurement for an epoxy-resin-based slippery liquid-infused porous surface(s) showing higher transmission across the entire visible light wavelengths (400-800 nm) as compared to the epoxy-resin substrate without the Liquid B.

FIGS. 15A to 15C show near infrared range wavelength schematics and images (i.e., wavelength >800 nm) at 50° C. (FIG. 15B) and −20° C. (FIG. 15C) of a metal block, "H", that was placed on top of a temperature-controlled plate (left), with a dry porous membrane placed over the "H" (center) and, with a porous membrane wetted with perfluorinated liquid as Liquid B (right) placed over the "H" (right). As shown, whereas the porous membrane without any Liquid B infiltrated therein scatters near-infrared wavelengths, slippery liquid-infused porous surface(s) having a porous membrane and Liquid B infiltrated therein is transparent to near-infrared wavelengths.

Figure 15D:
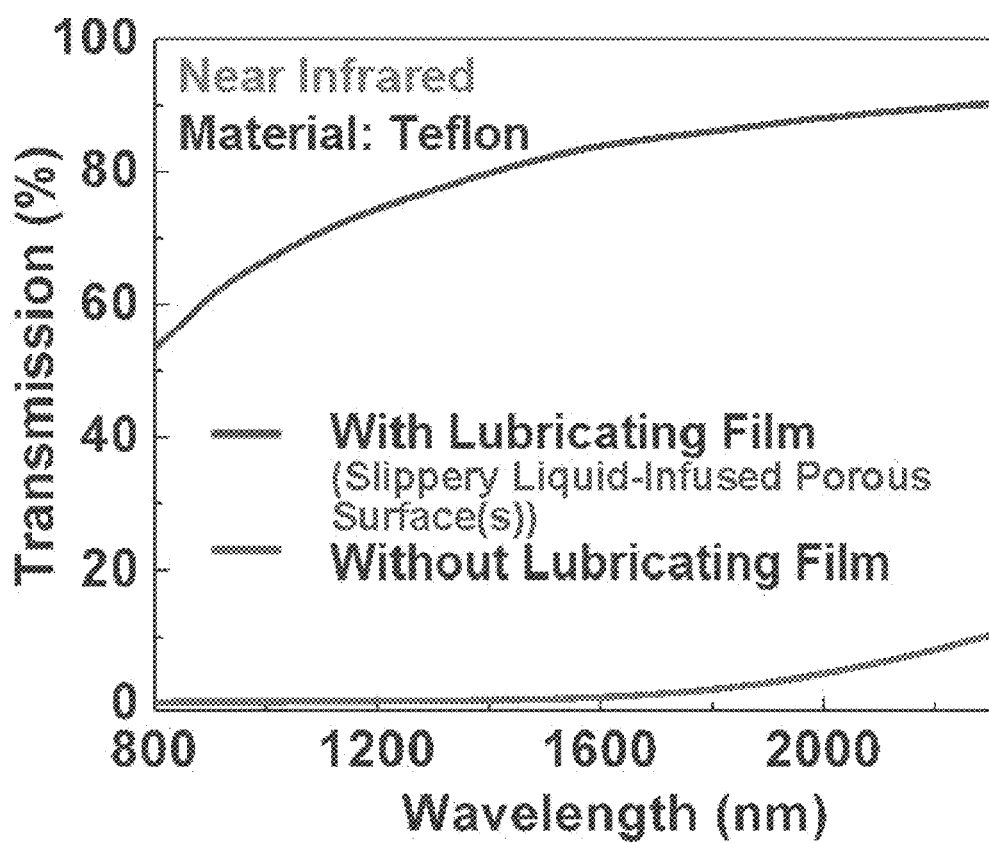
FIG. 15D shows optical transmission measurements for a Teflon-based slippery liquid-infused porous surface(s) in the near infrared range (800-2300 nm) in accordance with certain embodiments.

FIG. 15D shows the optical transmission measurement for a Teflon-based slippery liquid-infused porous surface(s) showing higher transmission across the entire near-infrared wavelengths (800-2300 nm) as compared to the Teflon substrate without the Liquid B.

Surface Energy Considerations

In certain embodiments, the roughened surface may be functionalized so that the critical surface energy of the roughened surface is higher than the surface energy of Liquid B; under these conditions, complete wetting of Liquid B can spontaneously occur throughout the roughened surface.

In certain embodiments, Liquid B has a surface energy that is less than the surface energy of the roughened surface. In general, when the surface energy of Liquid B is lower than the surface energy of the underlying roughened surface, it tends to wet the solid well. More precisely, the spreading of a liquid depends on the spreading parameter (S), where $S=[E_{substrate}]_{dry}-[E_{substrate}]_{wet}=\gamma SO-(\gamma SL+\gamma)$ ($\gamma SO$, $\gamma SL$, $\gamma$: the surface energy of at the solid/air, solid/liquid, and liquid/air interfaces, respectively.) The liquid wets a surface completely if S>0 when the drop partially wet a surface if S<0. (See, e.g., P.-G. de Gennes, F. Brochard-Wyart, D. Quere, Capillarity and Wetting Phenomena: drops, bubbles, pearls, waves, Springer (New York, N.Y.), 2004, the contents of which is incorporated by reference herein in its entirety). Thus, in certain embodiments, the surface energy of the Liquid B is such that the spreading parameter S is positive.

In certain embodiments, the critical surface energy of the flat surface (i.e., $\gamma_{c-S}$) may be comparable or lower than the surface tension of Liquid B (i.e., $\gamma_{LV-B}$). For example, the critical surface energy of the roughened surface may be at least 1.25 times lower than the surface tension of Liquid B. In certain embodiments, when the critical surface energy of the flat surface is lower than the surface energy of Liquid B, the flat surface may be provided with a high degree of roughness to promote wetting of Liquid B within the pores of the roughened surface.

In certain embodiments, Liquid B and/or the roughened surface can be modified to obtain the desired surface energy and/or critical surface energy. For example, a perfluorinated liquid as Liquid B and a nanostructured surface made out of polymer (for example, epoxy resin, silicone, and Teflon) that is chemically functionalized with end-functional group of —$CF_3$ or other similar fluorocarbon groups can be utilized as the roughened surface.

Other materials including sapphire, diamonds, silicon, glass, and metals (e.g., aluminum) can be also used with suitable chemical functionalization schemes. Surface coating can be achieved by methods well known in the art, including plasma assisted chemical vapor deposition, chemical functionalization, solution deposition, layer deposition, vapor deposition, mechanical, and electro-chemical methods. For example, surfaces containing hydroxyl groups (i.e., —OH) can be functionalized with various commercially available fluorosilanes (e.g., tridecafluoro-1,1,2,2-tetrahydrooctyl-trichlorosilane, heptadecafluoro-1,1,2,2-tetra-hydrodecyl trichlorosilane, etc.). In certain embodiments, many materials having native oxides, such as silicon, glass, and alumina, can be activated to contain —OH functional groups using techniques such as plasma treatment. After activation, either vapor or solution deposition techniques can be used to attach silanes or other surface modifiers so that surfaces with low surface energy can be produced. For vapor deposition, the deposition can be carried out by exposing the surface with silane vapors. For solution deposition, the deposition can be carried out by immersing the surface into a solution of a silane or other surface modifier, followed by appropriate rinsing and drying after deposition. Examples of other surface modifiers include, but are not limited to, long-chain perfluorinated carboxylic acids (e.g., perfluorooctadecanoic acid and other homologues), fluorinated phosphonic and sulfonic acids, fluorinated silanes, end-functionalized fluorinated polymers, such as DuPont Krytox series of surfactants (like Krytox 157 FSL, FSM, FSH) and combinations thereof. The chains of the surface modifier molecules can be linear or branched and they can be only partially fluorinated. The solution treatment can be done at a desired temperature depending on the reactivities and other properties of the modifying molecules and surfaces to be modified. A variety of solvents of different solubilizing properties, volatilities and boiling points can be used for the surface modifications. In addition to simple immersing, the solution modification can be done by exposing the surface to refluxing the solution of the modifier, or by continuously spraying it onto the surface, or pumping/recirculating the solution through the pipe whose surface needs to be modified, or any other appropriate way of bringing the surface and the modifier solution in contact. For layered deposition, layered deposition of a primer is followed by application of a mixture of sacrificial beads and Liquid B, which is dried and cured. The beads are removed to produce a contiguous porous Teflon-like surface.

In some other embodiments, where hydroxyl groups is absent on the surface, the surface can be first coated with thin films of metals, such as gold or platinum, and the thin metal films can be functionalized with various commercially available thiols of low surface energy (e.g., heptane thiol, perfluorodecanethiol, etc.). Similarly, vapor or solution deposition techniques can be carried out similar to that describe for silane deposition using, for example, alkane thiol solutions.

Generally, it may be important to have the chemical nature between the roughened solid and the Liquid B be similar. For example, non-polar Liquid B with fluorocarbon functional groups may adhere well with roughened solid surface that is functionalized with fluorocarbon groups (e.g., —$CF_3$, —$CF_2$). In another example, polar Liquid B may adhere well with roughened solid surface that is functionalized with hydroxyl groups (i.e., —OH).

Reactivity Between Liquid B and Roughened Surface

The roughened surface material can be selected to be chemically inert to Liquid B and to have good wetting properties with respect to Liquid B. In certain embodiments, Liquid B (and similarly Object A) may be non-reactive with the roughened surface. For example, the roughened surface and Liquid B (or Object A) can be chosen so that the roughened surface does not dissolve upon contact with Liquid B (or Object A). In particular, perfluorinated liquids (Liquid B) work exceptionally well to repel a broad range of polar and non-polar Liquids A and their solidified forms, such as hydrocarbons and their mixtures (e.g., from pentane up to hexadecane and mineral oil, paraffinic extra light crude oil; paraffinic light crude oil; paraffinic light-medium crude oil; paraffinic-naphthenic medium crude oil; naphthenic medium-heavy crude oil; aromatic-intermediate medium-heavy crude oil; aromatic-naphthenic heavy crude oil, aromatic-asphaltic crude oil, etc.), ketones (e.g., acetone, etc.), alcohols (e.g., methanol, ethanol, isopropanol, dipropylene glycol, ethylene glycol, and glycerol, etc.), water (with a broad range of salinity, e.g., sodium chloride from 0 to 6.1 M; potassium chloride from 0 to 4.6 M, etc.), acids (e.g., concentrated hydrofluoric acid, hydrochloric acid, nitric acid, etc) and bases (e.g., potassium hydroxide, sodium hydroxide, etc), soap water, detergent, surfactant-rich solutions, frost, and ice, etc.

Wettability of Liquid B

In addition, the roughened surface topographies can be varied over a range of geometries and size scale to provide the desired interaction, e.g., wettability, with Liquid B. In certain embodiments, the micro/nanoscale topographies underneath the Liquid B can enhance the liquid-wicking property and the adherence of Liquid B to the roughened surface. As a result, the Liquid B can uniformly coat the roughened surface and get entrapped inside at any tilting angles.

Combination of Object A and Liquid B
Immiscibility

In certain embodiments, Object A (i.e., the test liquid) and Liquid B (i.e., the functional liquid layer) may be immiscible. For example, the enthalpy of mixing between Object A and Liquid B may be sufficiently high (e.g., water and oil) that they phase separate from each other when mixed together.

In certain embodiments, Liquid B can be selected such that Object A has a small or substantially no contact angle hysteresis. Liquid B of low viscosity (i.e., <1 cm$^2$/s) tends to produce surfaces with low contact angle hysteresis. For example, contact angle hysteresis less than about 5°, 2.5°, 2°, or even less than 1° can be obtained. Low contact angle hysteresis encourages test Object A sliding at low tilt angles (e.g., <5°), further enhancing liquid repellant properties of the surface.

Density of Object A and Liquid B

In certain embodiments, the density of Object A may be lower than that of the Liquid B. For example, density of Object A may be at least ~1.5 times lower than that of Liquid B.

In certain embodiments, the density of Object A may be higher than that of the Liquid B if Object A is smaller than its capillary length in its liquid form.

Surface Energy

In certain embodiments, the critical surface energy of the Liquid B ($\gamma_{c-B}$) may be lower than the surface energy of Object A (i.e., $\gamma_{LV-A}$) (i.e., $\gamma_{LV-A} > \gamma_{c-B}$). For example, the critical surface energy of Liquid B may be at least 1.05 times lower than the surface energy of Object A.

Solidification Temperature

In certain embodiments, the solidification temperature of Liquid B may be lower than that of Object A. In certain embodiments, Liquid B can maintain its liquid state below the solidification temperature of Object A, thereby retaining its slippery property. Without wishing to be bound by theory, there may be at least two reasons to maintain Liquid B in a liquid state even while Object A solidifies.

First, having Liquid B maintained in the liquid state may result in reduced adhesion at the interface between Solid A and Liquid B in the directions normal and tangential to the substrate surface, as compared to that of the interface between Solid A and other solid surfaces (i.e., roughened surfaces). Adhesion between surfaces may be proportional to the contact surface area, where the smoothness of Liquid B surface can minimize contact area between Solid A and Liquid B, due to the smaller surface area at the interface compared to a roughened surface. The reduced adhesion may facilitate removal of Solid A from Liquid B surface at much reduced force per unit area.

Second, the ultra-smooth surface of Liquid B may also reduce the condensation of Object A from the air (i.e., assuming the vaporized form of Object A is present in air) when the surface of Liquid B is cooled to the temperature below the solidification temperature of Object A. This may be due to the fact that there are few or even no nucleation sites on the Liquid B surface, which greatly reduce the nucleation probability of Object A. As a result, the formation of fog and frost (i.e., solidified form of Object A at the micro- and nanoscale) on the surface can require more stringent conditions (e.g., lower temperature or a higher vapor pressure of Object A in the air) as compared to the other solid surfaces. To maintain Liquid B in the liquid state, the solidification temperature of Liquid B may be lower, e.g., 5-150° C. lower than that of Object A at atmospheric pressure.

Boiling Temperature

In certain embodiments, the boiling temperature of Liquid B may be higher than the solidification temperature of Object A. In certain embodiments, Liquid B may be able to maintain its liquid state above the solidification temperature of Object A. Additionally, maintaining the liquid state may facilitate the removal of Object A from the Liquid B surface due to the aforementioned liquid-slippery function, while the surface is held at a temperature above the solidification temperature of Object A. This may be particularly important for applications in surface defrosting, where Liquid B may be defrosted using minimal energy input (e.g., at a lower temperature) as compared to other solid surfaces. To maintain Liquid B in the liquid state, the boiling temperature of Liquid B may be higher, e.g., 25-250° C. higher than the solidification temperature of Object A at atmospheric pressure.

Combination of Roughened Surface, Object A and Liquid B

In certain embodiments, Object A, Liquid B, and the roughened surface may be selected so that the roughened surface has a greater affinity towards Liquid B as compared to that of Object A. The roughened surface can be chosen such that the roughened surface is wetted preferentially by Liquid B rather than by Object A.

Referring to equations (e2) and (e3) noted above, satisfying both (e2) and (e3) has generally shown to provide a stable lubricating film formation. In contrast, when neither (e2) nor (e3) are satisfied, Liquid B is generally observed to be displaced by Object A. In the case where only one of the conditions shown in (e2) or (e3) is satisfied, Liquid B may or may not be displaced by Object A. A number of different solid/Liquid-A/Liquid-B combinations have been tested and the results are compared with (e2) and (e3). As shown in Table 1 below, these relationships agree favorably with all of the experimental conditions in different scenarios.

TABLE 1

Comparison of the Governing Relationships with Experimental Observations for Various Solid-Liquid-A-Liquid-B Combinations

| Solid | Liquid A | Liquid B | R | $\gamma_A$ | $\gamma_B$ | $\gamma_{AB}$ | $\theta_A$ | $\theta_B$ | $\Delta E_0$ | $\Delta E_1$ | $\Delta E_2$ | Stable Film? Theory | Stable Film? Exp. |
|---|---|---|---|---|---|---|---|---|---|---|---|---|---|
| S. Epoxy | H$_2$O | FC-70 | 2 | 72.4 | 17.1 | 56.0 | 113.1 | 14.1 | 45.0 | 34.0 | 145.3 | Y | Y |
| S. Epoxy | C$_{16}$H$_{34}$ | FC-70 | 2 | 27.2 | 17.1 | 8.2 | 70.5 | 14.1 | 7.5 | 6.8 | 25.1 | Y | Y |
| S. Epoxy | C$_{13}$H$_{28}$ | FC-70 | 2 | 25.9 | 17.1 | 7.7 | 63.5 | 14.1 | 5.0 | 2.4 | 18.9 | Y | Y |
| S. Epoxy | C$_{10}$H$_{22}$ | FC-70 | 2 | 23.6 | 17.1 | 6.7 | 60.0 | 14.1 | 4.8 | 2.9 | 16.1 | Y | Y |
| S. Epoxy | C$_8$H$_{18}$ | FC-70 | 2 | 21.4 | 17.1 | 4.4 | 50.7 | 14.1 | 3.0 | 1.7 | 10.4 | Y | Y |

TABLE 1-continued

Comparison of the Governing Relationships with Experimental Observations for Various Solid-Liquid-A-Liquid-B Combinations

| Solid | Liquid A | Liquid B | R | $\gamma_A$ | $\gamma_B$ | $\gamma_{AB}$ | $\theta_A$ | $\theta_B$ | $\Delta E_0$ | $\Delta E_1$ | $\Delta E_2$ | Stable Film? Theory | Exp. |
|---|---|---|---|---|---|---|---|---|---|---|---|---|---|
| S. Epoxy | $C_6H_{14}$ | FC-70 | 2 | 18.6 | 17.1 | 2.6 | 40.1 | 14.1 | 2.4 | 2.1 | 6.2 | Y | Y |
| S. Epoxy | $C_5H_{12}$ | FC-70 | 2 | 17.2 | 17.1 | 2.5 | 30.8 | 14.1 | 1.8 | 1.1 | 3.7 | Y | Y |
| Epoxy | $H_2O$ | FC-70 | 2 | 72.4 | 17.1 | 56.0 | 92.6 | 33.5 | 17.5 | −20.9 | 90.4 | Y/N | Y |
| Epoxy | $C_{16}H_{34}$ | FC-70 | 2 | 27.2 | 17.1 | 8.2 | 30.6 | 33.5 | −9.2 | −26.5 | −8.2 | N | N |
| Epoxy | $C_{13}H_{28}$ | FC-70 | 2 | 25.9 | 17.1 | 7.7 | 26.9 | 33.5 | −8.8 | −25.4 | −8.9 | N | N |
| Epoxy | $C_{10}H_{22}$ | FC-70 | 2 | 23.6 | 17.1 | 6.7 | 14.2 | 33.5 | −8.6 | −23.9 | −10.7 | N | N |
| Epoxy | $C_8H_{18}$ | FC-70 | 2 | 21.4 | 17.1 | 4.4 | 7.9 | 33.5 | −6.9 | −18.3 | −9.6 | N | N |
| Epoxy | $C_6H_{14}$ | FC-70 | 2 | 18.6 | 17.1 | 2.6 | 0 | 33.5 | −4.3 | −11.3 | −7.2 | N | N |
| Epoxy | $C_5H_{12}$ | FC-70 | 2 | 17.2 | 17.1 | 2.5 | 0 | 33.5 | −2.9 | −8.4 | −5.8 | N | N |
| Epoxy | $H_2O$ | FC-70 | 1 | 72.4 | 17.1 | 56.0 | 92.6 | 33.5 | 17.5 | −38.5 | 72.8 | Y/N | N |
| Epoxy | $C_{16}H_{34}$ | FC-70 | 1 | 27.2 | 17.1 | 8.2 | 30.6 | 33.5 | −9.2 | −17.4 | 0.9 | Y/N | N |
| Epoxy | $C_{13}H_{28}$ | FC-70 | 1 | 25.9 | 17.1 | 7.7 | 26.9 | 33.5 | −8.8 | −16.5 | 0.0 | Y/N | N |
| Epoxy | $C_{10}H_{22}$ | FC-70 | 1 | 23.6 | 17.1 | 6.7 | 14.2 | 33.5 | −8.6 | −15.3 | −2.1 | N | N |
| Silicon | $C_{16}H_{34}$ | $H_2O$ | 1 | 27.2 | 72.4 | 51.1 | 5.6 | 13.1 | 43.4 | −7.7 | −1.8 | N | N |
| Silicon | $C_{10}H_{22}$ | $H_2O$ | 1 | 23.6 | 72.4 | 50.8 | 5.0 | 13.1 | 47.0 | −3.8 | −1.8 | N | N |
| Silicon | $C_8H_{18}$ | $H_2O$ | 1 | 21.4 | 72.4 | 50.8 | 5.0 | 13.1 | 49.2 | −1.6 | −1.8 | N | N |
| Silicon | $C_6H_{14}$ | $H_2O$ | 1 | 18.6 | 72.4 | 50.9 | 5.0 | 13.1 | 52.0 | 1.1 | −1.8 | Y/N | N |
| Silicon | $C_5H_{12}$ | $H_2O$ | 1 | 17.2 | 72.4 | 51.0 | 5.0 | 13.1 | 53.4 | 2.4 | −1.8 | Y/N | N |
| PDMS | Water | PDMS | 1 | 72.4 | 21.3 | 43 | 110 | 5.0 | 46.0 | 3.0 | 97.1 | Y | Y |
| PP | Water | PDMS | 1 | 72.4 | 21.3 | 43 | 108 | 5.0 | 46.0 | 0.6 | 94.7 | Y | Y |
| PP | Water | PDMS | 2 | 72.4 | 21.3 | 43 | 108 | 5.0 | 43.6 | 44.2 | 138.3 | Y | Y |
| PTFE | Water | PDMS | 2 | 72.4 | 21.3 | 43 | 115 | 5.0 | 51.8 | 60.6 | 154.7 | Y | Y |

In Table 1, "Y" indicates that Liquid B forms a stable lubricating film, and does not get displaced by Object A; whereas "N" indicates that Liquid B is displaced by Object A.

PDMS stands for polydimethylsiloxane; PP stands for polypropylene; PTFE stands for polytetrafluoroethylene. Notice that the contact angles and interfacial tension values were obtained from the literature for the combinations of PDMS/Water/PDMS, PP/Water/PDMS, PTFE/Water/PDMS (see for example: Israelachvili, J. N. *Intermolecular and Surface Forces*, Academic Press, 2011; Schonhorn, H., *J. Phys. Chem.* 70, 4086, 1966; Gao, L. and McCarthy, T. J., *Langmuir* 24, 9183-9188, 2008; Kobayashi, H. and Owen, M. J., *Macromolecules* 23, 4929-4933, 1990; Chaudhury, M. K. and Whitesides, G. M., *Langmuir* 7, 1013-1025, 1991; Lillehoj, P. B., Wei, F., and Ho, C. M., *Lab Chip* 10, 2265-2270, 2010).

$\theta_A$ and $\theta_B$ are estimated from the measured static contact angles on flat substrates from at least three individual measurements (see Table 2).

R, $\gamma_A$, $\gamma_B$ represent the roughness factor of the substrate and the surface tensions of Object A and B, respectively (see Table 3).

TABLE 3

Measured Surface Tension for Various Polar and Non-Polar Liquids.

| Liquid | Surface Tension (mN/m) | n |
|---|---|---|
| Water | 72.4 ± 0.1 | 116 |
| Glycerol | 60.3 ± 1.1 | 35 |
| Ethylene Glycol | 48.1 ± 0.3 | 32 |
| Dipropylene Glycol | 32.3 ± 0.3 | 35 |
| Extra-light Crude Oil* | 27.0 ± 0.8 | 15 |
| Light Crude Oil** | 25.6 ± 0.9 | 15 |
| Hexadecane | 27.2 ± 0.2 | 31 |
| Tridecane | 25.9 ± 0.1 | 30 |
| Dodecane | 25.3 ± 0.1 | 32 |
| Undecane | 24.6 ± 0.2 | 32 |
| Decane | 23.6 ± 0.1 | 32 |
| Nonane | 22.6 ± 0.2 | 31 |
| Octane | 21.4 ± 0.2 | 30 |

TABLE 2

Measured Contact Angles of Various Liquids on Different Flat Solids.

| Solids | | $H_2O$ | $C_{16}H_{34}$ | $C_{13}H_{22}$ | $C_{10}H_{22}$ | $C_8H_{18}$ | $C_6H_{14}$ | $C_5H_{12}$ | FC-70 |
|---|---|---|---|---|---|---|---|---|---|
| S. Epoxy | $\theta_{adv}$ | 118.9 ± 1.7 | 76.3 ± 1.4 | 72.8 ± 0.2 | 66.0 ± 4.1 | 57.7 ± 2.5 | 52.5 ± 0.3 | 36.4 ± 2.5 | 23.7 ± 4.1 |
| | $\theta_{static}$ | 113.1 ± 2.8 | 70.5 ± 2.0 | 63.5 ± 2.8 | 60.0 ± 2.8 | 50.7 ± 3.0 | 40.1 ± 4.2 | 30.8 ± 3.1 | 14.1 ± 0.8 |
| | $\theta_{rec}$ | 90.8 ± 0.9 | 50.0 ± 3.9 | 48.1 ± 3.1 | 38.5 ± 0.7 | 23.8 ± 4.0 | 22.8 ± 1.7 | 17.0 ± 1.8 | 0.0 ± 0.0 |
| Epoxy | $\theta_{adv}$ | 100.3 ± 3.1 | 32.8 ± 1.4 | 28.3 ± 1.1 | 15.0 ± 1.6 | 9.7 ± 1.2 | ~0.0 | ~0.0 | 35.1 ± 0.6 |
| | $\theta_{static}$ | 92.6 ± 1.8 | 30.6 ± 0.4 | 26.9 ± 1.7 | 14.2 ± 0.7 | 7.9 ± 0.7 | ~0.0 | ~0.0 | 33.5 ± 1.1 |
| | $\theta_{rec}$ | 67.0 ± 4.5 | 25.7 ± 0.9 | 25.4 ± 0.7 | 13.7 ± 0.9 | 6.1 ± 0.2 | ~0.0 | ~0.0 | 26.7 ± 1.4 |
| Silicon | $\theta_{adv}$ | 14.4 ± 2.7 | 17.3 ± 1.6 | — | 7.9 ± 1.0 | <5.0 | <5.0 | <5.0 | — |
| | $\theta_{static}$ | 13.1 ± 1.7 | 5.6 ± 1.1 | — | <5.0 | <5.0 | <5.0 | <5.0 | — |
| | $\theta_{rec}$ | ~0.0 | ~0.0 | — | ~0.0 | ~0.0 | ~0.0 | ~0.0 | — |

TABLE 3-continued

Measured Surface Tension for Various Polar and Non-Polar Liquids.

| Liquid | Surface Tension (mN/m) | n |
|---|---|---|
| Heptane | 19.9 ± 0.3 | 32 |
| Hexane | 18.6 ± 0.5 | 30 |
| Pentane | 17.2 ± 0.5 | 57 |
| 3M Fluorinert ™ FC-70 | 17.1 ± 0.3 | 43 |

Notice that $\gamma_A$ and $\gamma_B$ are equivalent to $\gamma_{AX}$ and $\gamma_{BX}$ defined in the text, and medium X is air specifically in this context. $\gamma_{AB}$ represents the interfacial tension for Object A-Liquid B interface. Specifically, $\gamma_{AB}$ for water-perfluorocarbon and hydrocarbon-perfluorocarbon interfaces were measured by the pendant droplet method (see Table 4), with exception for those of the water-hydrocarbon interfaces which are estimated from the formulation: $\gamma_{AB}=\gamma_A+\gamma_B-2(\gamma_A^d\gamma_B^d)^{1/2}$, where $\gamma_A^d$ and $\gamma_B^d$ are the dispersion force contributions of the liquid surface tensions (Fowkes, F. M., *Ind. Eng. Chem.* 56, 40-42, 1964; Israelachvili, J. N. *Intermolecular and Surface Forces*, Academic Press, 2011). The dispersion force contribution of water surface tension is 21.8 mN/m (Fowkes, F. M., *Ind. Eng. Chem.* 56, 40-42, 1964). S. Epoxy represents silanized epoxy resin substrate. Alkanes are represented in $C_nH_{2n+2}$ where n=5, 6, 8, 10, 13, and 16.

TABLE 4

Measured Interfacial Tension between a Perfluorocarbon and Various Liquids.

| Liquid/Liquid | Interfacial Tension (mN/m) | n |
|---|---|---|
| FC-70/Water | 56.0 ± 0.9 | 12 |
| FC-70/Hexadecane | 8.2 ± 0.2 | 25 |
| FC-70/Tridecane | 7.7 ± 0.3 | 26 |
| FC-70/Decane | 6.7 ± 0.2 | 26 |
| FC-70/Octane | 4.4 ± 0.2 | 25 |
| FC-70/Hexane | 2.6 ± 0.1 | 40 |
| FC-70/Pentane | <2.5 | 10 |

In certain cases, it may be desirable to have the surface energies of the roughened surface and Liquid B to be lower than the surface energy of Object A so that Object A will not displace Liquid B from the roughened solid (see Table 1).

In certain embodiments, when Object A is a low surface tension non-polar liquid (e.g., less than 30 mN/m), the roughened surface may be functionalized with low surface energy coatings (e.g., less than 30 mJ/m$^2$), such as —CF$_3$, —CF$_2$H, —CF$_3$ and —CF$_2$—, —CF$_2$—CF$_3$, —CF$_2$—CFH—, —CF$_2$—CH$_2$—, —CFH—CH$_2$—, and the like. Moreover, Liquid B may be selected to also exhibit low surface energy (e.g., less than 20 mJ/m$^2$), such as perfluorotributylamine, perfluorotri-n-pentylamine, perfluorohexane, perfluoro(2-butyl-tetrahydrofuran), perfluorocycloether, perfluoro n-alkyl morpholines, perfluoroalkylethers, perfluorotripropylamine, and the like.

In certain embodiments, when Object A is a high surface tension liquid (e.g., water, fog, condensation) or a solidified fluid (e.g., ice, frost, etc.), Liquid B can be selected from other higher surface energy fluids (i.e., ~20 mJ/m$^2$ or higher), such as polydimethylsiloxane, other liquid silicone elastomers or commercial food grade lubricants (e.g., KRYTOX™ FG lubricants), oils (e.g., olive oil, canola oil, vegetable oil, sunflower oil, their mixtures, etc.) and the like. In certain embodiments, as with low surface tension liquids, the roughened surface may be functionalized with low surface energy coatings (e.g., less than 30 mJ/m$^2$), such as —CF$_3$, —CF$_2$H, —CF$_3$ and —CF$_2$—, —CF$_2$—CF$_3$, —CF$_2$—CFH—, —CF$_2$—CH$_2$—, —CFH—CH$_2$—, and the like. Selected materials combinations of slippery liquid-infused porous surface(s) is known in Table 5.

TABLE 5

Selected Examples of Materials Combinations for Slippery Liquid-Infused Porous Surface(s).

| Solid | Liquid B | Liquid A |
|---|---|---|
| Polydimethylsiloxane OR Polypropylene OR Polytetrafluoroethylene Polytetrafluoroethylene OR Fluoro-silanized Metals (e.g., Aluminum) OR Fluoro-silanized Natural Polymers OR Fluoro-silanized Synthetic Polymers | Polydimethylsiloxane OR Olive Oil and the Like OR Liquid Hydrocarbons Perfluorinated Fluids | Simple and Complex Aqueous Fluids, such as Water and Blood. Solidified Fluids, such as Ice All Liquids Except Perfluorinated Fluids |

Applications

Numerous different applications for slippery liquid-infused porous surface(s) can be envisioned where surface that repel a wide range of materials is desired. Some non-limiting exemplary applications are described below.

Microfluidic Systems

Slippery liquid-infused porous surface(s) can be integrated in miniature channels for microfluidic devices and systems (see FIG. 10, Designs D1 to D5 and E1 to E5), where laminar flow is the dominant mechanism of fluid transport. Specifically, the fluid flow condition can be characterized by Reynolds number, which is a dimensionless number that quantifies the ratio of inertia forces to viscous forces in a specific flow condition. Reynolds number (Re) can be further expressed as Re=vL/η, where v is the mean velocity of the flow, L is the characteristic length of the flow system, and η is the kinematic viscosity of the fluid. For small Reynolds number (i.e., Re <100), the fluid flow is typically laminar; whereas for large Reynolds number (i.e., Re >2000), the flow becomes turbulent (see for example Drag-reduction for high flow systems). For microfluidic systems where the channel dimensions is typically on the order of 10 μm to 1 mm, the Reynolds number is on the order of 100 or less.

In embodiments, an entire tube or pipe having a roughened surface (e.g., TEFLON tubes or pipes having a porous network of TEFLON fibers) can be produced or obtained commercially (see Zeus, Inc.).

In certain embodiments, slippery liquid-infused porous surface(s) can be incorporated into microfluidic systems by attaching Liquid B-soaked porous membranes (such as Teflon) to the interior of the channels (see for example FIGS. 9B-D and 10). The configuration can be implemented in a finite source of Liquid B configuration, where the amount of Liquid B that can be replenished to the porous membrane is at a fixed amount (see Designs D1 to D5 of FIG. 10). Alternatively, the configuration can be implemented in a large source of Liquid B configuration by attachment of one or more reservoirs, where Liquid B can be constantly replenished as needed to the porous membrane, as depicted in Design E1 to E5 of FIG. 10.

In an alternative embodiment, where the microfluidic channel has a roughened surface that does not sufficiently "hold" onto Liquid B under flow conditions (e.g., a microfluidic channel with relatively smooth sidewall), slippery liquid-infused porous surface(s) can be created by injecting Liquid B and Liquid A simultaneously into the channel to form a two-phase flow (see for example, Wong et al. *J. Fluid. Mech.* 497, 55-65 (2003)). In this configuration, Liquid B can attach to the channel sidewall with Liquid A at the center of the channel (i.e., similar to that of the core-annular flow in a macroscale fluidic system, see for example, Bai et al., *Annu. Rev. Fluid. Mech.* 29, 65-90 (1997)). The thickness of Liquid B can be adjusted by the relative flow rates between Liquid B and Liquid A. In designing such a system, the material requirements of Liquids A and B and the material of the roughened surface may be selected such that they satisfy the condition (e1).

In certain embodiments, a roughened surface can be grown on conductive (e.g., metals, conductive polymers, etc.) pipes, cylinders, and any other flow paths using electrodeposition as described in PCT/US11/44553, filed on Jul. 19, 2011, the contents of which is incorporated by reference herein in its entirety.

In certain embodiments, Liquid B can be chosen to be optimized for extreme temperatures and heat transfer characteristics, bio-compatible, or shear-resistant. Typically, perfluorinated fluids may satisfy part or all of these requirements.

The high mobility of the Liquid A-Liquid B interface (e.g., where the molecules at the interfacial boundary between Liquid A and Liquid B are not fixed and are free to move) in the flow within the microfluidic channels may allow for Liquid A to slip at the interfacial boundary. Such a slippage may reduce the drag required to transport Liquid A, thereby reducing the energy to push Liquid A through the microfluidic channels.

Drag-reduced microfluidic devices and systems may find important applications where energy-efficient transport of fluids or non-sticking of biological components are critical. Specific application examples include integrated biosensing systems for body fluids such as blood, saliva, DNA solutions, urine, sweat, etc.; sorting devices for biological entities; blood transfusion tubing and storage packages; artificial blood vessels; blood cleansing devices; dialysis; energy-efficient microfluidic cooling system for computer chips; materials synthesis in microfluidic systems, such as polymers, bio-barcode, DNA complexes (see for example: Rothemund, *Nature* 440, 297-302 (2006)), medicine, etc.; microfluidic computation systems (see for example: Prakash and Gershenfeld, *Science* 315, 832-835 (2007); Fuerstman et al., *Science* 315, 828-832 (2007)); fast drug screening (see for example: Wong et al., *Proc. Natl. Acad. Sci. USA* 105, 5105-5110 (2008)); drug discovery, paper diagnostics, and other lab-on-a-chip or organ-on-a-chip applications, etc.

Fuel Transport, Water Transporting Pipes for High-Rise Buildings/District Heating and Cooling and Fuel Transport (High Pressure Flow), and Drag Reduction Skins for Turbines, Aircraft, Etc./Airplane Foils/Body of Marine Vehicles Slippery liquid-infused porous surface(s) can be integrated in macroscopic channels/pipes and the like for large-scale fluid transport (see FIG. 10, Design D1 to D5 and E1 to E5) or as drag-reduction skins for airplane foils/body of marine vehicles (e.g., submarine), where laminar and turbulent flows are the dominant mechanisms of fluid transport. Specifically, for macroscale flow systems where the channel dimensions are typically on the order of centimeters to meters, the Reynolds number is on the order of 1000 or higher. For high-flow systems, Reynolds number is typically above 2000, and sometimes can go as high as orders of 10000, where turbulent flows occur.

Slippery liquid-infused porous surface(s) can also be incorporated into macroscale flow systems by attaching porous membranes (such as Teflon) to the interior of the channels/pipes and the like. The configuration can be implemented in either finite source of Liquid B (see Design D1 to D5 of FIG. 10) or infinite source of Liquid B by attachment reservoir directly to the channels/pipes and the like, as depicted in Design E1 to E5 of FIG. 10.

In an alternative embodiment, where the macroscopic channel/pipe has a roughened surface that does not sufficiently "hold" onto Liquid B under flow conditions (e.g., a macroscopic channel/pipe and the like with smooth sidewall), slippery liquid-infused porous surface(s) can be created by injecting Liquid B and the working Liquid A simultaneously into the channel to form core-annular flow (see for example, Bai et al., *Annu. Rev. Fluid. Mech.* 29, 65-90 (1997)). In this configuration, Liquid B can attach to the channel sidewall with Liquid A at the center of the channel. The thickness of Liquid B layer can be adjusted by the relative flow rates between Liquid B and Liquid A. In designing such a system, the material requirements of Liquids A and B and the material of the roughened surface can be selected such that they satisfy the condition (e1).

In other embodiments, slippery liquid-infused porous surface(s) can be incorporated onto arbitrary-shape objects (e.g., airplane foils) by attaching lubricant-soaked porous membranes (such as Teflon) onto the surfaces, or by double spray-coating, or by other aforementioned methods. The configuration can be implemented in either finite source of Liquid B (see Design A1 to A8 of FIG. 10) or infinite source of Liquid B by attachment reservoir directly to the roughened surfaces, as depicted in Design B1 to B8, or replenishing by spraying of Liquid B, as depicted in Design C1 to C8, of FIG. 10.

In certain embodiments, a roughened surface can be grown on conductive (e.g., metals, conductive polymers, etc.) pipes, cylinders, and any other flow paths using electrodeposition as described in PCT/US11/44553, filed on Jul. 19, 2011, the contents of which is incorporated by reference herein in its entirety.

In certain embodiments, a pipe, cylinder or other desired flow path can be etched with an etchant to create surface roughness in the areas where the etchant contacted the flow path. Etchants include chemical liquids, blasting particles, reactive plasma, or any other materials/processes that can induce a desired surface roughness. In certain embodiments, etching can be terminated by stopping the etching process or introducing the flow path with an inert liquid or vapor. In certain embodiments, Liquid B can be provided as the inert liquid to simultaneously stop the etching and form a slippery liquid-infused porous surface(s).

In certain embodiments, prior to introducing the inert liquid, a second liquid or vapor that can provide any desired chemical modification of the roughened surface can be introduced.

Liquid B can be chosen to be index-matched with the substrate for optical transparency, optimized for extreme temperatures and heat transfer characteristics, bio-compatible, or shear-resistant. Typically, perfluorinated fluids may satisfy part or all of these requirements.

The mobility of the Liquid A-Liquid B interface in the flow within the macroscale channels/pipes and the like may allow for Liquid A to slip at the interfacial boundary between Liquid A and Liquid B. Such a slippage may reduce the drag required to transport Liquid A, thereby reducing the energy to push Liquid A through the macroscale channels/pipes and the like.

Drag-reduced macroscale channels/pipes and the like devices and systems may find important applications where energy-efficient transport of fluids, non-sticking of various different components and materials (e.g., ice) are important. Specific application examples include district heating and cooling systems; water/oil/fuel transport and storage; anti-icing airplane foils/turbines; heat exchange pipes and jackets in chemical (and other) industries; biofouling-resistant pipes; biofouling-resistant coatings for ships/sub-marines, etc.

Refrigeration

Modern 'frost-free' refrigerators use a built-in electrical heater to remove frost formed on the surface of the heat exchanger up to six times a day with 20-30 minutes of active heating during each defrost cycle, which imposes a significant amount of capital cost and energy consumption. Therefore, reduction of frost formation and decreasing the frequency and the period of defrost cycles can significantly limit energy used and reduce carbon emissions to our environment.

Thus, another particular application where slippery liquid-infused porous surface(s) can be utilized includes coatings for refrigerator coils, fins, cartridges and other refrigerated surfaces that are subject to condensation, frost formation, and ice accumulation in industrial and residential refrigerators. In certain embodiments, the refrigerator coils can be provided with a desired porous surface using electrodeposition of conductive polymers as described in PCT/US11/44553, filed on Jul. 19, 2011, the contents of which is incorporated by reference herein in its entirety. Then, Liquid B that can specifically repel water, ice, and frost can be selected. The roughened surface can be infiltrated to form an ultra-smooth layer of Liquid B thereon. In certain embodiments, a reservoir that can replenish any loss of Liquid B can be provided (see, e.g., FIGS. 7B and 9A, and Designs A1 to A8, B1 to B8, and C1 to C8 of FIG. 10). The refrigerator coil having slippery liquid-infused porous surface(s) can be connected into a defrost system, which can significantly decrease the amount of frost formation. In certain embodiments, any frost accumulated can be more easily removed (as compared to conventional refrigerator coils) by heating the refrigerator coil to a much lower temperature and for a shorter period to remove the frost. In certain embodiments, mechanical agitation or gentle flow of air, such as the reverse cycle of a compressor generating warm stream of air to defrost the coil that is currently used in the art, can further expedite removal of the melted frost (e.g., water droplets) away from the refrigerator coils.

In certain embodiments, slippery liquid-infused porous surface(s) not only inhibit, reduce or delay condensation thereon, but any condensed ice/frost can be efficiently removed by a short heating to transform the condensed frost/ice into water droplets, followed by gentle agitation or air flow that efficiently, almost instantaneously, removes the droplets or entire ice pieces making the surface of a refrigerator coil ready for the next cooling cycle. Current industrial practice requires heating refrigerator coils up to room temperature for 4-6 times a day for 15-30 minutes for each defrosting cycle. However, slippery liquid-infused porous surface(s) can prevent ice formation and ice adhesion with temperatures only slightly above melting temperature (~5° C.), and shorten the duration of a defrosting cycle down to less than a minute.

Additional criteria that may be particularly important for such applications include, minimized evaporation rate, optimized viscosity for enhanced liquid/ice-repellency, improved heat-transfer characteristics, low freezing point etc. Hence, Liquid B and the roughened surface can be selected to provide all or optimized combination of these characteristics.

In certain embodiments, the roughened surface can be selected from roughened aluminum, copper, polypyrrole, polyaniline, and the like and Liquid B can be selected from perfluoropolyether.

Anti-Icing Surfaces for Aircrafts, Power Lines, Turbines, Oil Transport Pipelines, and Telecommunications Equipment Ice formation and accretion present serious economic and safety issues for many essential infrastructures, such as aircrafts, power lines, turbines, marine vessels, oil transport pipelines, and telecommunications equipment. One particular application where slippery liquid-infused porous surface(s) can be utilized include anti-icing coatings for the aforementioned infrastructures, and the like.

In certain embodiments, the surface of the construction materials can be roughened to provide a porous surface (i.e., roughened surface). Then, Liquid B that can repel contaminants, such as water condensates, frost, and ice, and the like can be selected. Then, the roughened surface can be infiltrated with Liquid B to form an ultra-smooth layer of Liquid B thereon. In certain embodiments, a reservoir that can replenish any loss of Liquid B can be provided (see, e.g., FIGS. 9B and 9C and Designs A1 to A8, B1 to B8, and C1 to C8 of FIG. 10).

Additional criteria that may be particularly important for applications in this category include shear-resistance, self-healing, and stability in extreme temperature range. Hence, Liquid B and the roughened surface can be selected to provide all or optimized combination of these characteristics.

In certain embodiments, the roughened surface can be selected from fluorosilanized materials and Liquid B can be selected from perfluoropolyether. Other non-fluorinated materials include silicone elastomer as the porous solid, and liquid silicone as the Liquid B.

Anti-Fingerprinting Screen

Yet another particular application where slippery liquid-infused porous surface(s) can be utilized includes anti-fingerprinting coatings for windows or optical screens for mobile devices, computers, automatic teller machine, and the like. For example, slippery liquid-infused porous surface(s) can be applied over the optical surface to prevent the build-up of fingerprint and anti-wetting to a broad range of liquid contaminants.

Fingerprint residues imprinted by the contact of the finger on a surface consist mostly of sebum (e.g., lipids) and sweat (i.e., salty water), which is retained on most smooth solid surfaces. With the highly non-wetting, low-adhesion, and self-healing properties of slippery liquid-infused porous surface(s), fingerprint residues will be difficult to stay attach on the liquid surface.

In certain embodiments, the optical surface can be patterned to provide a porous surface (i.e., roughened surface). In some cases, the porous solid can be designed to provide anti-glare property (e.g., random networks of fibers). Then, Liquid B that can repel contaminants, such as water, alcohols, and oils the like can be selected. In addition, Liquid B can be selected so that the refractive index of Liquid B is matched with that of the optical surface to enhance optical transparency. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include optical transparency, shear-resistant, and fast self-healing. Hence, Liquid B and the roughened surface can be selected to provide all or optimized combination of these characteristics.

In certain embodiments, the roughened surface can be selected from fluorosilanized glass/porous Teflon and Liquid B can be selected from perfluoropolyether.

Building and Construction Materials: Anti-Graffiti Surface

One particular application where slippery liquid-infused porous surface(s) can be utilized include anti-graffiti coatings for buildings, statues, public infrastructures and the like.

Figure 25:
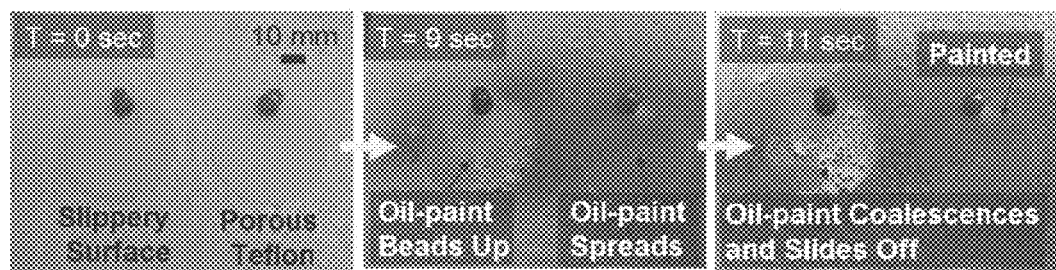
FIG. 25 shows a series of images demonstrating anti-painting capability of the slippery surface where the Teflon or the wall background, to which the Teflon and slippery surfaces are attached, cannot resist the adhesion of oil-based spray paint and was uniformly coated whereas the oil paint coalesces and slides off the slippery surface in accordance with certain embodiments.

In certain embodiments, slippery liquid-infused porous surface(s) can be used for anti-graffiti purposes as they resist wetting of oil-based/water-based spray paints. Even when the paints solidify onto the slippery liquid-infused porous surface(s), the paints have very low adhesion to the surfaces which can be removed easily with adhesion tapes and the like (see, e.g., FIG. 25). In addition, the solidified paints can also be removed by regular solvents, such as acetone without leaving traces of residues.

In certain embodiments, the surface of the construction materials can be roughened to provide a porous surface (i.e., roughened surface). Then, Liquid B that can repel contaminants, such as water-based spray paint, oil-based spray paint, rain, and the like can be selected. Then, the roughened surface can be infiltrated with Liquid B to form an ultra-smooth layer of Liquid B thereon. In certain embodiments, a reservoir that can replenish any loss of Liquid B can be provided (see, e.g., FIGS. 9B and 9C and Designs A1 to A8, B1 to B8, and C1 to C8 of FIG. 10).

Additional criteria that may be particularly important for applications in this category include shear-resistance, self-healing, and anti-wetting and anti-adhesive. Hence, Liquid B and the roughened surface can be selected to provide all or optimized combination of these characteristics.

In certain embodiments, the roughened surface can be selected from fluorosilanized materials and Liquid B can be selected from perfluoropolyether.

Building and Construction Materials: Self-Cleaning Surfaces, Buildings, Billboards, Signs, Sanitation Systems (e.g., Toilet Bowl), Pest Control Materials Etc.

Another application where slippery liquid-infused porous surface(s) can be utilized include self-cleaning buildings, billboards, signs, pest control, sanitation systems (e.g., toilet bowl), and the like. For example, slippery liquid-infused porous surface(s) can be applied over the sides of the building, windows, billboards, signs, and the like to provide self-cleaning and insect-repellent capabilities. First, large sheets of roughened surface, such as a porous substrate, can be applied to buildings, billboards, signs, and the like. Then, suitable Liquid B that can repel contaminants, such as smog, dirt, insects, bird feces, and the like can be selected and the roughened surface can be infiltrated therein to form an ultra-smooth layer of Liquid B thereon. In certain embodiments, a reservoir that can replenish any loss of Liquid B, due to evaporation, environmental damage, wear and tear, and the like, can be provided.

In certain embodiments, slippery liquid-infused porous surface(s) can be used for anti-graffiti purposes as they resist wetting of oil-based/water-based spray paints. Even when the paints solidify onto the slippery liquid-infused porous surface(s), the paints have very low adhesion to the surfaces which can be removed easily with adhesion tapes and the like (see, e.g., FIG. 25). In addition, the solidified paints can also be removed by regular solvents, such as acetone without leaving traces of residues.

In certain embodiments, slippery liquid-infused porous surface(s) can be used for coatings for common sanitation systems, such as toilet flushing systems. More specifically, lubricants (Liquid B) can be easily integrated with the existing infrastructures, and flushed into the toilet bowl to refresh the slippery liquid-infused porous surface(s), which can then be used as anti-sticking and anti-wetting surfaces for both liquid and solid wastes. Also, slippery liquid-infused porous surface(s) can also be used as anti-bacterial surfaces due to the poor adhesion of the bacteria/bio-films with the slippery liquid-infused porous surface(s). The integration of slippery liquid-infused porous surface(s) with the sanitation systems present a sustainable way to minimize usage of water and aggressive disinfectants, which would help reduce diseases spreading in both the rural and metropolitan areas.

Additional criteria, in addition to repellency of the contaminants, that may be particularly important for such applications include optical transparency, biocompatibility, minimized evaporation rates, optimized viscosity for enhanced liquid/ice-repellency. Hence, Liquid B and the roughened surface can be selected to provide all or optimized combination of these characteristics.

In certain embodiments, the roughened surface can be selected from porous Teflon-coated metals and Liquid B can be selected from perfluoropolyether.

Fabrics, Clothes and Shoes

Yet, another application where slippery liquid-infused porous surface(s) can be utilized include self-cleaning fabrics, clothes and shoes, and the like. For example, Liquid B can be infiltrated into the porous materials for fabrics, clothing (e.g., Gore-Tex) and shoes. Suitable Liquid B that can repel contaminants, such as dirt, insects, bird feces, soy sauce and the like, wine and the like, olive oil and the like, can be selected and the roughened surface can be infiltrated therein to form an ultra-smooth layer of Liquid B thereon. In certain embodiments, a reservoir that can replenish any loss of Liquid B, due to evaporation, environmental damage, wear and tear, and the like, can be provided.

Figure 26A:
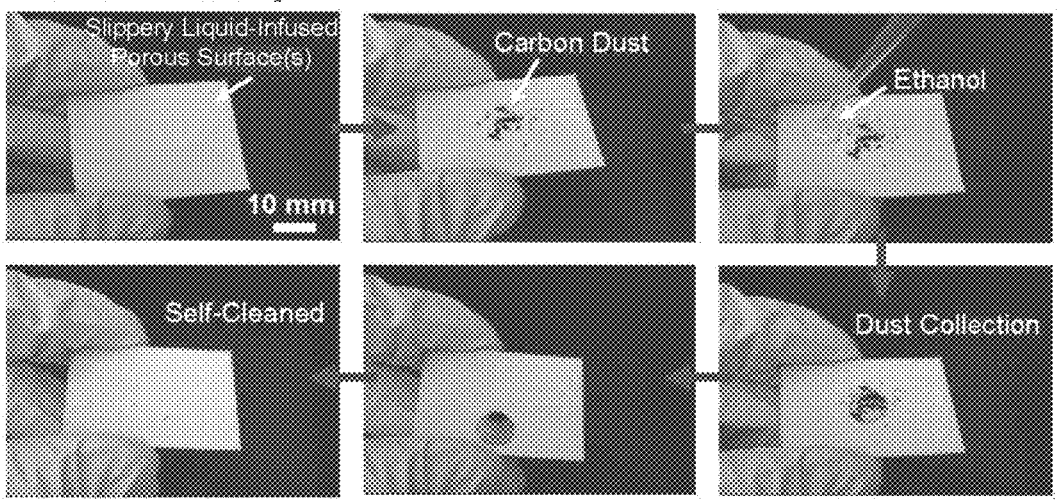
FIGS. 26A and 26B show a time sequence of images demonstrating the ability to clean off particulate (carbon dust by ethanol in FIG. 26A and glass dust by water in FIG. 26B) contaminants from slippery liquid-infused porous surface(s) in accordance with certain embodiments.
Figure 26B:
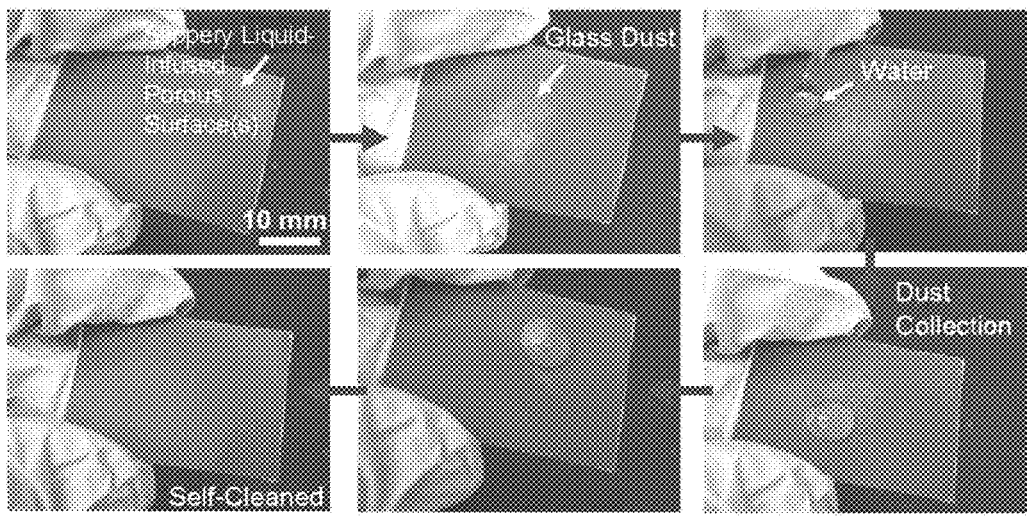

In certain embodiments, it is contemplated that while contaminants, such as dirt, smog, bird feces and the like, can temporarily "stick" onto the slippery liquid-infused porous surface(s) surface, introduction of a "second Object A," such as a liquid that attracts the contaminants (e.g., solvent, water, rain or even dew), may further enhance self-cleaning by collecting the contaminants and carrying them away (see, e.g., FIGS. 26A and 26B).

Additional criteria, in addition to repellency of the contaminants, that may be particularly important for such applications include optical transparency, biocompatibility, minimized evaporation rates, optimized viscosity for enhanced liquid/ice-repellency. Hence, Liquid B and the roughened surface can be selected to provide all or optimized combination of these characteristics.

In certain embodiments, the roughened surface can be selected from porous Teflon-coated metals and Liquid B can be selected from perfluoropolyether.

Coatings on Ship/Boat—Anti-Marine Biofouling

Another application where slippery liquid-infused porous surface(s) can be utilized include anti-marine biofouling coatings on ship/boat/submarine and the like. For example, slippery liquid-infused porous surface(s) can be applied over the sides of the ship/boat/submarine, and the like to provide anti-biofouling capabilities. First, large sheets of roughened surface, such as a porous substrate, can be applied to ship/boat/submarine, and the like, by spray-coating. Then, suitable Liquid B that can prevent the settlement of marine contaminants, such as mussels, sea squirts, barnacles, tubeworm, tubeworm larva, diatom 'slimes' and the like can be selected and the roughened surface can be infiltrated with Liquid B to form an ultra-smooth layer of Liquid B thereon. In certain embodiments, a reservoir that can replenish any loss of Liquid B, due to evaporation, environmental damage, wear and tear, and the like, can be provided.

In certain embodiments, it is contemplated that while marine contaminants, such as mussels, sea squirts, barnacles, tubeworm, tubeworm larva, diatom 'slimes', microorganisms, and the like, can temporarily "stick" onto the slippery liquid-infused porous surface(s) surface, introduction of a "second Object A," such as a liquid (e.g., water) that shear off the contaminants, may further enhance self-cleaning by carrying the contaminants away.

Additional criteria, in addition to repellency of the contaminants, that may be particularly important for such applications include biocompatibility, minimized evaporation rates, optimized viscosity for reduced adhesion with the marine-contaminants. Hence, Liquid B and the roughened surface can be selected to provide all or optimized combination of these characteristics.

In certain embodiments, the roughened surface can be selected from porous Teflon-coated metals and Liquid B can be selected from perfluoropolyether.

Coatings for Instruments Such as Camera/Window

One particular application where slippery liquid-infused porous surface(s) can be utilized include coatings for instruments such as cameras, windows, and the like. For example, slippery liquid-infused porous surface(s) can be applied over the optical component to prevent adhesion of contaminants during operation.

In certain embodiments, the surface of the window can be patterned to provide a porous surface (i.e., roughened surface). Then, Liquid B that can repel contaminants, such as rain, fingerprints, and the like can be selected. If the device is intended for underwater applications, Liquid B that can repel contaminants, such as mussels, sea squirts, barnacles, tubeworm, tubeworm larva, diatom 'slimes', micro-organisms, excretions from marine creatures (e.g., octopus ink), and the like can be selected. In addition, Liquid B can be selected so that the refractive index of Liquid B is matched with that of the window, camera, and the like instruments. Then, the roughened surface can be infiltrated with Liquid B to form an ultra-smooth layer of Liquid B thereon. In certain embodiments, a reservoir that can replenish any loss of Liquid B can be provided (see, e.g., FIGS. 9B and 9C and Designs A1 to A8, B1 to B8, and C1 to C8 of FIG. 10).

Additional criteria that may be particularly important for applications in this category include optical transparency, high pressure stability, biological compatibility, shear-resistance. Hence, Liquid B and the roughened surface can be selected to provide all or optimized combination of these characteristics.

In certain embodiments, the roughened surface can be selected from fluorosilanized glass and Liquid B can be selected from perfluoropolyether.

Night Vision/Other Infrared-Related Optical Applications

Yet another particular application where slippery liquid-infused porous surface(s) can be utilized includes coatings for windows or optical components for night vision/other infrared-related optical instruments. For example, slippery liquid-infused porous surface(s) can be applied over the optical components to prevent fog/frost/ice build-up and anti-wetting to a broad range of liquid contaminants.

In certain embodiments, the surface of the window can be patterned to provide a porous surface (i.e., roughened surface). Then, Liquid B that can repel contaminants, such as fog, frost, ice, oil, oil-based/water-based ink, smog, dirt, insects, bird feces, and the like can be selected. In addition, Liquid B can be selected so that the refractive index of Liquid B is matched with that of the window of the optical components. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include optical transparency for near-IR range, low-freezing point, high pressure stability, minimized evaporation rate, optimized viscosity for enhanced liquid/ice-repellency. Hence, Liquid B and the roughened surface can be selected to provide all or optimized combination of these characteristics.

In certain embodiments, the roughened surface can be selected from fluorosilanized glass/porous Teflon and Liquid B can be selected from perfluorotri-n-pentylamine.

Solar Cell, Roof Tiling

Another particular application where slippery liquid-infused porous surface(s) can be utilized include coatings for solar cell and roof tiling. For example, slippery liquid-infused porous surface(s) can be applied over the optical screen of solar cells/roof tiling to prevent fog/frost/ice build-up and anti-wetting to a broad range of liquid contaminants, as well as solid contaminants.

In certain embodiments, the surface of the window can be patterned to provide a porous surface (i.e., roughened surface). Then, Liquid B that can repel contaminants, such as fog, frost, ice, oil, smog, dirt, insects, bird feces, and the like can be selected. In addition, Liquid B can be selected so that the refractive index of Liquid B is matched with that of the window of the optical screen. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include optical transparency for both visible and near-IR range, low-freezing point, minimized evaporation rate, optimized viscosity for enhanced liquid/ice-repellency, and shear resistance. Hence, Liquid B and the roughened surface can be selected to provide all or optimized combination of these characteristics.

In certain embodiments, the roughened surface can be selected from fluorosilanized glass/porous Teflon and Liquid B can be selected from perfluorotri-n-pentylamine/polyfluoropolyester.

Anti-Fogging Lens/Goggle slippery liquid-infused porous surface(s) can also be utilized as coatings for anti-fogging lens/goggle. For example, slippery liquid-infused porous surface(s) can be applied over the optical surface of lens/goggle to prevent fog/frost/ice build-up and anti-wetting to a broad range of liquid contaminants, as well as solid contaminants.

In certain embodiments, the optical surface can be patterned to provide a porous surface (i.e., roughened surface). Then, Liquid B that can repel contaminants, such as fog, frost, ice, oil, smog, dirt, insects, bird feces, and the like can be selected. In addition, Liquid B can be selected so that the refractive index of Liquid B is matched with that of the window of the optical screen. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include optical transparency for both visible and near-IR range, low-freezing point, minimized evaporation rate, optimized viscosity for enhanced liquid/ice-repellency, and shear resistance. Hence, Liquid B and the roughened surface can be selected to provide all or optimized combination of these characteristics.

In certain embodiments, the roughened surface can be selected from fluorosilanized glass and Liquid B can be selected from perfluorotri-n-pentylamine/polyfluoropolyester.

Robotic Endoscope

One particular application where slippery liquid-infused porous surface(s) can be utilized include robotic endoscope. For example, slippery liquid-infused porous surface(s) can be applied over the optical component to prevent adhesion of complex biological fluids, materials, cells, tissues during operation.

In certain embodiments, the tip of the endoscope can be patterned to provide a porous surface (i.e., roughened surface). Then, Liquid B that can repel contaminants, such as blood, cells, tissues and the like can be selected. In addition, Liquid B can be selected so that the refractive index of Liquid B is matched with that of the tip of the endoscope. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include biological compatibility, optical transparency, shear-resistance, and self-repair. Hence, Liquid B and the roughened surface can be selected to provide all or optimized combination of these characteristics.

In certain embodiments, the roughened surface can be selected from fluorosilanized glass and Liquid B can be selected from perfluorodecalin. In certain embodiments, the roughened surface/Liquid B combinations, such as Teflon/perfluorodecalin can be selected, as well. Further example includes roughened silicone elastomer such as polydimethylsiloxane and Liquid B can be selected from liquid polydimethylsiloxane.

Anti-Fouling Membrane Filters for Waste-Water Treatment

Another application where slippery liquid-infused porous surface(s) can be utilized include membrane filters for waste water treatment. For example, slippery liquid-infused porous surface(s) can be applied over the surface of membrane filters to prevent adhesion of debris, biofilm, minerals deposit in the waste water.

In certain embodiments, the membrane filters can be patterned to provide a porous surface (i.e., roughened surface). Then, Liquid B that can repel contaminants, such as mineral deposits, biofilm and the like can be selected. The roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

Additional criteria that may be particularly important for such applications include biological compatibility, heat-resistant, shear-resistance, and self-repair. Hence, Liquid B and the roughened surface can be selected to provide all or optimized combination of these characteristics.

In certain embodiments, the roughened surface can be selected from fluorosilanized polymers and Liquid B can be selected from perfluoropolyether. In certain embodiments, the roughened surface/Liquid B combinations, such as Teflon/perfluoropolyether can be selected, as well. Further example includes roughened silicone elastomer such as polydimethylsiloxane and Liquid B can be selected from liquid polydimethylsiloxane; as well as roughened polypropylene and Liquid B can be selected as liquid polydimethylsiloxane or perfluoropolyether.

Cookware, Bottles/Containers for Food Storage or Daily Consumables

Yet another application where slippery liquid-infused porous surface(s) can be utilized include slippery coatings for cookware, or bottles/containers for food storage such as ketchup or daily consumables such as detergent, shampoos and the like. For example, slippery liquid-infused porous surface(s) can be applied over interior of the bottles/containers to enhance the slipperiness to completely remove the fluids within the bottles/containers.

In certain embodiments, the interior of the bottle can be patterned to provide a porous surface (i.e., roughened surface). Then, Liquid B that can repel food/daily consumables, such as ketchup, detergent, shampoos and the like can be selected. Then, the roughened surface can be infiltrated to form an ultra-smooth layer of Liquid B thereon. In certain embodiments, a reservoir that can replenish any loss of Liquid B can be provided (see, e.g., FIGS. 9B and 9C and Designs A1 to A8, B1 to B8 and C1 to C8 of FIG. 10).

In certain embodiments, the interior of the bottle can be smooth. In this case, Liquid B of high chemical affinity can be applied onto the surface to form a uniform coating.

Additional criteria that may be particularly important for such applications include biological compatibility, temperature resistant, shear-resistance, and self-repair. Hence, Liquid B and the roughened/smooth surface can be selected to provide all or optimized combination of these characteristics.

In certain embodiments, the roughened surface can be selected from fluorosilanized plastics and Liquid B can be selected from perfluorodecalin/perfluoropolyether. In certain embodiments, the roughened surface/Liquid B combinations, such as Teflon/perfluorodecalin can be selected, as well. Further example includes roughened silicone elastomer such as polydimethylsiloxane or roughened polypropylene, and Liquid B can be selected as liquid polydimethylsiloxane or perfluoropolyether.

EXAMPLES

Example 1

Slippery surfaces with exceptional pressure stability, optical transparency, and self-healing characteristics were formed using a perfluorinated liquid, FC-70 (perfluorotri-n-pentylamine, $\gamma_{LV}$=17.1±0.3 mN/m) as Liquid B and a nanostructured surface made out of epoxy resin that is chemically functionalized with end-functional group of —$CF_3$ as the roughened surface.

Figure 16A:
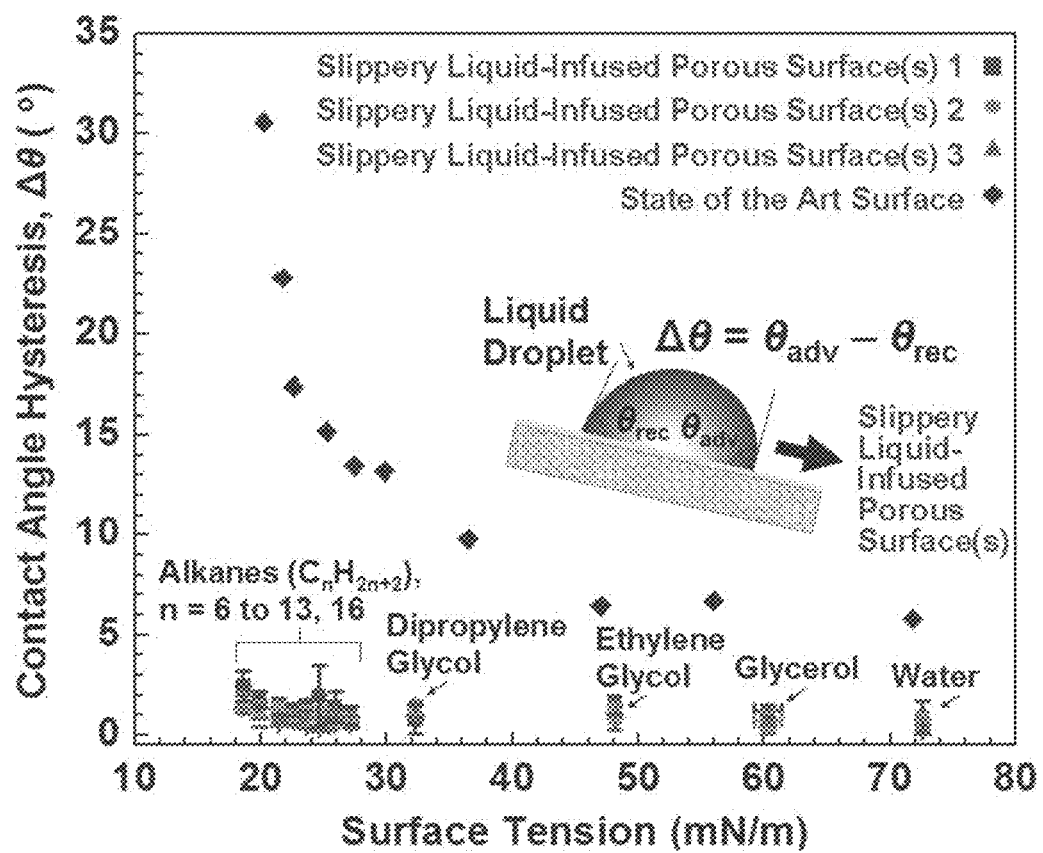
FIG. 16A is a chart of a liquid-repellency performance comparison between the surface of the present disclosure and the current state-of-the-art surface, as described in A. Tuteja, W. Choi, J. M. Mabry, G. H. McKinley, and R. E. Cohen, *Proc. Natl. Acad. Sci. USA* 105, 18200 (2008), in accordance with certain embodiments.

The fabricated surface, which is composed of a square array of cylindrical posts with feature size ~300 nm, height of the feature 500 nm-8 μm, pitch of the feature 0.9-2 μm, showed excellent repellency to a variety of test liquids (alkanes, $C_nH_{2n}+_2$, where n=5 to 16: from hexane to hexadecane, ethylene glycol, and water) from a high surface tension liquid, such as water (~72.8 mN/m), to a very low surface tension liquid, such as pentane (~17.2 mN/m). As shown in FIG. 16A, the measured contact angle hysteresis for these liquids was less than 2.5°, with a slide-off angle of less than 5°

Figure 16B:
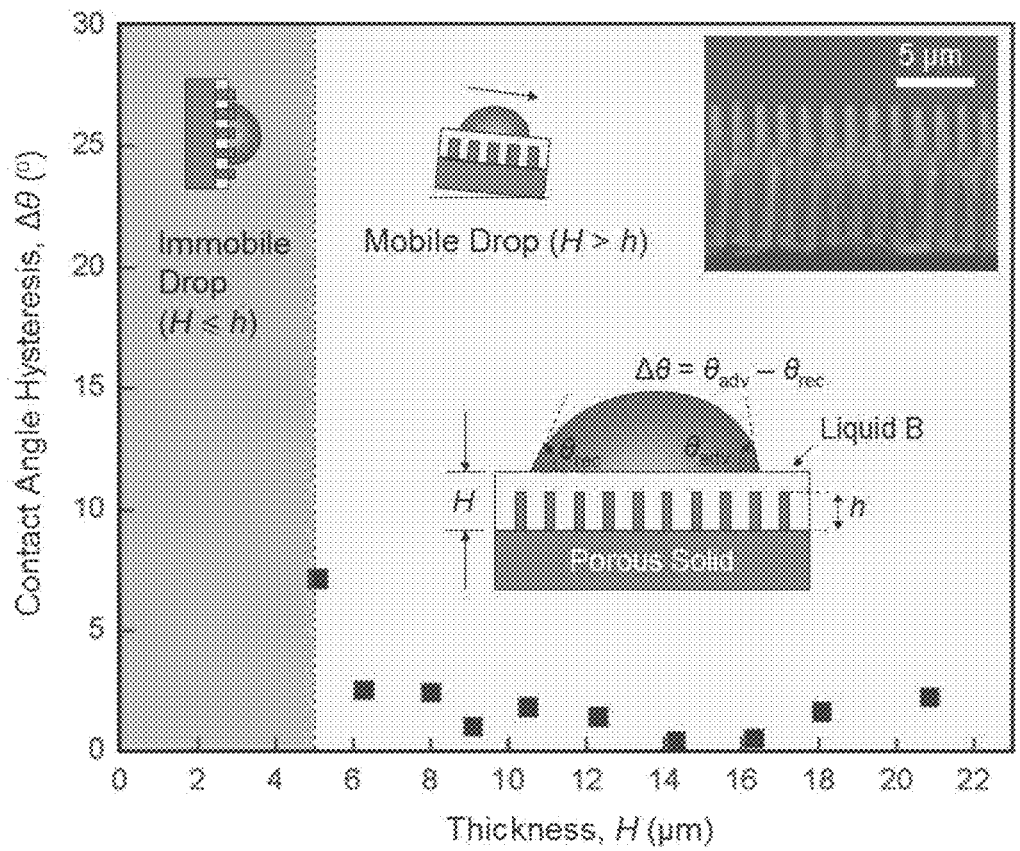
FIG. 16B shows a plot of the decane ($\gamma_{LV}$=23.6±0.1 mN/m) liquid contact angle hysteresis of the surface as a function of the thickness of the Liquid B where when the thickness of Liquid B is lower than the height of the surface textures, the liquid-slippery properties begin to diminish in accordance with certain embodiments.

The liquid-repellency of the slippery surface is insensitive to the geometries of the surface textures. As shown in FIG. 16B, the contact angle hysteresis remains less than about 2.5° when the thickness of Liquid B is greater than about 5 μm, which is about the height of the nanostructured posts.

In addition, the surface showed a very high pressure stability, which can withstand a minimum pressure difference of 5000 Pa of vertical impact for low surface tension liquids. Since the functional liquid layer has a very high solidification pressure (i.e., on the order of GPa), the operating pressure for such a surface is expected to be much higher than our current testing pressure ranges (i.e., a pressure difference on the order of 5000-10000 Pa or above). As demonstrated in Example 3, the operating pressure of the slippery surface can be as high as $6.8 \times 10^7$ Pa using a 3D porous solid material. As shown in FIG. 8, the surface can maintain its excellent liquid repellency after the liquid impacts. The measured pressure stabilities are at least 2 orders of magnitude higher than that of the current state-of-art technologies. (See, e.g., A. Tuteja, W. Choi, J. M. Mabry, G. H. McKinley, and R. E. Cohen, *Proc. Natl. Acad. Sci. USA* 105, 18200 (2008); T. P. N. Nguyen, P. Brunet, Y. Coffinier, and R. Boukherroub, *Langmuir* 26, 18369 (2010)).

Moreover, the functional liquid layer Liquid B can self-heal within orders of 100 ms to 1 s (see FIG. 13A), which is approximately four orders of magnitude faster than the current-state-of-art self-healing water-repellent surface (e.g., ~hrs). (See, e.g., Y. Li, L. Li, and J. Sung, *Angew. Chem.* 49, 6129 (2010)). Owing to this intrinsic self-healing property, the surface can restore its slippery performance even after critical damage induced by sharp objects (see FIG. 13B).

In addition, the presence of the functional liquid layer Liquid B can serve as a scratch-resistant, optical refractive index matching for any roughened solid substrates to enhance their optical transmission property. For example, when the nanostructured surface is wetted with a liquid whose refractive index, $n_{liquid}$, matches that of the solid material, $n_{solid}$, the optical transparency of the solid will be greatly enhanced (i.e., these two different materials optically appear to be the same). For example, FIG. 14B shows such a substrate with "HARVARD" written thereon and a plurality of nanostructures placed thereon. Due to the nanostructured roughened surface, the letters "HARVARD" are obscured when viewed from the top. However, by placing an index-matching infusing Liquid B on the nanostructured roughened surface, the letters "HARVARD" become much more readily viewable (see FIG. 14A). This property may be particularly important for underground oil extraction where an optically transparent, debris-free optical window may be critical for proper optical signaling in order to detect the environmental conditions. It is important to note that the use of transparent structured surface by itself cannot achieve high optical transparency due to the strong optical diffraction and scattering induced by the presence of the surface textures. As shown, where nanostructured epoxy resin (i.e., $n_{solid}$=1.519) and FC-70 (i.e., $n_{liquid}$=1.303) were used as the solid substrate and Liquid B respectively, the optical transmission through the liquid-slippery surface at the visible light spectrum (i.e., with wavelengths from 400 nm to 700 nm) is ~80%, as compared to that of air. The optical transmission of the slippery surface may be made tunable by altering the geometries of the surface textures (e.g., pore size, or pitch of the structures).

Also, by choosing suitable solid porous materials (e.g., Teflon membrane) and Liquid B (e.g., fluorinert, FC-70), enhanced optical transparency (i.e., >80%) at the near infrared range (e.g., 800 nm to 2.4 μm) can be achieved based on the concept of optical refractive index matching (FIGS. 15A to 15C). FIG. 15A schematically shows a metal block, "H" that was placed on top of a temperature-controlled plate (left), with a dry porous membrane placed over the "H") (center) where the "H" is not visible to infrared wavelengths, and with a porous membrane wetted with perfluorinated liquid (right) placed over the "H" (right) where "H" is now visible to infrared wavelengths.

FIGS. 15B and 15C indeed confirm that at 50° C. and −20° C., the dry porous membrane does not allow detection of "H" but the detection of "H" at near infrared wavelengths (greater than 800 nm) indeed becomes possible when the dry porous membrane is wetted with perfluorinated liquid. These results demonstrate the high optical transparency of the slippery surfaces at the near infrared range.

The amount of optical transmission can be made adjustable by tuning the physical geometries/porosities of the porous solids, as well as the thickness of the solid substrates. Such a slippery surface can be used as self-cleaning optical windows for infrared imaging, solar panels, and the like.

Example 2

Exceptional pressure stability of the slippery surface is demonstrated with the use of a perfluorinated liquid infiltrated Teflon porous membrane. To demonstrate this, 2 μL of decane was placed on a 5 mm×5 mm Teflon porous membrane (Sterlitech, 200 nm pore size, unlaminated) infiltrated with 1.5 μL DuPont Krytox 103, where the membrane was glued onto a custom-made metal platform for the sample transfer into the high pressure chamber. During the operation of the high pressure cell, pressurized nitrogen gas was injected into a stainless steel chamber connected to a calibrated pressure gauge for pressure monitoring. The rate of pressure change was monitored during the process. Once the targeted pressure was reached, the sliding angle of the decane droplet was measured by tilting the chamber with respect to the horizontal until the droplet started to slide.

It was observed that the sliding angle of the decane droplet was <5° even under a pressured environment of about $6.8 \times 10^7$ Pa (about 680 atmospheric pressure). This further shows that the liquid repellency of the surface can be maintained under very high pressure condition. The high pressure stability described in this Example and the optical transparency features described in Example 1 can be combined, when necessary, for certain applications.

Example 3

To demonstrate that the slippery surface can be formed over/on non-planar surfaces, a Teflon membrane wetted with fluorinert, FC-70 was glued onto a curved aluminum surface. Two control surfaces were used for comparison, one was a non-planar bare aluminum surface, and the other was a Teflon membrane without fluorinert that was glued onto a non-planar aluminum surface. Drops of crude oil (i.e., paraffinic extra-light crude oil) were applied onto these surfaces to verify their liquid repellency performance.

Figure 19A:
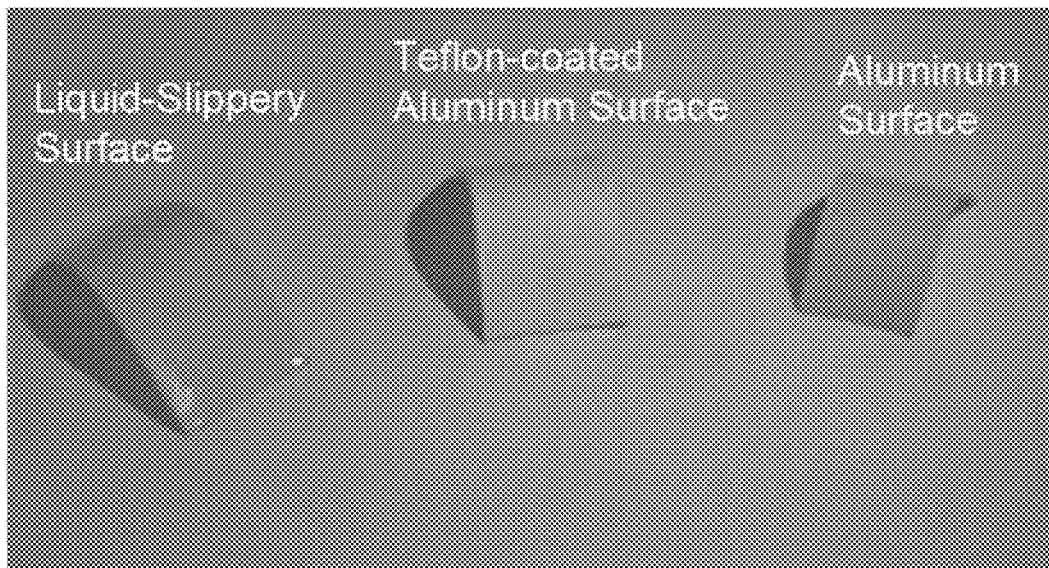
FIGS. 19A and 19B show images of improved repellency of the slippery surface of the present disclosure for crude oil (i.e., paraffinic light crude oil) as compared to aluminum and Teflon coated aluminum surface in accordance with certain embodiments.
Figure 19B:
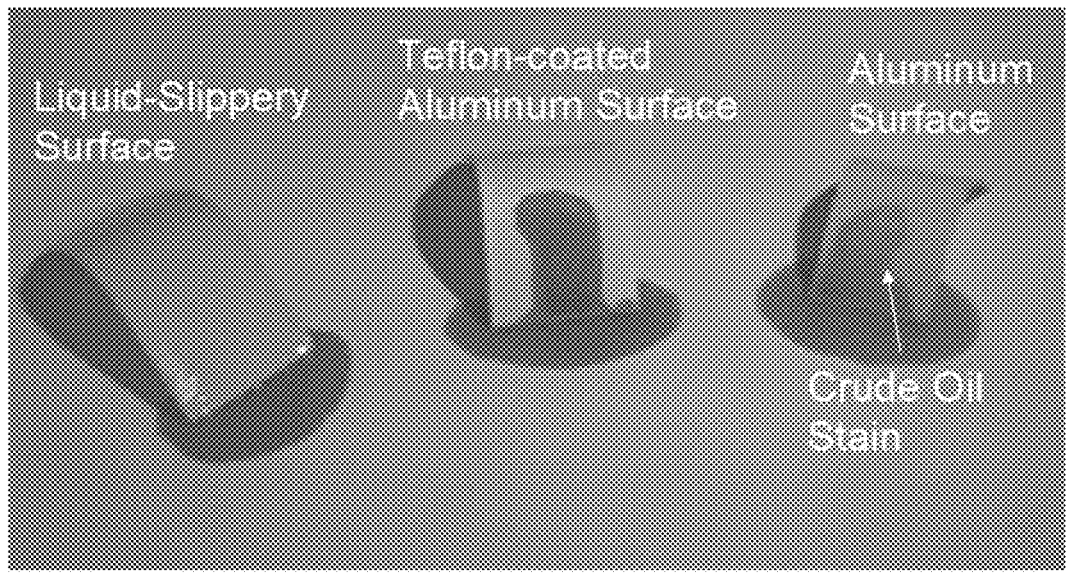

FIG. 19A to 19B are images demonstrating the superior repellency of the slippery surface of the present disclosure for crude oil (i.e., paraffinic light crude oil) as compared to aluminum and Teflon coated aluminum. As shown, crude oil completely slides off the slippery surface leaving it pristine clean, while the oil adheres to both the bare aluminum surface and Teflon coated aluminum surface leaving black stains.

Example 4

Owing to the slippery nature of the surface of the present disclosure, the surface can be utilized to remove solidified fluids (e.g., ice/frost) at a much reduced energy input. Specifically, Solid A that is larger than a characteristic size can slide off from a tilted surface of Liquid B by gravity. For example, in the case where Object A is water and Liquid B is FC-70, the solidified water formed at near its freezing point can slide off from FC-70 at a tilting angle >70°, when the characteristic size of the ice is about three times the size of the capillary length of water (i.e., ~2 mm at room conditions) (FIG. 17). FIGS. 17A-17C show comparison of the ice slippery behaviors between the surface of the present disclosure and a flat epoxy surface. FIGS. 17D-17F show comparison of the ice slippery behaviors between the surface of the present disclosure and a nanostructured surface. In both of the scenarios, ice was pinned on the flat epoxy and nanostructured surfaces, whereas ice can slide from the surface of the present disclosure by tilting the substrate at >70°. Moreover, the surface of the present disclosure is clear, does not exhibit any fogging while the other flat epoxy and nanostructured surfaces are foggy and optically diffuse.

Additionally, the ultra-smooth Liquid B surface reduces its adhesion with Solid A at the plane normal to the substrate surface (FIG. 18). For example, the estimated adhesion strength of Solid A, such as ice, formed at near its freezing point on the surface of Liquid B, such as FC-70 is on the order of 0.5 kPa. Such a low adhesion strength is at least 2 orders of magnitude lower than that reported in the literature regarding ice adhesion on flat surfaces (e.g., Adam J. Meuler, J. David Smith, Kripa K. Varanasi, Joseph M. Mabry, Gareth H. McKinley, and Robert E. Cohen, *ACS Appl. Mater.* 2, 3100 (2010)) and superhydrophobic surfaces (e.g., Kripa K. Varanasi, Tao Deng, J. David Smith, Ming Hsu, Nitin Bhate, *Appl. Phys. Lett.* 97, 234102 (2010)).

Moreover, the liquid-slippery surface shows resistance to fog and frost formation at a temperature lower than those of the flat and superhydrophobic surfaces under low humidity conditions. For example, under the room conditions of ~20% relative humidity at ~24° C., the super-cooled liquid-slippery surface (i.e., Solid=epoxy resin; Liquid B=FC-70) remain fog-free and frost-free at about −10° C. in at least 90% of the surface, whereas those of the silanized epoxy flat and superhydrophobic surfaces were decorated with fog and frost completely at −5° C.

Furthermore, the liquid-slippery surface can be completely defrosted at a temperature lower than those of the flat and superhydrophobic surfaces, and restore its slippery function completely after the frosting-defrosting cycle. For example, under the room conditions of ~20% relative humidity at ~24° C., the super-cooled liquid slippery surface can be completely defrosted by holding the surface at a vertical position while heating up the substrate temperature from −20° C. to 5° C., whereas those of the silanized epoxy flat and superhydrophobic surfaces were still covered with frost completely under these conditions. The high defrosting efficiency in the liquid slippery surface, as compared to the other surfaces, may be attributed to the fact that the liquid-slippery function is restored after the defrosting cycle, thereby repelling the water condensates on the liquid-slippery surface. On the contrary, the superhydrophobic surface after the defrosting cycle loses its water-repellency function, which reduces its defrosting efficiency as compared to the liquid-slippery surface. On the latter, the fully or even partially melted droplets slide instantaneously off the surface completely upon mild agitation or subjected to air flow, thus reducing the required time and energy inputs at the defrosting cycle.

Example 5

Figure 20A:
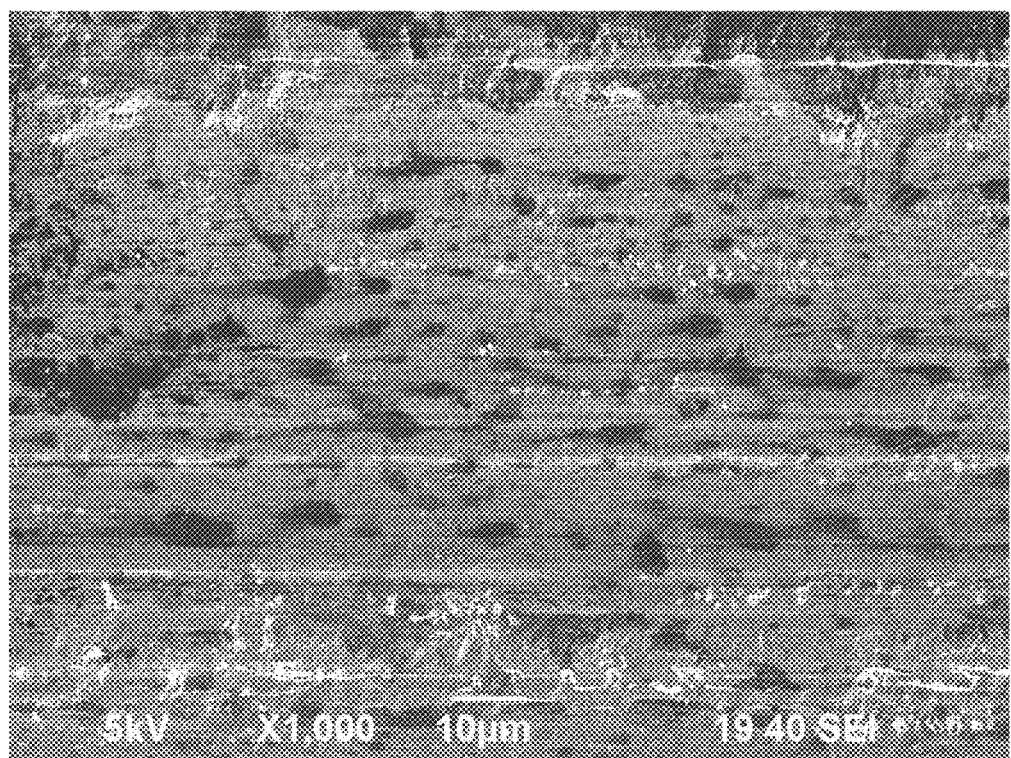
FIG. 20A shows an SEM image of the Al 1100 alloy surface.

To further demonstrate the potential of slippery liquid-infused porous surface(s) to be formed on irregular surfaces, Al 1100 alloy, generally used as the coil material in refrigerator systems, was cut out from a refrigerator coil, then cleaned in acetone for 15 minutes in an ultrasonic bath. FIG. 20A shows an SEM image of the Al 1100 alloy surface.

Electrochemical deposition of polypyrrole was carried out, under conditions that provide both a primary and secondary structure in a single layer (see FIG. 20B), referred to in this example as a "first layer." To deposit the first layer, an electrodeposition bath was prepared containing 0.1 M pyrrole, 0.1 M dodecylbenzenesulfonic acid, and sodium salt (SDBS) in deionized water. Pyrrole was purified by filtering through an alumina column and used immediately. The pH of the 0.1 M SDBS was made slightly acidic (pH ~6.52) as it was realized that if the pH of SDBS is basic, the deposition becomes very slow and non-uniform on the Al 1100 alloy.

Standard three-electrode configuration was used for the electrodeposition using a potentiostat. A silver/silver chloride (saturated with NaCl) reference electrode was used. A large surface area platinum electrode (10 cm×10 cm, 100 mesh) was used as a counter electrode. It is important to have a high surface area counter electrode to achieve a uniform coating. It is also important to have the deposition bath constantly stirred for uniform deposition. Other types of counter electrodes (e.g. platinized titanium mesh) may be used as a counter electrode. A salt bridge may be also used if the counter and reference electrodes need to be separated from the main deposition bath.

The cleaned substrate was immersed in the deposition bath. After soaking the Al substrate for 10 minutes, the electrodeposition was performed by applying a constant potential of 0.9-1.0 V vs. Ag/AgCl for 0-600 seconds (i.e.

chronoamperometry). After electrodeposition of the first layer, the substrate was rinsed with deionized water and dried by blowing air.

The counter electrode was placed vertically along the curvature of the container. When the substrate was placed vertically, the deposition took place on the surface facing the counter electrode, then the backside. When the substrate was placed horizontally, the deposition took place on the bottom surface, then the top surface.

Figure 20B:
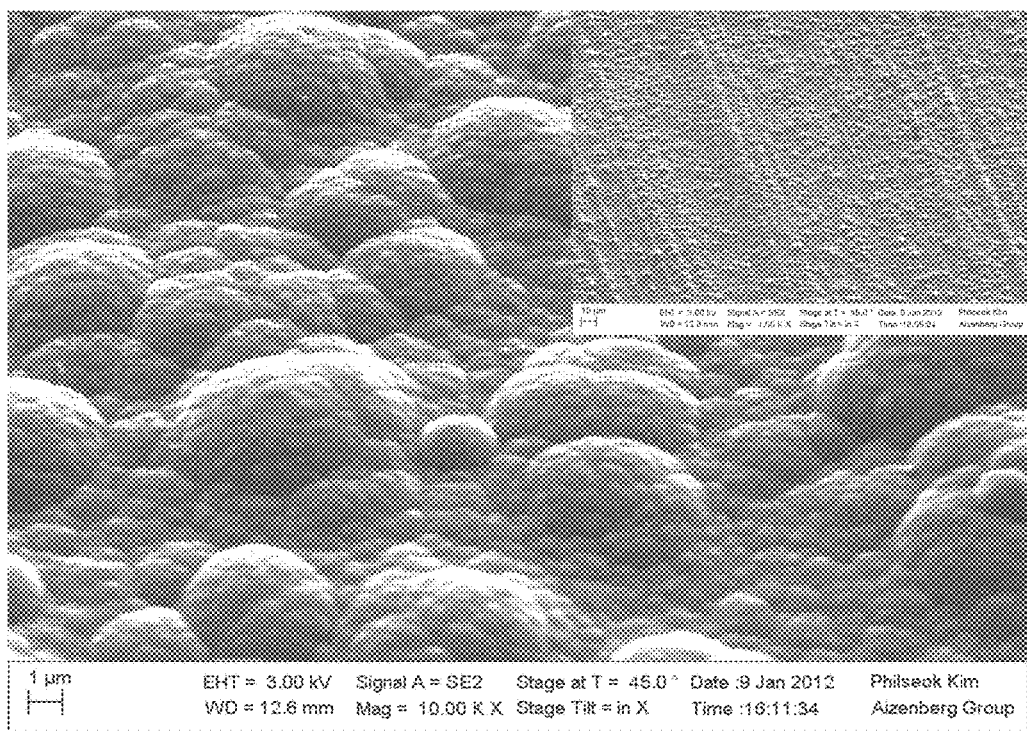
FIG. 20B shows an SEM image of a plurality of bumps (secondary structure) along with a plurality of fine scale protrusions on each of the bump surfaces (primary structure) formed over the Al surface in accordance with certain embodiments.

FIG. 20B shows an SEM image of the first layer. As shown, the deposited first layer includes a plurality of bumps (secondary structure) along with a plurality of fine scale protrusions on each of the bump surfaces (primary structure). Accordingly, both the primary and secondary structures were deposited simultaneously by selecting the appropriate electrodeposition conditions.

A second electrochemical deposition was carried out. The second electrodeposition bath contained 0.2 M phosphate buffer (pH=6-7), 0.01-0.1 M perchlorate (e.g. LiClO4) solution and 0.08-0.1 M pyrrole in deionized water. Nitrogen was bubbled through the solution prior to use. In some instances, additional templating agents may be added (e.g. soluble starch, heparin, polystyrenesulfone, etc.).

Figure 6A:
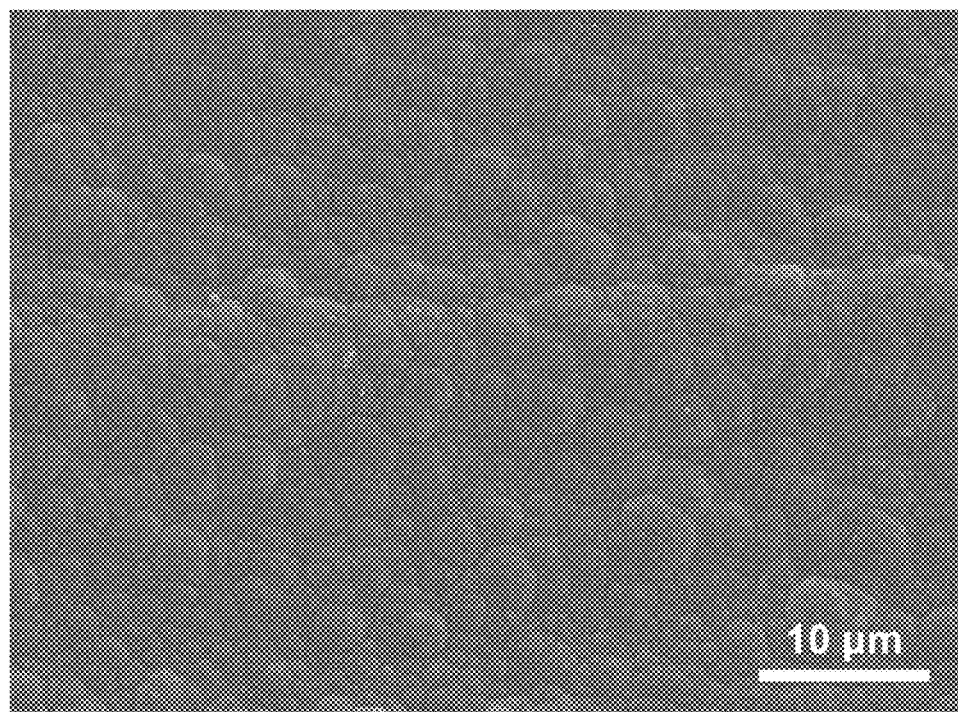
FIG. 6A shows an SEM image of an electrodeposited polymer having a morphology that is similar to a cauliflower.
Figure 6B:
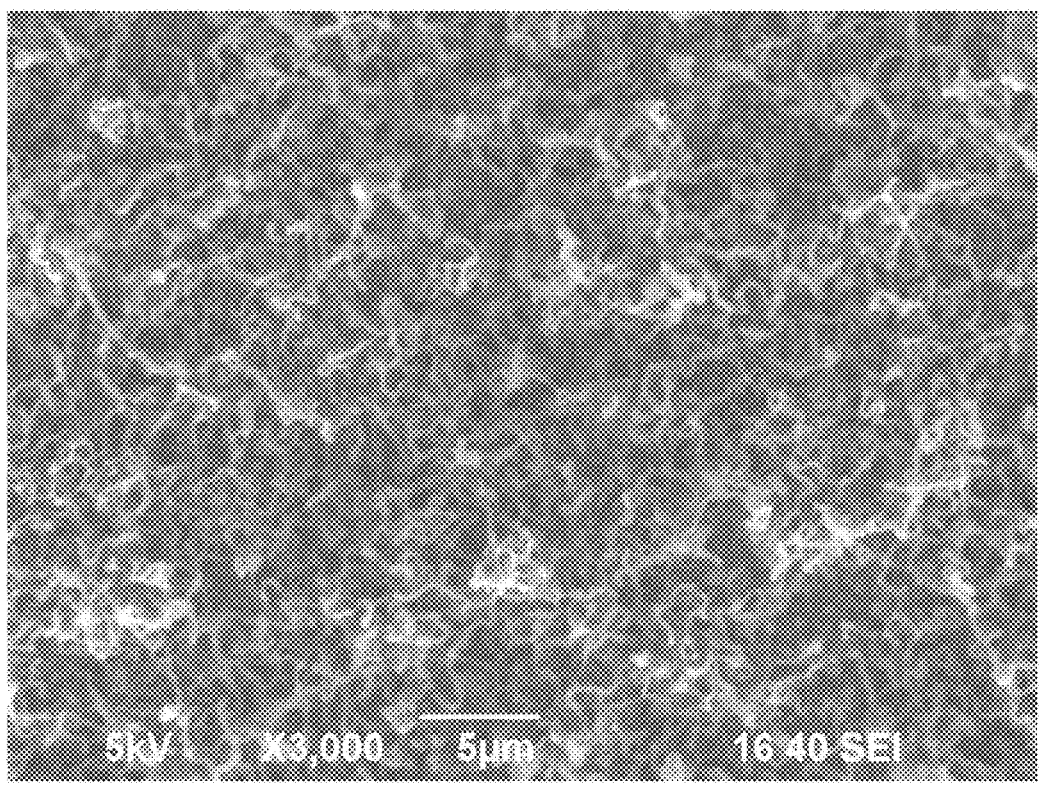
FIG. 6B shows an SEM image of an electrodeposited polymer having a nanofibrillar morphology in accordance with certain embodiments.
Figure 6C:
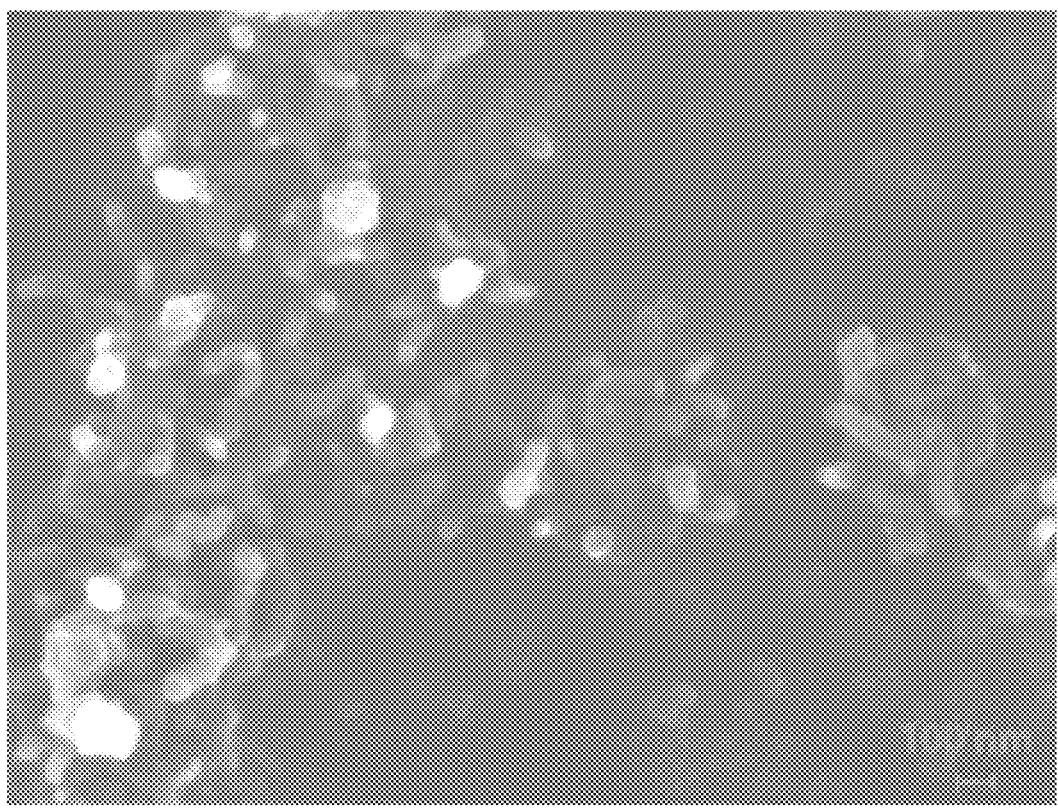
FIG. 6C shows an SEM image of an electrodeposited polymer having a rod-like morphology in accordance with certain embodiments.
Figure 6D:
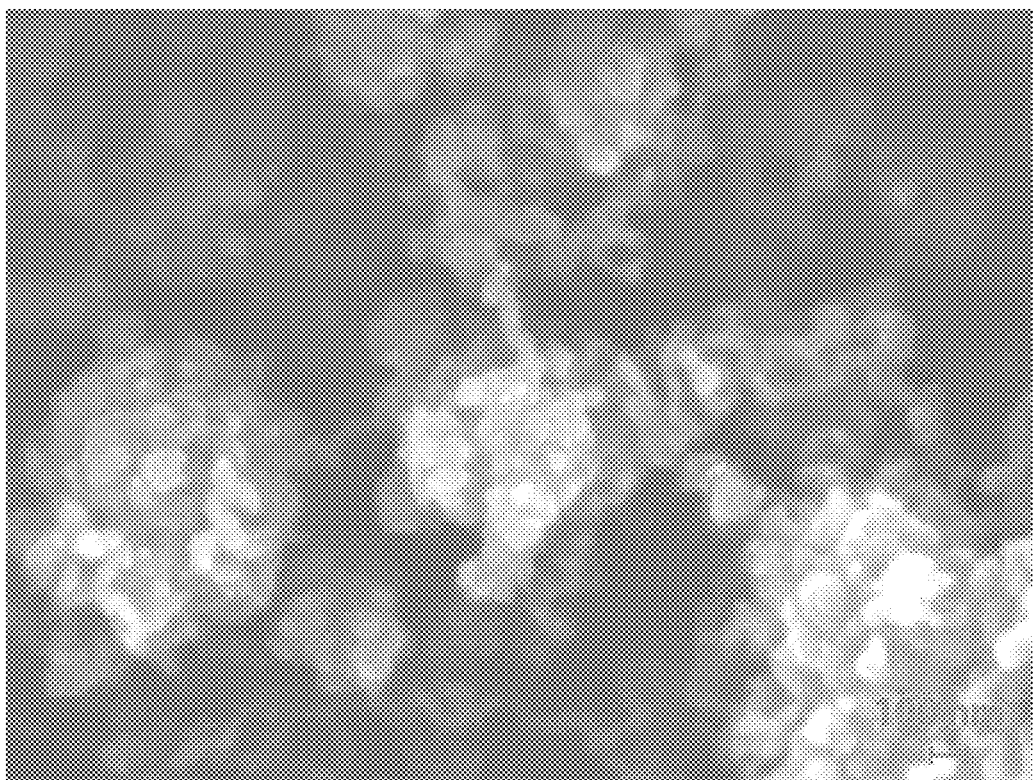
FIG. 6D shows an SEM image of an electrodeposited polymer having a morphology of overgrown polymers in accordance with certain embodiments.
Figure 6E:
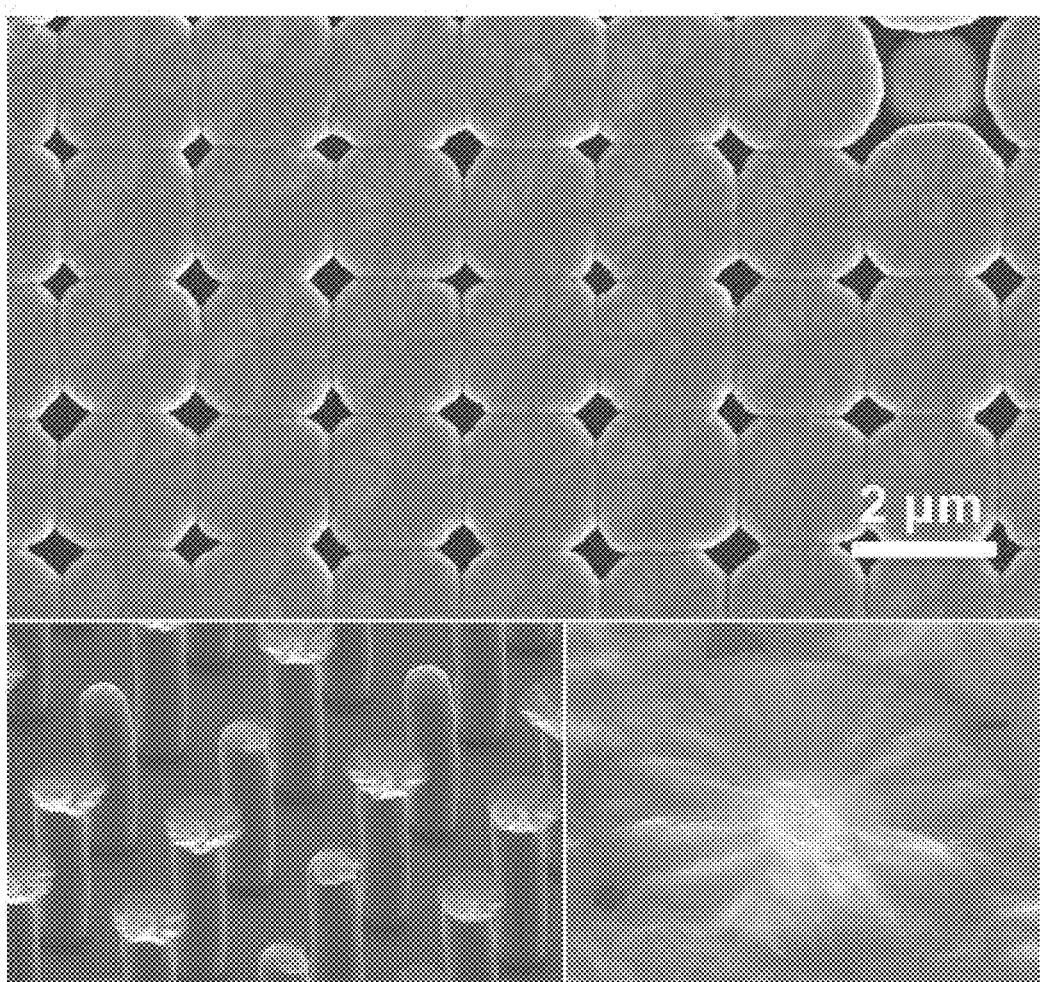
FIG. 6E shows an SEM image of an electrodeposited polymer formed on microposts resulting in a mushroom-like morphology in accordance with certain embodiments.
Figure 6F:
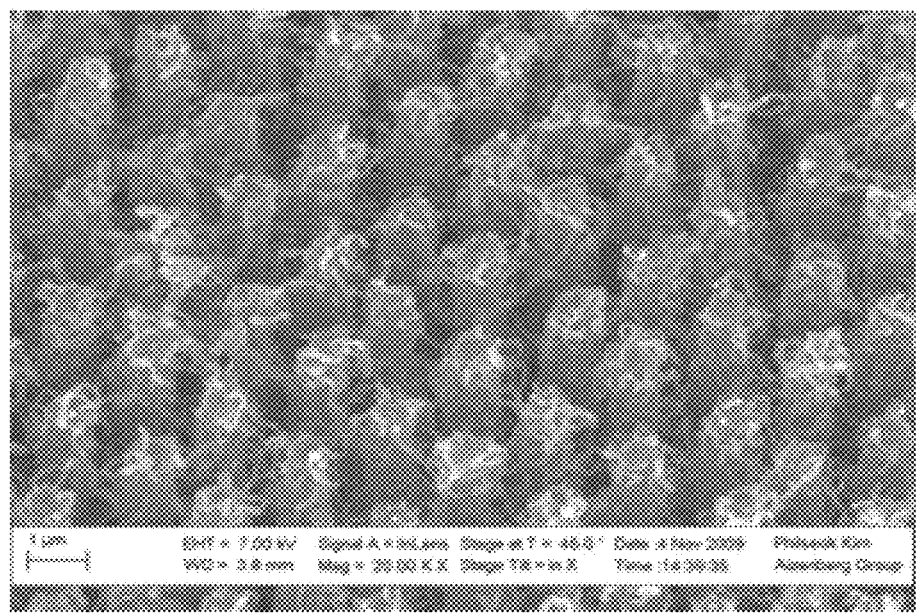
FIG. 6F shows an SEM image of the fibrous surface fabricated on an array of raised features, to form a hierarchical structure of roughness at two different length scales in accordance with certain embodiments.

It should be noted that deposition directly on Al 1100 surface using the second electrodeposition bath did not work as the aluminum at the anode (working electrode) was oxidized before the pyrrole monomer was able to oxidize and polymerize. The oxidized aluminum (aluminum ion) tends to react with the phosphate anion which leads to white precipitating salts on the surface of the Al electrode. However, carrying out the electrodeposition using the same conditions for Al 1100 having the first layer described above, a second layer of polypyrrole was successfully deposited, to form nanofibrils over the first layer. FIG. 6B shows an SEM image of the polypyrrole nanofibrils formed over the first layer.

Figure 20C:
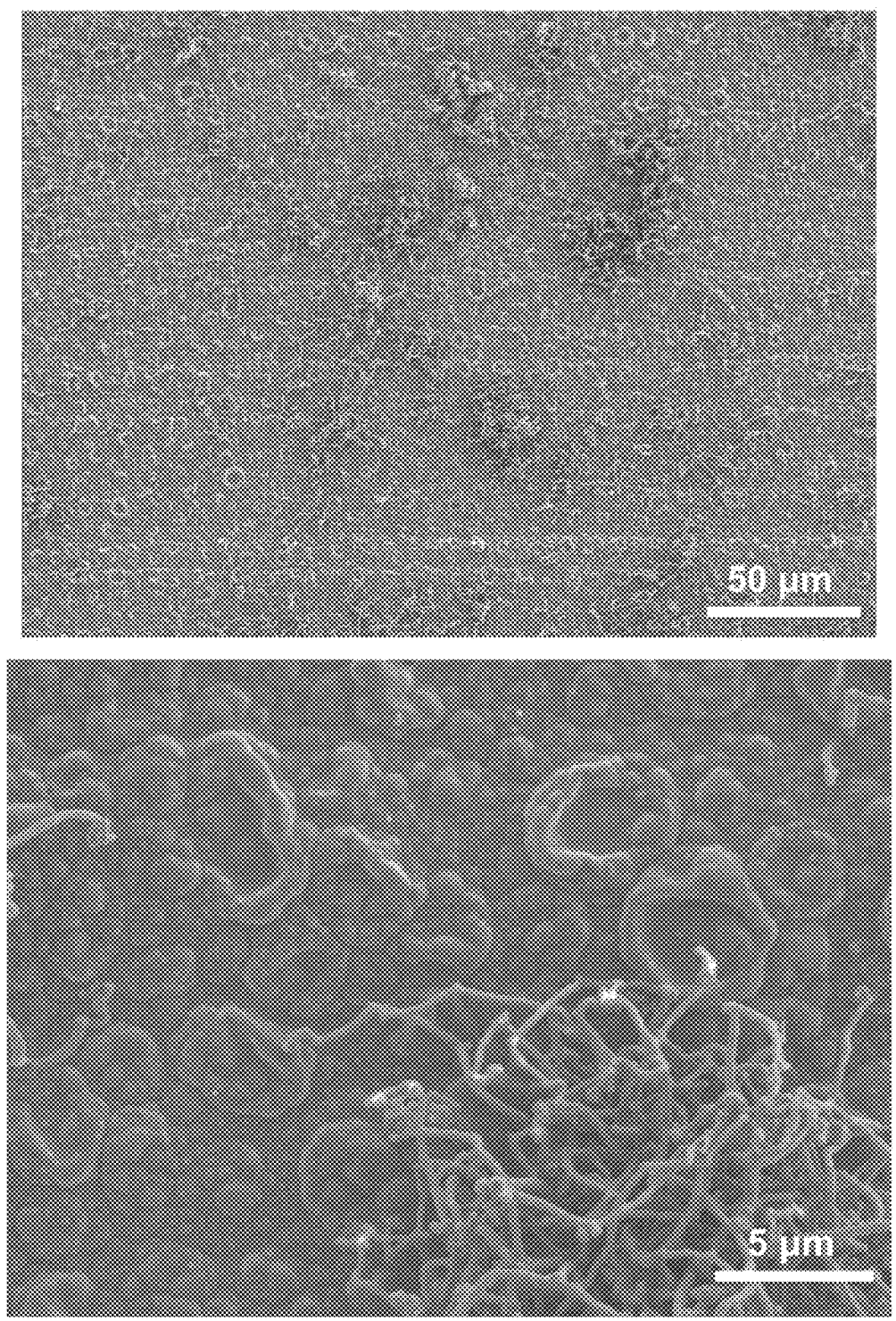
FIG. 20C shows different SEM images of different morphologies that can be developed by altering electrodeposition conditions in accordance with certain embodiments.

If the concentration of pyrrole monomer is increase to 0.12 M in the second bath, toroid shaped morphology is formed, along with a lower density of nanofibers. Moreover, as shown in FIG. 20C, the plurality of fine scale protrusions are also present. Accordingly, the technique illustrates that primary, secondary, and tertiary structures can all be formed in a single process.

All samples were fluorinated by placing the samples in a vacuum desiccator with a few drops of heptadecafluoro-1,1,2,2-tetrahydrooctyl trichlorosilane placed in a small vial for more than 24 hours.

Example 6

Anti-sticking surfaces that resist adhesion for natural and synthetic adhesives have broad technological implications from pest control to military defense. Adhesion between surfaces is a function of interfacial energy, which is the interplay between molecular interactions at the interface. Fundamentally, adhesion energy between a liquid-solid interface (~O(10 mJ/m$^2$) is about 1-2 orders of magnitude lower than that of the solid-solid interface (~O(100-1000 mJ/m$^2$). In addition, liquid surface is inherently mobile (i.e., the surface molecules are free to move), therefore the presence of the Liquid B on our slippery surfaces results in greatly reduced adhesion for a broad variety of natural and synthetic adhesives.

Figure 22:
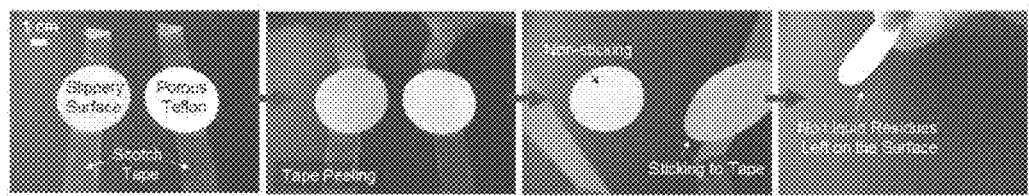
FIG. 22 shows a demonstration of anti-sticking property of a slippery surface against synthetic dry adhesive (i.e., SCOTCH tape), as compared to a porous Teflon surface in accordance with certain embodiments.

The slippery surfaces produced in accordance with the present methods have greatly reduced adhesion to synthetic dry adhesives, such as Scotch® tape, as compared to other existing surfaces (FIG. 22). It is important to note that solid Teflon surface is known to be highly anti-adhesive; however its anti-sticking performance is still inferior to the slippery surfaces produced in accordance with the present methods. In addition, the slippery surfaces produced in accordance with the present methods exhibit highly non-sticking property towards synthetic liquid adhesives, such as Krazy glue (cyanoacrylate-based adhesive) and 2-part epoxy glue, as compared to other existing surfaces.

Figure 23:
FIG. 23 shows a series of images demonstrating the anti-sticking property of a slippery surface against underwater adhesives, as compared to other surfaces in accordance with certain embodiments.

The slippery surfaces produced in accordance with the present methods can also operate in underwater environments and feature low adhesion to commercially available underwater adhesives, such as epoxy putty (FIG. 23).

Example 7

Common practices for pest control have been predominantly focused on the use of chemicals, such as pesticides. While these methods have been proven effective in most scenarios, these chemicals, due to their toxicity, may bring adverse effects to the environment and human health. As a result, effective and environmentally friendly physical methods that can prevent the intrusion of insects (e.g., cockroach, fire ants) into indoor or outdoor infrastructure are highly desirable. Some of the current physical methods for pest control include the use of sticking surfaces to immobilize insects (see, e.g., US Patent Application No. 2004/0244703; US Patent Application No. 2006/0185224 A1); the use of high density polymeric geotexiles to prevent the intrusion of insects (see, e.g., US Patent Application No. 2003/0166372); the use of electrostatic charged surfaces to trap flying or crawling insects (see, e.g., U.S. Pat. No. 6,041,543); the use of electric grid traps that utilize near-UV light for attracting insects toward a high voltage source (see, e.g., U.S. Pat. No. 3,491,478); and the use of a "no-exit trap" such as the Victorian fly trap, in which the insects are trapped within a dome-shaped glass with a central opening.

Figure 24:
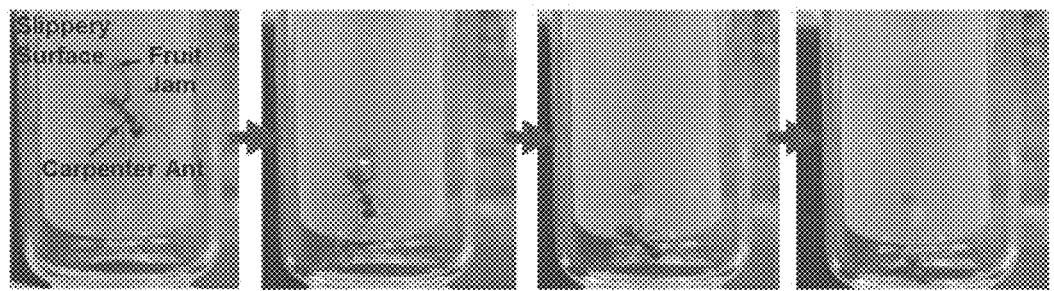
FIG. 24 shows a series of images demonstrating anti-sticking property of a slippery surface to natural adhesives secreted by a carpenter ant and a viscous fluid (i.e., fruit jam) in accordance with certain embodiments.

The present disclosure presents an effective physical means to prevent the intrusion of trapping flying or crawling insects when applied to the surfaces of indoor/outdoor infrastructure. The slippery surfaces produced in accordance with the present methods are repellent to insects, such as ants, which use natural oil-based adhesive for attachment on smooth surfaces. FIG. 24 is a series of images demonstrating the anti-sticking property of a slippery surface with respect to a carpenter ant. The ant typically utilizes secretion of natural adhesives as well as mechanical hooks to climb a surface; however, the ant is unable to hold onto the slippery surface and climb. The image further includes a viscous, sticky fluid (i.e., fruit jam) that readily slides off the slippery surface.

Example 8

Surfaces that show anti-wetting and anti-sticking behaviors against water-based or oil-based spray paints have enormous commercial values. For example, it is estimated that over $2.6 billion are spent annually to clean graffiti off public infrastructure worldwide. Conventional lotus-effect-based approaches for liquid resistant coatings have limited effectiveness against liquid spray paints, particularly for oil-based paints. A fundamental reason for this is that spray paints consist of very fine liquid droplets (i.e., average drop-size ≤500 μm), which can easily penetrate into the air pockets trapped in between the solid textures. In addition, oil-based spray paint consists of mixtures of liquids/vapor at very low surface tensions ($\gamma_{LV}$≤25 mN/m), which tend to enhance the solid wettability and makes the task of repelling these liquids extremely challenging. To this end, new liquid repellent technology is highly essential for anti-graffiti measures.

Fundamentally, liquid repellency is dictated by contact angle hysteresis (CAH) of liquid droplets. CAH is defined as the difference between the upper and lower limits of liquid contact angles of a surface, as denoted by advancing contact angle, BA, and receding contact angle, $\theta_R$, respectively (i.e., $\Delta\theta=\theta_A-\theta_R$). When a liquid droplet (e.g., a drop of paint) is placed on an inclined surface, the mobility of the droplet is determined by the balance between gravitational force, $F_G$, and the retention force, $F_R$, of the droplet induced by CAH, which can be quantitatively expressed as $F_R=w\gamma_{LV}(\cos\theta_R-\cos\theta_A)=F_G=mg\sin\alpha$, where m and w are the mass and width of the liquid droplet, respectively; g is the gravity; $\gamma_{LV}$ is the liquid surface tension; and a is the sliding angle of the droplet. To enhance liquid repellency of a surface resulting in the ability of the droplets to slide or roll off the surface (i.e., small $\alpha$), the CAH has to be minimized, and ideally approach zero (i.e., $\Delta\theta\approx 0$). As the origins of CAH are attributed to liquid pinning at sites of physical roughness or chemical heterogeneities of the surface, creating a surface that is free from these artifacts is the key to minimizing CAH, thereby leading to extreme liquid repellency.

The slippery surfaces produced in accordance with the present methods have very low CAH (i.e., $\Delta\theta\leq 2.5°$) against liquids with a broad range of surface tensions. The surfaces are capable of removing liquid droplets (volume $\geq 2$ µL) at low sliding angle (i.e., $\alpha\leq 5°$). The estimated retention force of the surfaces against low-surface-tension liquids (i.e., $\gamma_{LV}\leq 25$ mN/m) is $0.83\pm 0.22$ µN for liquid volume of ~5 µL. Such a low retention force is nearly an order of magnitude lower than the current state-of-the-art omniphobic surfaces at similar liquid volume. Based on these performances, the maximum size of liquid droplets that can retain on the surface is $\leq 500$ µm, which is considerably smaller than any synthetic liquid repellent surfaces for low-surface-tension liquids. Experiments performed using a commercial oil-based spray paint (e.g., Krylon® Fusion for Plastic®, which consists of a mixture of propane, butane, naphtha, toluene, ethylbenzene, xylene, actone, methyl isobutyl ketone, and titanium dioxide) on the slippery surfaces have demonstrated that liquid droplets that are larger than order of 500 µm slid off from the surfaces (FIG. 25), whereas lotus-effect-based surfaces failed to repel the oil paint and were uniformly coated. The tiny residual paint droplets (i.e., $\leq 500$ µm) that were left on the slippery surfaces can be removed easily by commercially available organic solvents/cleaners, rendering a pristine clean surface.

Example 9 slippery liquid-infused porous surface(s) can help to protect the surface from a wide range of particulate contaminants by allowing self-cleaning using a broad assortment of fluids that collect and remove the particles from the surface. For slippery liquid-infused porous surface(s) composed of a perfluorinated fluid and fluorinated substrate, common dust particles, such as carbon-based particles (e.g., coal dust) or silica-based particles (e.g., sand), can be removed by conventional fluids (e.g., water or ethanol) through self-cleaning (FIGS. 26A and 26B).

Dust particles that prefer to be wetted by certain types of Liquid B may be difficult to remove. While these microparticles are wetted and stick to Liquid B, the microparticles can be completely over-coated by Liquid B, and as a result, the wetting property of the surface remains unaffected as these particles will only contribute to the "roughness" and "porosity" of the substrate and be wicked by Liquid B such that any immiscible foreign liquids (Liquid A) can "float" on top of the over-coated Liquid B layer.

Example 10

An aluminum surface can be roughened for use in slippery liquid-infused porous surface(s) by mechanical or (electro)chemical methods followed by chemical modification using a reactive polyfluorinated long-chain reagent.

Al Alloys

Aluminum alloys 5052, 6061-T6, and 2024 were used to demonstrate surface roughening by mechanical or (electro) chemical methods followed by chemical modification. The typical chemical compositions of these alloys are shown in Table 5.

TABLE 5

Chemical Compositions of the Aluminum Alloys Used.

| Component | Al 5052 Wt % | Al 2024 Wt % | Al6061-T6 Wt % |
|---|---|---|---|
| Al | 95.7-97.7 | 90.7-94.7 | 95.8-98.6 |
| Cr | 0.15-0.35 | Max 0.1 | 0.04-0.35 |
| Cu | Max 0.1 | 3.8-4.9 | 0.15-0.4 |
| Fe | Max 0.4 | Max 0.5 | Max 0.7 |
| Mg | 2.2-2.8 | 1.2-1.8 | 0.8-1.2 |
| Mn | Max 0.1 | 0.3-0.9 | Max 0.15 |
| Si | Max 0.25 | Max 0.5 | 0.4-0.8 |
| Ti | — | Max 0.15 | Max 0.15 |
| Zn | Max 0.1 | Max 0.25 | Max 0.25 |
| Other, each | Max 0.05 | Max 0.05 | Max 0.05 |
| Other, total | Max 0.15 | Max 0.15 | Max 0.15 |

Bead Blasting slippery liquid-infused porous surface(s) samples were prepared from the alloys. Sample 1, and a first control ("Control #1") were made of Al 5052. Samples 2, 3, 4 were made of Al 2024. Samples 5, 5-1, and a second control ("Control #5") were made of Al 6061-T6. The samples were subjected to bead blasting as shown in Table 6. The size of the aluminum samples used in the bead blasting and profile measurements was 2"W×2"H. For further surface treatments, the aluminum samples were cut in half to produce 1"W×2"H plates.

TABLE 6

Bead blasting materials Used and Their sources.

| Sample # | Bead material | Particle Size, µm (Grit) | In-house/ outsourced |
|---|---|---|---|
| 1 | Aluminum oxide | 102 (120) | In-house |
| 2 | Glass (Ballotini) | 212~150 | RPAbrasives, Milton NH |
| 3 | Glass (Ballotini) | 150~90 | RPAbrasives, Milton NH |
| 4 | Glass (Ballotini) | 90~45 | RPAbrasives, Milton NH |
| 5, 5-1 | Aluminum oxide | 89 (150) | In-house |

Roughness Measurements

The samples were prepared for surface-roughness measurements by being sonicated in acetone for 5 min and blow dried in nitrogen stream. The roughness of the aluminum alloy samples was then measured using a profilometer Veeco Dektak 6M. The conditions under which the measurements were taken are as follows.

Roughness Standard: ANSI B46.1
Stylus Radius: 12.5 um
Scan length: 2000 μm=2 mm
Num Pts: 6000
Measurement Range:2620 kA=262
Stylus Force: 15 mg
Number of measurements: 2/sample
Location1: Center
Location2: ½ distance between center and edge The roughness and waviness data for the samples, including the non-blasted controls, are shown in Table 7.

TABLE 7

Roughness and Waviness Data Measured for The Bead Blasted Samples and Non-Blasted Controls

| Sample No. | Average Roughness Ra μm | RMS Roughness Rq μm | Average Waviness Wa μm | RMA Waviness Wq μm |
|---|---|---|---|---|
| 1 | 1.904 | 2.435 | 0.7855 | 0.9824 |
| 2 | 2.714 | 3.3144 | 2.0738 | 2.6439 |
| 3 | 2.3616 | 3.0291 | 1.3095 | 1.57466 |
| 4 | 1.3539 | 1.6767 | 0.91194 | 1.0698 |
| 5 | 3.3058 | 4.5242 | 1.8744 | 2.442575 |
| 6 | 3.403 | 4.421 | 1.7680 | 2.190 |
| Control #1 | 0.1570 | 0.204 | 0.1783 | 0.2185 |
| Control #5 | 0.3016 | 0.4100 | 0.2848 | 0.3595 |
| Calibration Si Mech. Grade | 0.001975 | 0.000247 | 0.00328 | 0.003975 |

As seen from Table 7, after bead blasting, the samples exhibited degrees of roughness ranging from Ra 1.35 μm to 3.4 μm. The roughness of samples 5 and 6, which were prepared in the same way and from the same material, was very similar, as expected. The non-blasted controls were about an order of magnitude less rough than the bead-blasted samples. Samples 2, 3, 4, all made of the same Al alloy 2024, were treated similarly, using Ballotini glass bead sizes that decreased from sample 2 to sample 4. Within this series of samples, the roughness and waviness followed the same pattern, that is it decreased monotonously from sample 2 to sample 4. The waviness of bead-blasted samples 1, 5, 6, also increased compared to their respective controls, Control #1 and Control #5.

Based on the roughness and waviness data of the bead-blasted samples, the modified surfaces were shown to have microstructures ranging in size from 1 to 4 microns. The differences in roughness of the samples were not significant. Thus, it was hypothesized that the difference between the samples may show up in their performance at the chemical surface treatment steps, necessary for creating a slippery liquid-infused porous surface(s) surface. The aluminum alloy, of which samples 2-4 were made, contained significant amounts of copper, which render this alloy less reactive towards carboxyl functionalities of Krytox 157FSH. Sample 2, which was refluxed longer (4 h) than samples 3 and 4 (3 h), exhibited higher contact angles, which suggests that the functionalization of less reactive aluminum alloy such as 2024 does occur, but at a slower rate than for more reactive alloys (e.g., aluminum alloy 5052 and 6061).

Contact Angle Measurements

Contact angle measurements were performed on alloys held horizontally and at room temperature. A CAM101 (KSV Instruments LTD) instrument and a Millipore grade water were used to take the measurements. The values for the samples and the non-blasted controls, presented in Table 8, are for the left, right, and average angles for each location measured. For each sample, one to three locations were tested.

TABLE 8

Contact Angle Data Measured for the Bead Blasted Samples and Non-Blasted Controls

| Samples/ Measurement Position | CA (L), deg | CA(R), deg | CA(M), deg | Comment |
|---|---|---|---|---|
| 1_center | 139.876 | 141.756 | 140.816 | |
| 1_edge | 139.482 | 139.643 | 139.563 | |
| 2_center | 124.537 | 120.806 | 122.671 | Refluxed 4 h b) |
| 2_pitted edge | 122.904 | 119.592 | 121.248 | Refluxed 4 h b) |
| 3_center | 82.995 | 87.341 | 85.168 | |
| 3_edge | 93.062 | 96.344 | 94.703 | |
| 4_center | 83.849 | 85.334 | 84.591 | |
| 4_sl.pitted center | 101.923 | 104.047 | 102.985 | |
| 4_edge | 77.734 | 79.274 | 78.504 | |
| 5_pitted center | 123.698 | 122.594 | 123.146 | |
| 5_edge | 142.199 | 139.876 | 141.037 | |
| 5-1_center a) | 143.677 | 145.245 | 144.461 | b) |
| Control #1_center | 117.113 | 120.852 | 118.982 | b) |
| Control #1_edge | 111.258 | 112.873 | 112.065 | b) |
| Control #5_center | 120.217 | 119.267 | 119.742 | b) |
| Control #5_pitted edge | 109.751 | 110.147 | 109.949 | b) | a) Samples 5 and 5-1 were halves of the same bead-blasted plate that were surface treated separately as individual samples.
b) after reflux the sample was left overnight at room temperature in the reaction mixture.

The range of contact angles observed was quite broad. Some samples, such as samples 1, 5 and 5-1, showed very high contact angles of the order of 140 degrees (hydrophobic), which indicated that chemical functionalization occurred according to Equation (e4). Samples 2-4 all had substantially lower contact angles, less than 90° (hydrophilic) in some cases, which was even lower than the contact angles of non-blasted controls Control #1 and Control #5 (which had contact angles between 110° and 120°, which is close to the maximum reported water contact angle on a flat PTFE surface (see Inazaki, S.; Oie, T.; Takaoka, H., "Surface modification of poly(tetrafluoroethylene) with ArF excimer laser irradiation," *J. Photopolym. Sci. Technol.* 1994, 7(2): 389-395; Lin, T.-K.; Wu, S.-J.; Peng, C.-K.; Yeh, C.-H., "Surface modification of polytetrafluoroethylene films by plasma pretreatment and graft copolymerization to improve their adhesion to bismaleimide," *Polym. Int.*, 2009, 58(1): 46-53)).

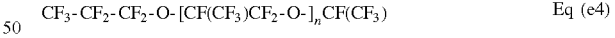
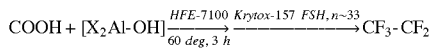

Eq (e4)

$CF_3\text{-}CF_2\text{-}CF_2\text{-}O\text{-}[CF(CF_3)CF_2\text{-}O\text{-}]_n CF(CF_3)$ $COOH + [X_2Al\text{-}OH] \xrightarrow[60\ deg, 3\ h]{HFE\text{-}7100} \xrightarrow{Krytox\text{-}157\ FSH, n\sim33} CF_3\text{-}CF_2$ $\text{-}CF_2\text{-}O\text{-}[CF(CF_3)CF_2\text{-}O\text{-}]_n CF(CF_3)(COOAlX)_2 + H_2O$ As expected, based on the contact angle data, samples 1 and 5, which exhibited the highest contact angles, produced a highly slippery surface when infused with Fluorinert FC-70 Water droplets placed onto these surfaces slid with almost no resistance at very low tilt angles. In contrast, water droplets placed on samples exhibiting low contact angles and defects (e.g., sample 1) were pinned and adhered to the roughened surface even at high tilt angles. The controls, samples Control #1 and Control #5, did produce highly slippery surfaces, but the film of FC-70 did not adhere well to their flat surface.

Surface Treatments

The initial surface cleaning of the samples, including the control samples, was performed by subjecting the samples to sonication for 30 min sequentially in 30% $H_2O_2$, water and absolute ethanol. The samples were then oven-dried in at 100° C. for 30 min.

The roughened, cleaned samples, as well as the respective controls, were placed vertically in a Teflon holder and then into a 500-mL three-neck flask equipped with a reflux condenser, thermocouple, heating mantle and nitrogen blanket (bubbler). The flask was charged with a 3 mM solution of Krytox-157FSH in HFE-7100 (8.46 g in 370.5 mL). The mixture used to surface treat the samples were 30% hydrogen peroxide (Aqua Solutions), absolute ethanol (Pharmco), HFE-7100 (mixture of methyl nonafluorobutyl ether, 30-50%, and methyl nonafluoroisobutyl ether, 70-50%, Miller Stephenson), and Krytox 157 FSH (carboxyl terminated poly(hexafluoropropylene oxide), MW 7000-7500, Miller Stephenson). Water of Millipore grade used was for washes.

Figure 27A:
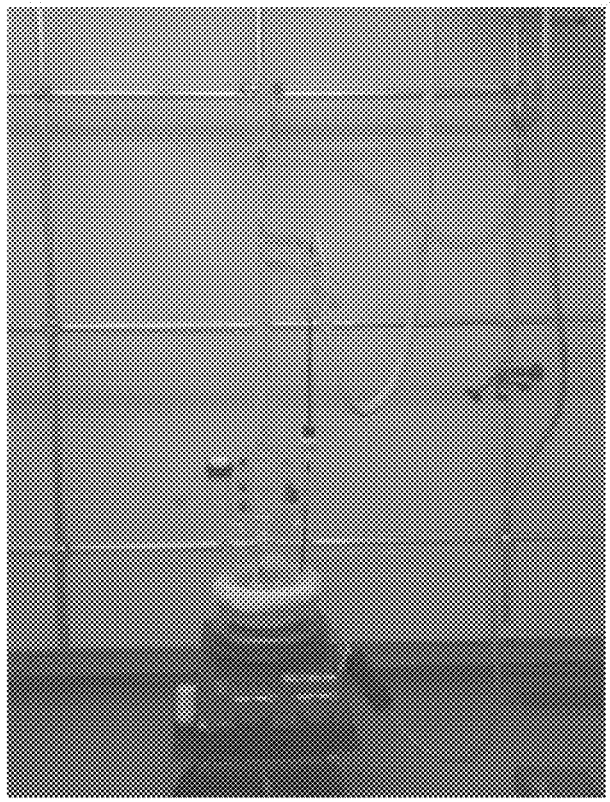
FIG. 27A shows a general view photograph and FIG. 27B shows a zoomed-in view photograph of the experimental setup for the surface treatment of an aluminum alloy to generate roughened aluminum surfaces. Specifically, the reaction mixture is shown fully covering the aluminum plates.
Figure 27B:

The mixture fully covered the plates as shown in FIGS. 27A and 27B. The mixture was refluxed under nitrogen at 60° C. for 3 hours, after which time the samples were removed, rinsed sequentially in 40 mL of HFE-7100 and 40 mL of absolute ethanol, and oven dried at 80° C. for 55 min. The samples were treated two at a time and the solution and rinses were reused in the treatment of the subsequent of samples. A total of four runs with two samples each were performed.

Slippery Liquid-Infused Porous Surface(s) Tests with Water

Figure 28:
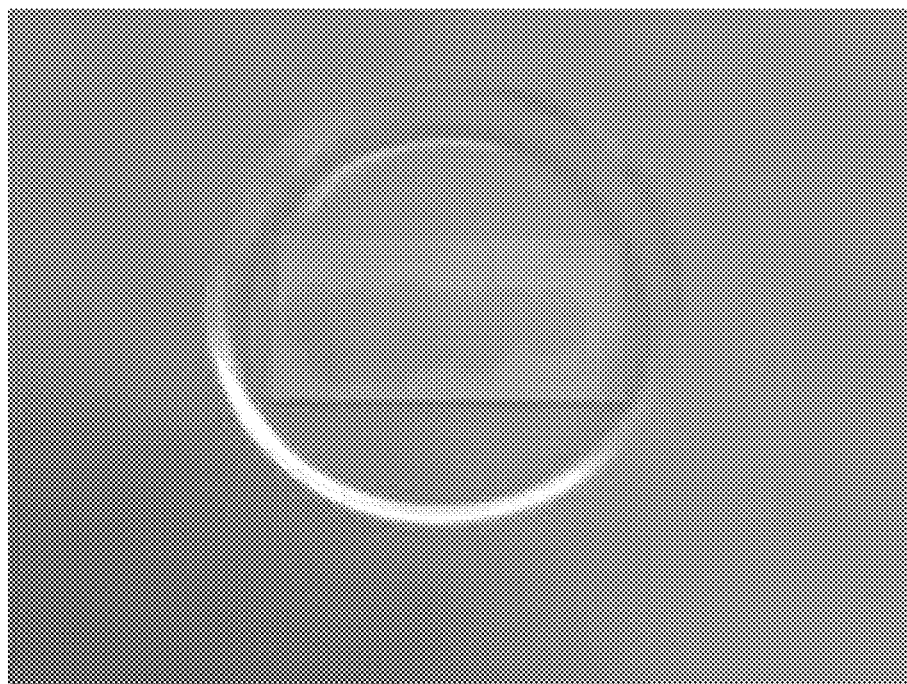
FIG. 28 is an image of FC-70 spreading on the surface of a Krytox-157FSH-pretreated aluminum coupon surface.

Sandblasted, surface-pretreated aluminum coupons (1×2 inch) and surface pretreated controls were infused with FC-70 (Aldrich, lot #MKBF9431V) by placing a total of 60 µL (~130 mg) of FC-70 on the samples. The FC-70 was allowed to spread for several minutes. The sample surfaces were wetted quite readily, as shown in FIG. 28, and resulted in smooth shiny surfaces.

To test the surface of the treated samples for liquid repellency, a single drop of water (30 µL, Millipore) was placed on the aluminum surfaces, and the behavior of the water was observed while the surfaces were tilted in various directions.

A defect in surface treatment was deliberately introduced in some samples. The defect was introduced by placing a 30 µL drop of water in the center of some samples, placing these samples in an oven set to 100° C., and allowing the water to dry on the samples, thus disturbing the integrity of Krytox-157 FSH treatment. The samples were then again infused with FC-70 and subjected to the sliding tests for comparison against the defect-free samples.

Freezing Tests with Water

The treated aluminum samples were placed in a humidity chamber on a cold plate set at −2° C. at 60% relative humidity. Samples 1 and 5 infused with FC-70, along with non-treated, flat Control #1and non-treated, sandblasted Control #5 were subjected to cooling cycles in a humidity chamber. The samples were monitored visually, and the condensation and freezing process taking place was captured by video in real time. Still frames of the video showing the anti-icing behavior of sample 1 (FIG. 29A-F(i)), untreated flat aluminum coupon (FIG. 29A-F(ii)), and untreated sandblasted aluminum coupon (FIG. 29A-F(iii)) are presented in FIGS. 29A-29F.

Samples 1 and 5 behaved similarly during the freezing tests. Both water condensation and subsequent freezing were significantly delayed on samples 1 and 5 compared to their respective controls. In particular, the condensation and freezing were delayed by approximately 20 minutes. Referring to FIG. 29B, which is a still frame of a video taken at 1000 seconds, there was significant condensation on the flat and sandblasted controls, and even the cold plate on which the three samples rested. In contrast, no condensation had formed on the slippery liquid-infused porous surface(s) surface (FIG. 29B(i). FIGS. 29A-29F show example 1 and its controls. The water on the two control surfaces was completely frozen after about 1300 to 1800 seconds (FIGS. 29C(ii), 29C(iii), 29D(ii) and 29D(iii)) while the slippery liquid-infused porous surface(s) surface was only beginning to form condensed droplets at the edges of the coupon (FIGS. 29C(i) and 29D(i)). At 2200 seconds, the two controls were covered with a thick layer of ice (FIG. 29E(ii) and (iii)), as was the cold plate itself, while liquid droplets were visible on slippery liquid-infused porous surface(s) sample 1 (FIG. 29E(i)). At 2600-2700 seconds, the condensed water on slippery liquid-infused porous surface(s) sample 1 froze (FIG. 29F(i)). Thus, the onset of condensation and freezing (i.e., the ability to repel Liquid A and Material A) was substantially delayed on the slippery liquid-infused porous surface(s) surface compared to flat aluminum and sandblasted aluminum controls not chemically modified with perfluorinated long-chain molecules and infused with Liquid B.

Example 11

A scalable and reproducible coating method for creating a slippery surface on an aluminum surface such that the surface not only significantly reduces ice accumulation but allows easy removal of ice that does accumulate was evaluated. Industrial pure aluminum (alloy 1100) is the most widely used material as cooling fins of heat exchangers in refrigeration systems. To create slippery surfaces on an extruded sheet of aluminum 1100, the aluminum was roughened by electrodeposition to first create nanoporous texture. Electrodeposition of PPy can provide fine control of the morphology at the nanometer scale by varying the concentration of the monomer, applied potential, and the deposition time.

Aluminum fins from a refrigerator heat exchanger assembly and rolls of extruded aluminum sheet (aluminum alloy 1100) were cut out from the raw material an flattened by a hydraulic press. The aluminum sheets were ultrasonically cleaned in acetone for 15 minutes and dried under a stream of nitrogen.

Figure 30A:
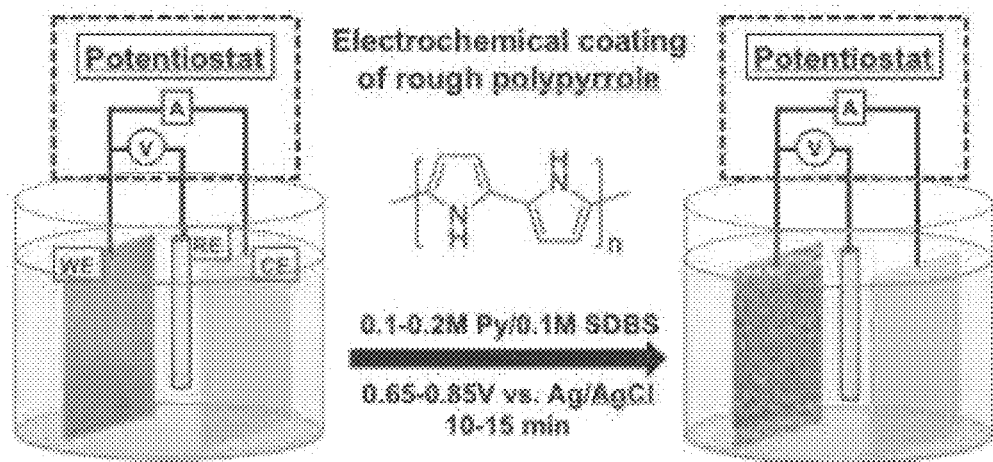
FIG. 30A shows schematics of electrochemical coating of nanostructured polypyrrole on aluminum sheet (WE: Al 1100 alloy as working electrode, RE: Ag/AgCl reference electrode, CE: Pt gauze counter electrode).
Figure 30B:
FIG. 30B shows photographs of untreated punch-pressed aluminum sample (left) and partially coated aluminum sample (right). PPy-coated area appears black in the picture. Substrate size=6 cm×9 cm.

Referring to FIG. 30A, aluminum (alloy 1100) was used as the working electrode (WE) in a standard three-electrode configuration for oxidative electrochemical deposition of PPy. A 0.1-0.2 M pyrrole (Py) solution was made using a 0.1 M sodium dodecylbenzene sulfonate (SDBS) solution as a solvent. The aluminum was used as a working electrode and a platinum gauze was used as a counter electrode. A constant voltage of 0.85 V vs. Ag/AgCl reference electrode (RE) was applied for 5-10 minutes, and the surface of the aluminum gradually turned a dark blue-black color as shown in FIG. 30B. The PPy electrodeposition on aluminum predominantly occurred on the surface facing the platinum mesh counter electrode (CE) and resulted in uniform PPy films of ca. 3-4 µm thick. The PPY film thickness was measured using a stylus profilometer (Dektak 6M, Veeco). The scalability of the method for roughening aluminum in this manner was confirmed by running electrodeposition of PPy over a large area sample (10 cm×10 cm).

Figure 30C:
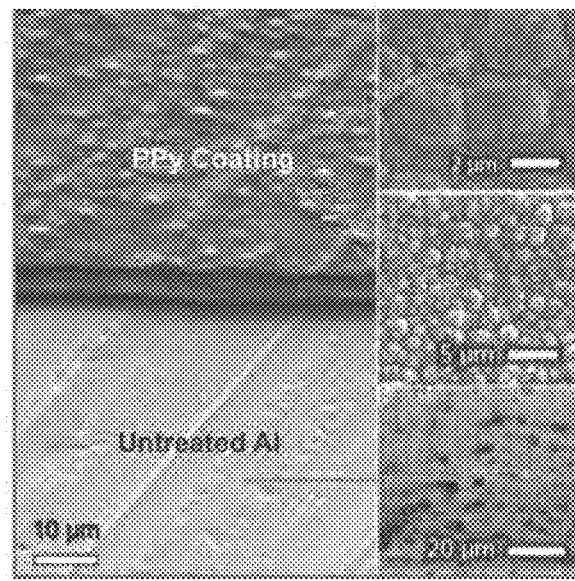
FIG. 30C shows SEM images comparing the morphology of untreated area of aluminum with PPy-coated area. Insets show higher magnification SEM images for the two areas.

SEM images of the PPy coating on aluminum show the rough and globular morphology of the PPy layer with diameters ranging from sub-micrometer up to about 2 micrometers (FIG. 30C). Higher magnification SEM images further revealed the hierarchical nature of the surface coating.

The PPy-coated aluminum samples were hydrophobically modified by placing them under vacuum in a desiccator for 48 hrs with (tridecafluoro-1,1,2,2-tetrahydrooctyl)trichlorosilane. Droplets of perfluoroalkylether (Krytox 100, DuPont) were applied to the silanized surface. The lubricant was applied to cover the surface then the excess lubricant was removed by tilting the substrate until no macroscopic movement of the lubricant on the surface. From the measurement of the weight change, the area of the substrate, and from the density of the lubricant used, it was determined that the average thickness of the lubricant was about 8-10 µm. The surfaces were then held vertically to remove excess lubricating liquid. The thickness of the lubricating film was on the order of 10 µm, which is comparable to the thickness of the small droplets (i.e., $D_c \sim O(100 \mu m)$). This allowed the water droplet to float on the lubricating liquid without interacting with the underlying roughened aluminum surface, rendering the contact angle hysteresis at the liquid-liquid interface negligible. Contact angles of deionized water were measured using a contact angle goniometer (CAM 101, KSV Instruments) at room temperature. Five independent measurements were used to calculate the average advancing and receding contact angle.

The wetting and droplet retention characteristics of unmodified aluminum and slippery liquid-infused porous surface(s) aluminum was explored. A condensed water droplet formed on an inclined, cold, unmodified surface will be initially pinned due to the surface heterogeneity. As the condensation process continues, the basal diameter of the droplet, which has the shape of a spherical cap, increases until it reaches a critical value, $D_C$, beyond which the droplet will slide along the surface. Retention of the droplet on a tilted surface is dictated by two competing forces: gravity and surface tension acting along the contact line of the droplet (i.e., surface retention force). Quantitatively, the critical diameter of the droplet can be estimated by comparing these two forces, which can be expressed as:

$$\rho V g \sin \alpha = \gamma D_c (\cos \theta_R - \cos \theta_A) \quad \text{Eq(e5)}$$

where p is the density of water (997.56 kg/m² at 22.9° C.), V is the volume of the droplet, g is the standard acceleration due to gravity (9.8 m/s²), α is the tilting angle, γ is the surface tension of water (72.6 mN/m at 22.0° C.), $\theta_R$ is the receding contact angle, and $\theta_A$ is the advancing contact angle.

Surface retention force is a function of contact angle hysteresis (CAH, $\Delta\theta = \theta_A - \theta_R$). Thus, by minimizing the hysteresis, the critical size of the water droplets retained on the surface was also minimized, thereby ensuring efficient removal of water droplets from slippery liquid-infused porous surface(s) surfaces before frost and ice formation can occur. The advancing and receding contact angles and the contact angle hysteresis of a macroscopic water droplet, taken at room temperature, was measured to be approximately 5 µL for both untreated aluminum and slippery liquid-infused porous surface(s) aluminum as shown in Table 9. The contact angle hysteresis of slippery liquid-infused porous surface(s)-Al (i.e., $\Delta\theta = 2.3 \pm 1.4°$) was considerably smaller than that of the untreated conventional A1 ($\Delta\theta = 39.5 \pm 2.7°$), which further shows the efficiency of slippery liquid-infused porous surface(s) aluminum surfaces at removing water condensates by sliding.

TABLE 9

Advancing and Receding Contact Angles and the Contact Angle Hysteresis of Untreated Bare Aluminum (Al) and Slippery Liquid-Infused Porous Surface(s)-Al.

| | Advancing Contact Angle[§] (degree) | Receding Contact Angle[§] (degree) | Contact Angle Hysteresis[§] (degree) | Ice Adhesion Force (kPa) (at −10° C.) |
|---|---|---|---|---|
| Al | 44.5 ± 2.5 | 5.0 ± 0.3 | 39.5 ± 2.7 | 1393 ± 231 |
| Slippery Liquid-Infused Porous Surface(s)-Al | 120.5 ± 1.1 | 118.2 ± 1.3 | 2.3 ± 1.4 | 15.6 ± 3.6 |

([§]indicates measurements at room temperature)

Figure 31:
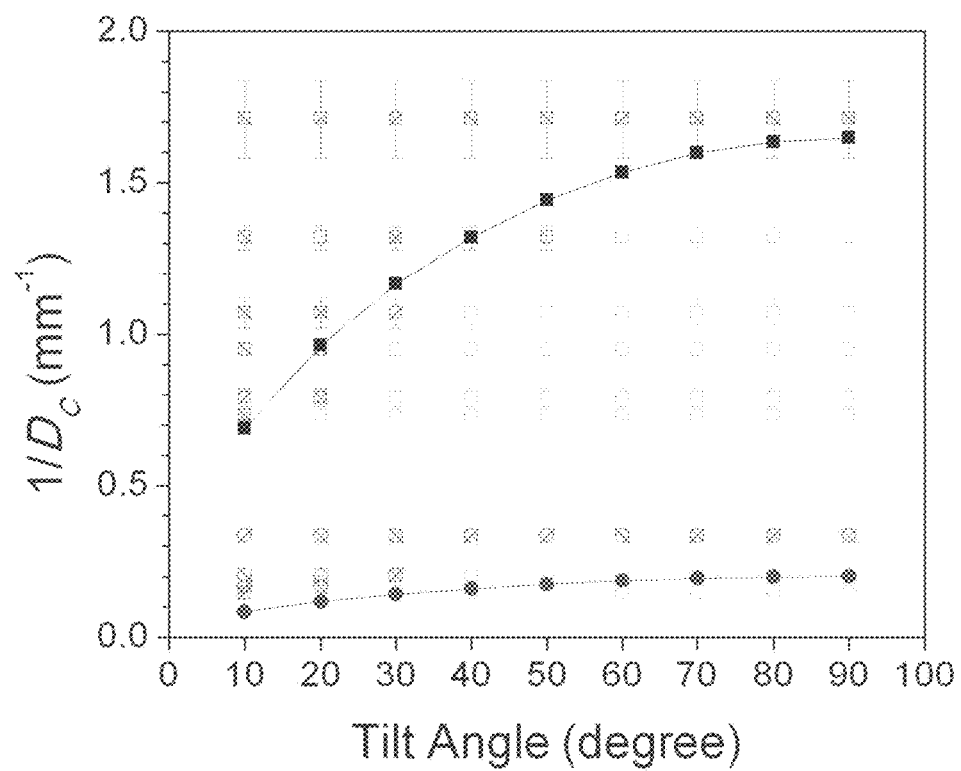
FIG. 31 is a droplet retention plot for untreated aluminum and slippery liquid-infused porous surface(s)-Al. The inverse of the critical droplet size ($D_C$) at each given tilt angle is plotted. The points connected by a line indicate theoretical boundaries for droplets pinning and sliding on Al (circle) and slippery liquid-infused porous surface(s)-Al (square). The water droplets smaller than the critical droplet size corresponding to the area above the curve will remain pinned while the water droplets larger than the critical droplet size corresponding to the area below the curve will slide and be removed from the substrate.
Figures 32A, 32B, 32C:
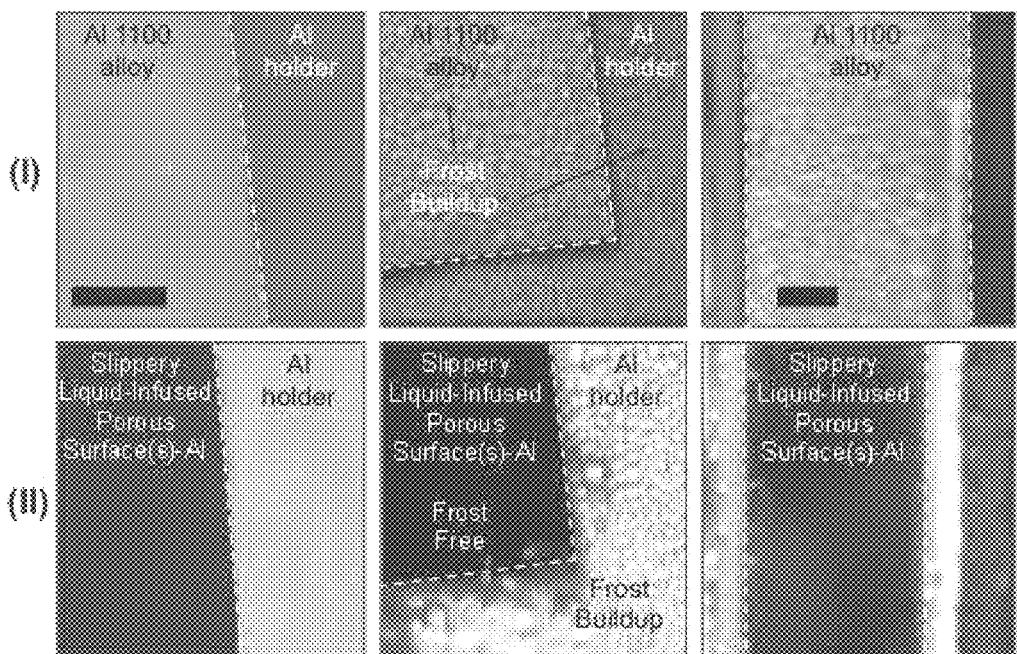
FIGS. 32A through 32C show still images taken from movies recorded during frosting/defrosting tests. An untreated Al 1100 alloy sample (I) and a slippery liquid-infused porous surface(s)-Al sample (II) were mounted on the aluminum holder of a thermoelectric cooler and tilted at 75°. The relative humidity was kept at 60%. Water droplet behavior was observed at room temperature (FIG. 32A), after a cooling cycle at −10° C. at a rate of 2° C./min (FIG. 32B), and after a defrosting cycle to 5° C. at a rate of 5° C./min (c). The black scale bar in I(a), which represents 1 cm, applies to images shown in FIGS. 32B(I), 32A(II) and 32B(II). The scale bar in image shown in FIG. 32C(I) also applies to image shown in FIG. 32C(II). The dashed lines in each frame indicate the borders between different surfaces.

Based on the data in Table 9 and Equation (5), the critical droplet size was estimated to be eight times smaller for slippery liquid-infused porous surface(s)-Al (~600 µm at α=90° to ~1.5 mm at α=10°) than that for bare, unmodified aluminum (~5.0 mm at α=90° to ~12.0 mm at α=10° (see FIG. 31) We have further verified these estimations by observing the sliding behavior and probability of manually-dispensed water droplets on slippery liquid-infused porous surface(s)-Al and A1 at ambient conditions. FIG. 31 also represents these data in which the water droplets smaller than the critical droplet size, corresponding to the area above the curve, will remain pinned on the surface while the water droplets larger than the critical droplet size, corresponding to the area below the curve, will slide due to gravity and be removed from the substrate.

Cooling and defrosting tests were conducted inside a homemade humidity controlled box under humid conditions (60% relative humidity). A thermoelectric cooler was used to precisely control the temperature of the aluminum substrates. FIGS. 32A-32C and FIGS. 41A-41F show images of a slippery liquid-infused porous surface(s)-Al surface and an unmodified aluminum surface at room temperature after a cooling cycle (either −2° C. or −10° C. at 2 degree C./min) and a defrost cycle (5° C. at 5° C./min). Condensation formed on both surfaces in high humidity. Growth of each condensate and the coalescence of droplets resulted in an overall gradual increase of the droplet size over time. Even under a very fast cooling rate, 2° C./min, droplets larger than the critical droplet size for the tilt angle(75°) slid off the slippery liquid-infused porous surface(s)-Al surface before freezing. Droplet growth and sliding on slippery liquid-infused porous surface(s)-Al will be a significant factor in reducing the accumulation of ice under real refrigeration conditions under which the cooling rate is less than 2° C./min. In contrast, all the droplets on the untreated aluminum surface never exceeded the critical droplet size, and therefore did not slid off of the untreated aluminum surface and froze.

Ice adhesion measurements were performed within the humidity controlled chamber used for the frost and defrost testing. Glass columns were made by cutting pasteur pipettes. To hydrophobize the glass, it was exposed to oxygen plasma for 180 seconds and placed under vacuum in a desiccator with (tridecafluoro-1,1,2,2-tetrahydrooctyl) trichlorosilane for at least 24 hours. Slippery liquid-infused porous surface(s)-Al and bare A1 were attached to a temperature controlled aluminum plate using thermally conductive tape and the glass columns were placed on the substrate and filled with 150 µL of freshly distilled, deionized water (Millipore Milli-Q A10). The chamber was then closed and the humidity was lowered below 3% RH in order to minimize frost formation. The temperature of the substrate was lowered at a rate of 2° C./min until ice formed, generally at a substrate temperature of −20° C. After ice formation, the temperature was raised to −10° C. at a rate of 2° C./min and allowed to equilibrate for a minimum of 30 minutes. Force measurements were taken using a Wagner Instruments Force One™ FDIX with a maximum force of 50 N and an accuracy of ±0.25 N. A custom force gauge attachment was used to apply force by either pulling or pushing the sample columns at a contact point less than 1 mm above the surface of the substrate. The force gauge was mounted on a syringe pump (Harvard Apparatus PhD Ultra) that was moved forwards and backwards at a precise rate: 0.5 mm/s for A1 and 0.1 mm/s for slippery liquid-infused porous surface(s)-Al due to the large difference in the ice adhesion. Ice adhesion data is shown in Table 9. Slippery liquid-infused porous surface(s)-Al showed about two orders of magnitude decrease in the ice adhesion strength than that of conventional aluminum surface, and at least an order of magnitude decrease in the ice adhesion strength than that of state-of-the-art icephobic surfaces (ice adhesion strength ~160 kPa).

Figures 42A, 42B, 42C:
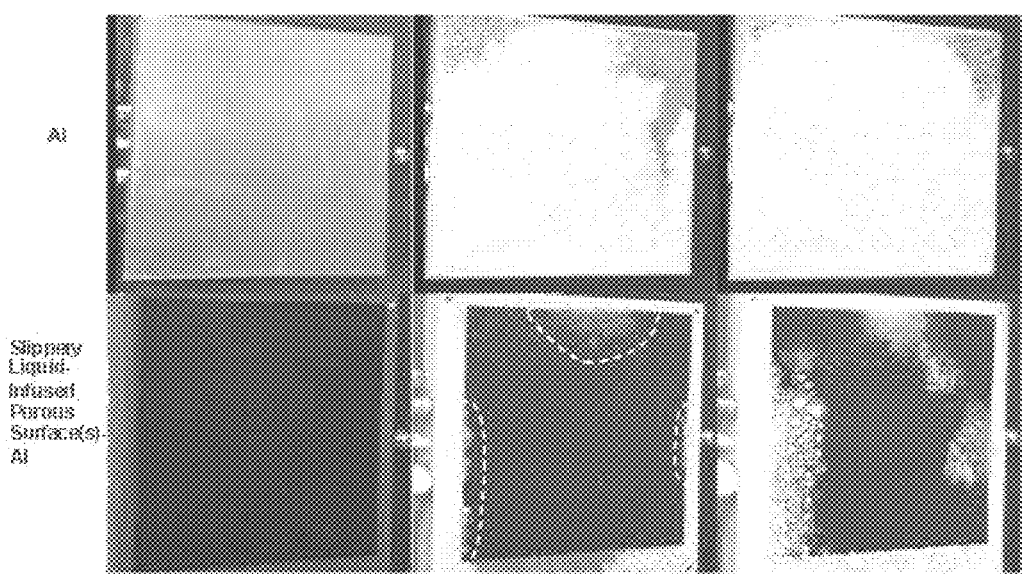
FIGS. 42A through 42C show a series of still images extracted from the movies showing the difference of the morphology of accumulated ice on untreated Al and slippery liquid-infused porous surface(s)-Al.
Figure 43:
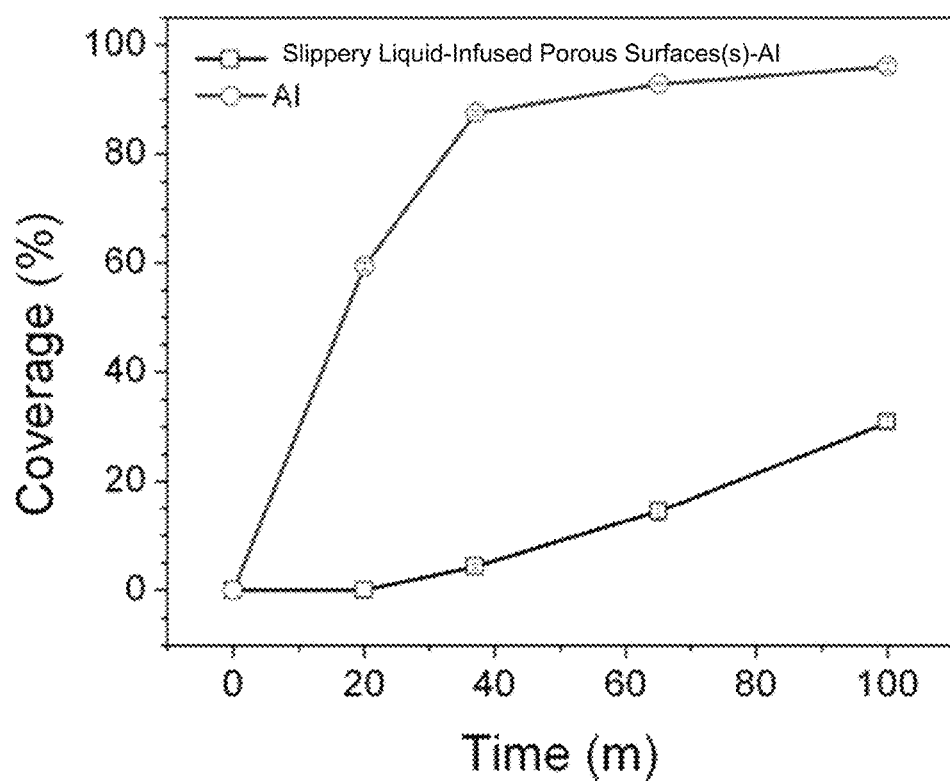
FIG. 43 is a ploto % frost coverage with time illustrating the relative surface coverage of frost on Al and slippery liquid-infused porous surface(s)-Al in FIGS. 42A-42C.
Figure 44:
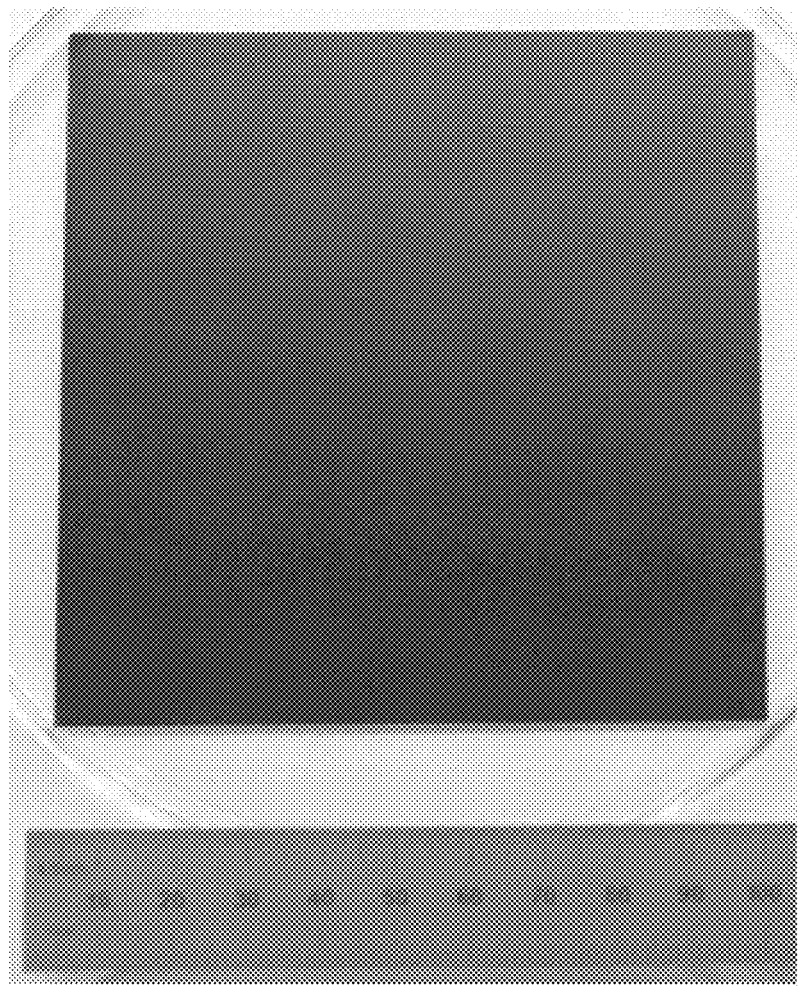
FIG. 44 is a photograph of a PPy-coated Al 1100 sample of 10 cm×10 cm demonstrating the uniformity of the coating and the scalability.

Under a prolonged low temperature (e.g., <−10° C.) and high humidity condition (>50% RH), slippery liquid-infused porous surface(s)-Al surfaces eventually accumulate ice, typically from the edges connected to other non-slippery liquid-infused porous surface(s) surfaces as shown in FIGS. 42A-42C. FIG. 43 is a plot of % frost coverage with time illustrating the relative surface coverage of frost on Al and slippery liquid-infused porous surface(s)-Al in FIGS. 42A-42C. However, the morphology of the ice formed on slippery liquid-infused porous surface(s)-Al was significantly different from that of untreated A1 primarily due to the difference in the contact angle as similarly observed on other lotus-leaf inspired superhydrophobic surfaces. In addition, since some of the large sliding supercooled water droplets can freeze upon finding a nucleation site on the surface during sliding, there tend to be large and isolated patches of ice on slippery liquid-infused porous surface(s)-Al. During the defrost cycle, these large ice patches were removed quickly due to their large weight as soon as the melting at the interface with the slippery liquid-infused porous surface(s)-Al surface took place near melting temperature. Subsequently, smaller ice accretions slid off the slippery liquid-infused porous surface(s)-Al surface leaving the surface clean and ready for the next cooling cycle almost instantaneously (~1 min).

In contrast, the ice accretions on bare aluminum tend to have morphology of densely packed sheet that were hardly removed in a defrost cycle. Moreover, even when most of the ice was removed there were still many droplets retained on the surface that must be removed by elevating the temperature of the aluminum for a long time (typically 15-30 minutes) before starting the next cooling cycle.

Example 12

Figure 33A:
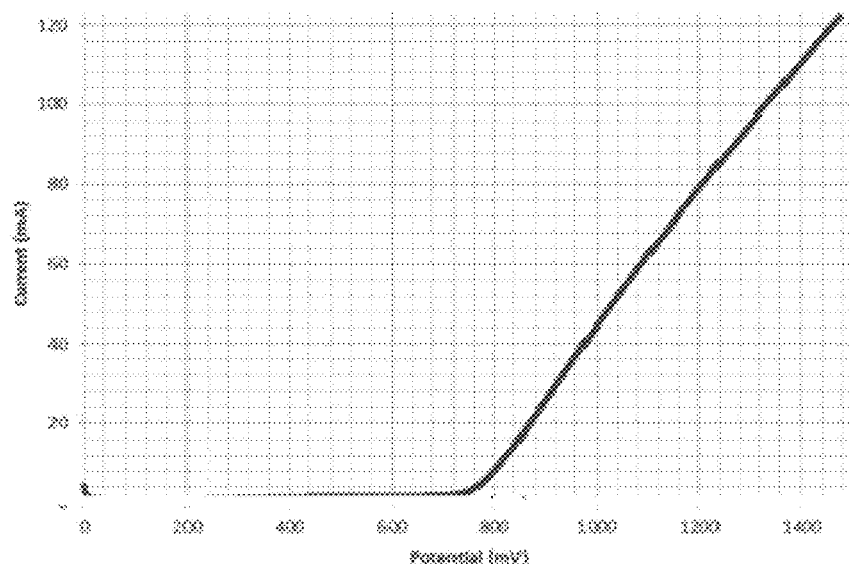
FIGS. 33A and 33B show graphs used to determine the electrodeposition potential for observing polypyrrole growth (FIG. 33A) and a chronoamperogram showing the values recorded during the PPy coating process of aluminum (FIG. 33B)

A linear scan voltammogram (LSV) using aluminum 1100 as the working electrode was used to record a voltage sweep from 0 V to 1.5 V with a scan rate of 0.01 V/s in a PPy-coating solution (0.1-0.2 M pyrrole (Py) solution with 0.1 M SDBS solution as a solvent). Referring to FIG. 33A, polypyrrole growth was observed at about 0.75 V as indicated by the increase of the Faradaic current, which defined the lowest possible voltage range in order to electropolymerize pyrrole. Based on this graph, 0.85 V was chosen as the electrodeposition potential.

Figure 33B:
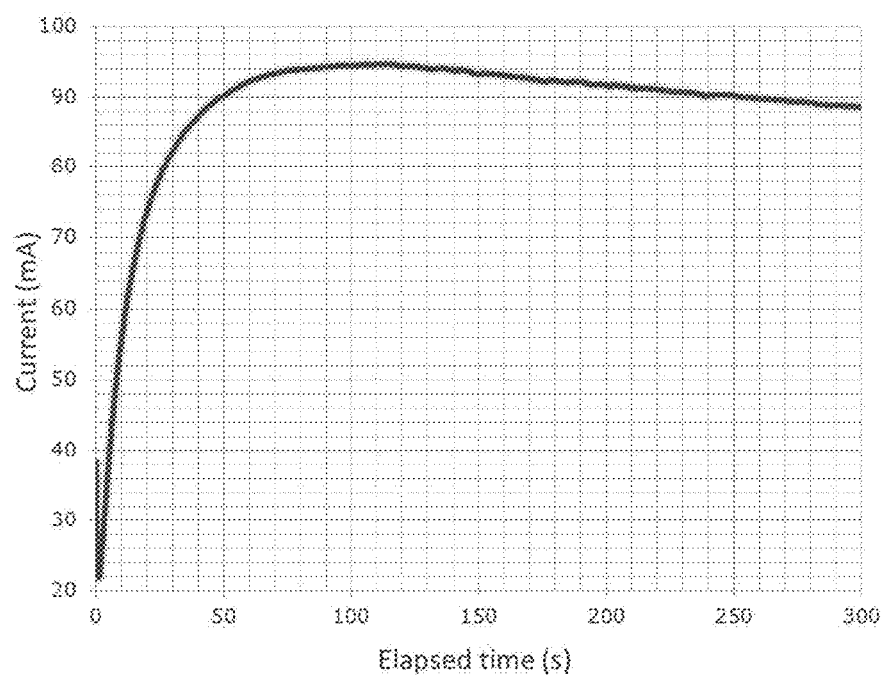
Figure 34:
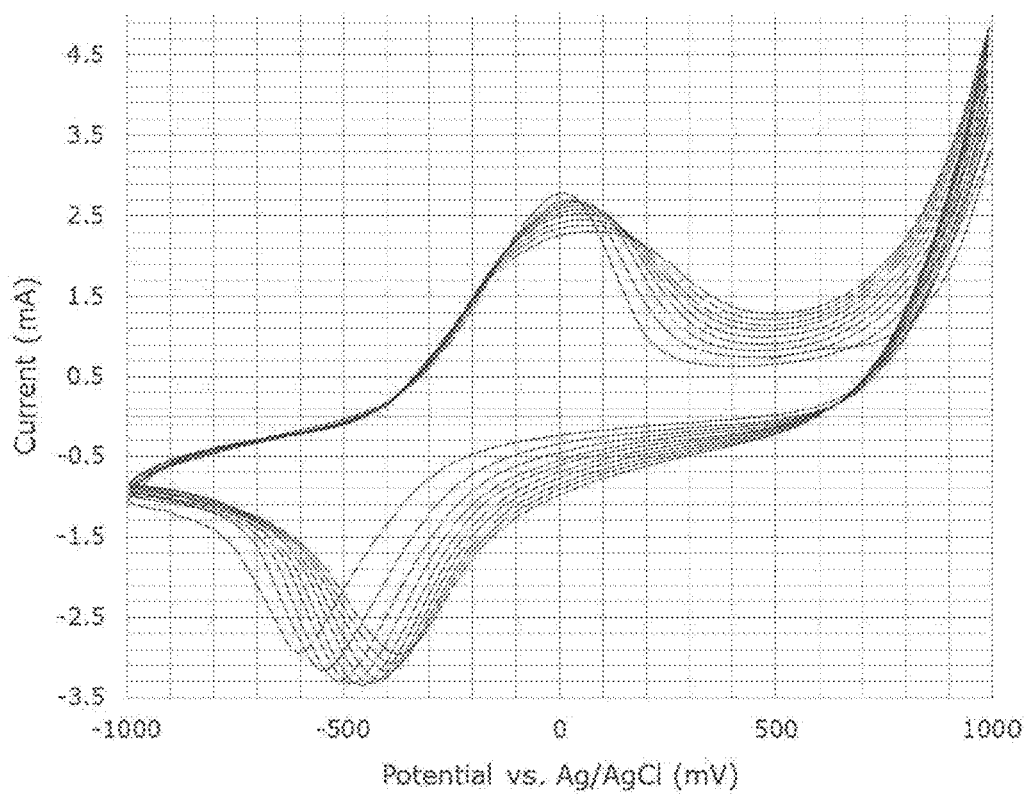
FIG. 34 is a graph showing the cyclic voltammetry of a PPy coating on an aluminum substrate in 0.1 M SDBS solution. The potential of the initial 75 seconds was swept at 0.1 V/s, between −0.85 and +0.5 V.
Figure 35:
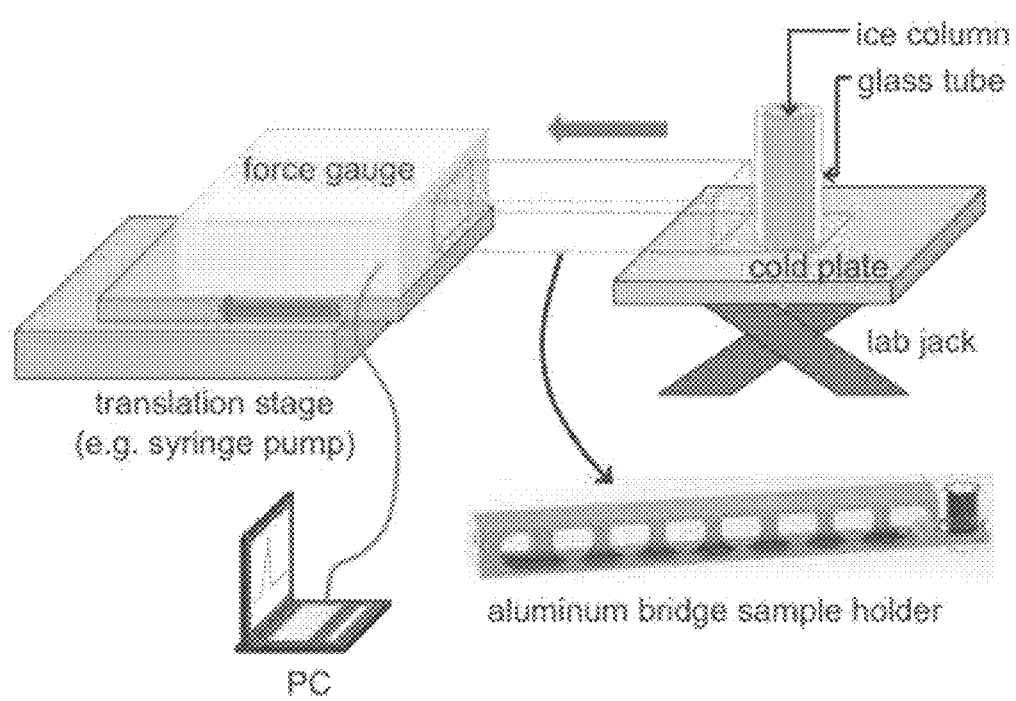
FIG. 35 is a schematic of a set up for an ice adhesion test.

A typical chronoamperogram (current vs. time) was recorded during the PPy coating process (FIG. 33B). The dimension of the substrate was about 3 cm×8 cm (average current density was about 3.8 mA/cm$^2$). The current density varied for substrates of different sizes. For example, for a 8 cm×8 cm substrate, the current density was kept about 1.9 mA/cm$^2$ to achieve an optimal PPy coating. FIG. 34 shows the cyclic voltammetry of a PPy coating on an aluminum substrate in 0.1 M SDBS solution. The potential of the initial 75 seconds was swept at 0.1 V/s, between −0.85 and +0.5 V.

Example 13

Mechanical/(electro)chemical methods were used to roughen A1 alloy for structural material used in aircraft and transportation equipment. This method was used on Al alloy 5052 for marine equipment, and A1 alloy 6061-T6 for structural, building, and architectural applications. These alloys were sandblasted to obtain roughnesses (Ra) ranging 1.35-3.4 μm. The roughened alloys were then chemical functionalized with Krytox 157 FSH (carboxyl terminated poly(hexafluoropropylene oxide) by refluxing in HFE-7100 (a mixture of methyl nonafluorobutyl and methyl nonafluoroisobutyl ethers). The water contact angle of aluminum surface increased to ~140° after chemical surface modification. Application of lubricating liquid to these roughened and chemically modified surfaces provided ultra-repellent aluminum surfaces. Metal surfaces can be functionalized using different surface modifiers (such as, e.g., polyfluorinated chlorosilanes or polyfluorinated phosphonic acids, or even appropriate non-fluorinated long-chain modifiers—see Example 15) or/and different conditions.

Example 14

Boehmite (γ-AlO(OH)) formation on an aluminum alloy (Al 1100) was performed to roughen the metal. Several aluminum samples were boiled in hot water for either 3, 5, or 10 minutes and then rinsed with cold water. The samples were then placed in a 20 mM solution of octadecylphosphonic acid in a 95:5 (v/v) mixture of ethanol and water, and stirred for 1 hour at 80° C. After cooling, the samples were rinsed with ethanol. Application of lubricating liquid rendered these surfaces ultra-repellant.

EXAMPLE

The effectiveness of slippery liquid-infused porous surface(s) under flow conditions was evaluated by studying the effect of several variables on the rate of Liquid B leaching into a Liquid A and the associated loss of slipperiness. Water was used as Liquid A.

Figure 38:
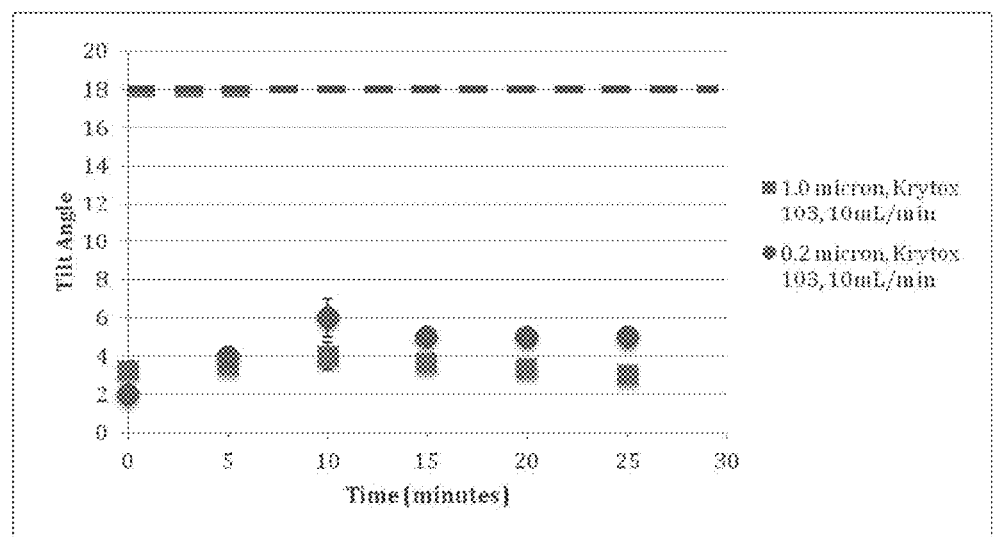
FIG. 38 is a graph that shows the effect of membrane pore size on slippery liquid-infused porous surface(s) performance under flow conditions. The circle represents a sample made from 0.2 µm Teflon membranes and the square represents a sample made from 1.0 µm Teflon membranes. Performance of dry Teflon (non-slippery liquid-infused porous surface(s)) membrane is represented by a dashed-line. A 50 µL droplet of water was used.
Figure 39:
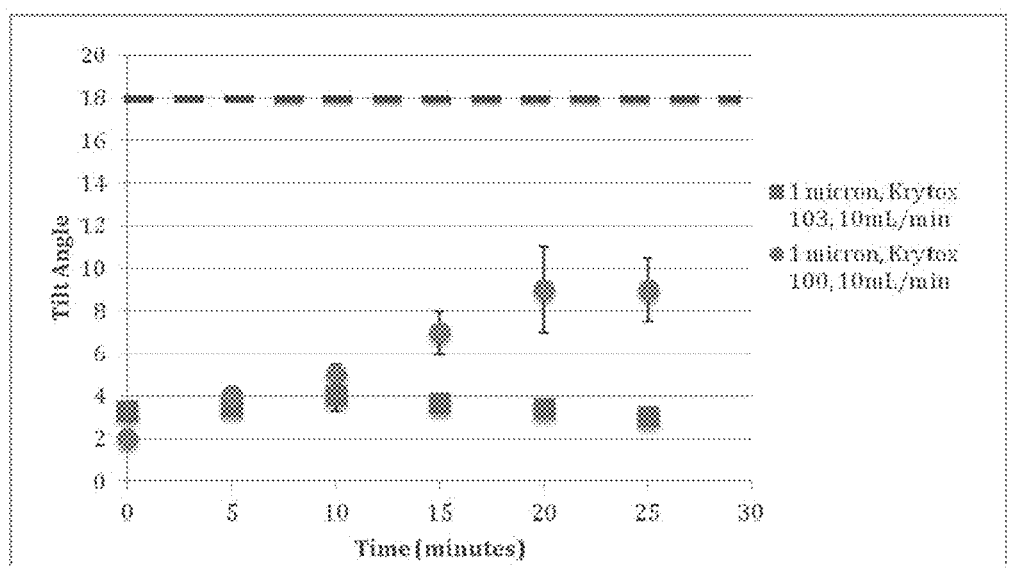
FIG. 39 is a graph that shows the effect of lubricant viscosity on slippery liquid-infused porous surface(s) performance under flow conditions, and that lubricating liquids with lower viscosities are worn off from the slippery liquid-infused porous surface(s) surface faster than lubricating liquids of higher viscosities.

To test the physical wearing of lubricant from slippery liquid-infused porous surface(s) into a flowing fluid, water flowed through a slippery liquid-infused porous surface(s)-lined channel at a controlled rate for an extended period of time. The tilt angles of a 50 μm water droplet on the slippery liquid-infused porous surface(s) surface was measured every five minutes to gauge the slipperiness of the slippery liquid-infused porous surface(s) surface (see FIGS. 38-39). Referring to FIG. 38, no significant effect on slippery liquid-infused porous surface(s)' ability to repel the water was observed when comparing 0.2 μm pore and 1.0 μm size membranes. FIG. 39 shows that lubricant viscosity had little effect on slippery liquid-infused porous surface(s) performance under flow conditions (p-value=0.05), and lubricating liquids with lower viscosities (Krytox 100=12.4 cSt)

were removed from the slippery liquid-infused porous surface(s) surface faster than lubricating liquids of higher viscosities (Krytox 103=82 cSt).

Figure 40:
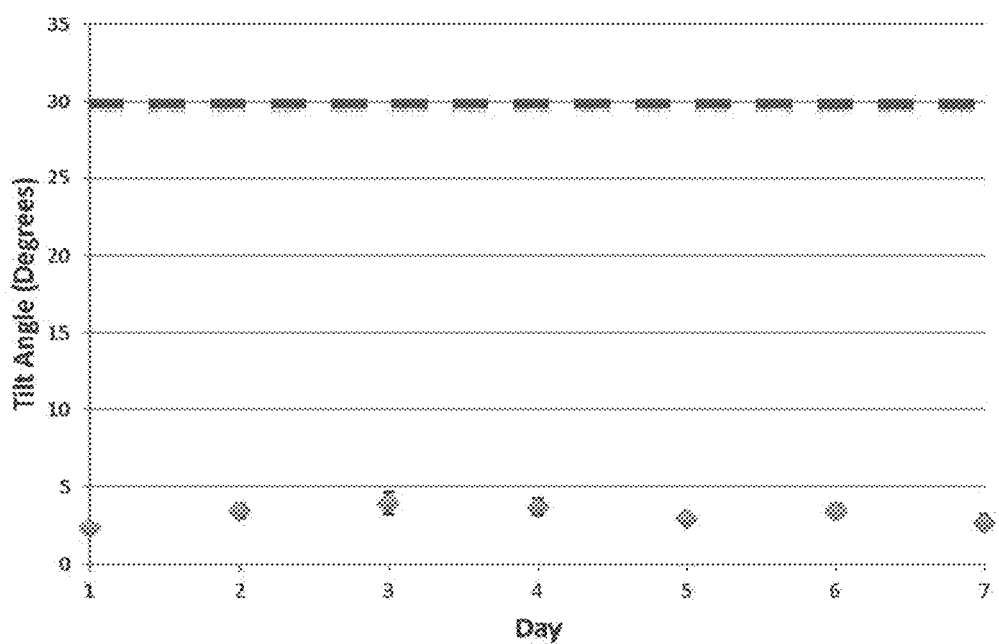
FIG. 40 is a graph which shows that there was no degradation in performance of the slippery liquid-infused porous surface(s) during the seven-day period at a flow rate of 10 mL/min.
Figures 41A, 41B, 41C, 41D, 41E, 41F:
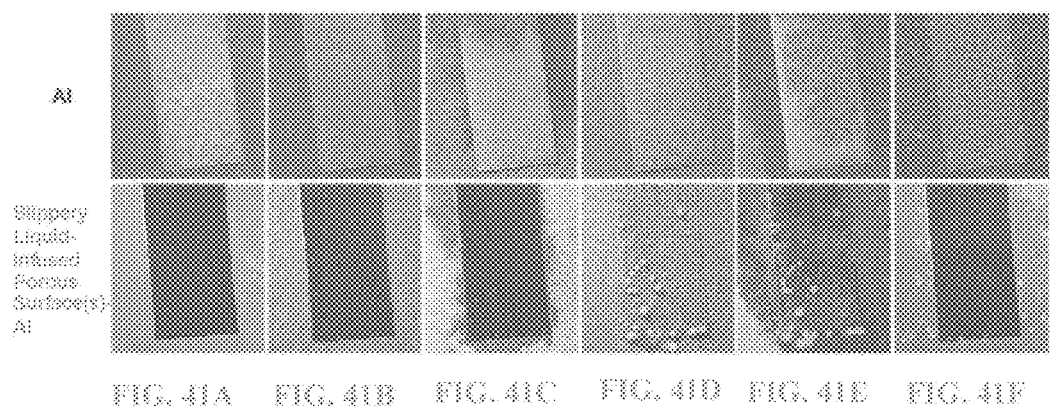
FIGS. 41A through 41F show is a series of still images extracted from the movies showing the difference of the morphology of accumulated ice on untreated Al and slippery liquid-infused porous surface(s)-Al.

Long term stability of slippery liquid-infused porous surface(s) under flow condition was assessed by extending the above test to seven days slippery liquid-infused porous surface(s) was manufactured from a Teflon membrane (0.2 µm pore size) with Krytox 103 as Liquid B. The slippery liquid-infused porous surface(s)-integrated channel was tested at a flow rate of 10 mL/min. FIG. 40 shows that, under these flow conditions, there was no degradation in performance of the slippery liquid-infused porous surface(s) during the seven-day period.

Upon review of the description and embodiments of the present invention, those skilled in the art will understand that modifications and equivalent substitutions may be performed in carrying out the invention without departing from the essence of the invention. Thus, the invention is not meant to be limiting by the embodiments described explicitly above, and is limited only by the claims which follow.

What is claimed is:

1. An article comprising a slippery surface capable of reducing adhesion of a foreign material to the article,
    wherein the article is a component of a sanitation system;
    wherein the article comprises:
    (i) a substrate comprising a roughened surface, and
    (ii) a lubricating liquid having a chemical affinity for the roughened surface, as determined by an equilibrium contact angle of less than 90°, to wet spontaneously the substrate, the lubricating liquid wetting and adhering to the roughened surface to provide a stabilized liquid overlayer on the roughened surface, without dewetting from the substrate, to form the slippery surface; and
    wherein the foreign material comprises waste water, dirt, a fecal matter, urine, blood, a bacterium, a virus, a fungus, a bodily fluid, a tissue, or a combination thereof.

2. The article according to claim 1, wherein the article is a toilet or a sink.

3. The article according to claim 1, wherein the chemical affinity of the lubricating liquid for the roughened surface is determined by an equilibrium contact angle of less than 90°.

4. The article according to claim 1, wherein the roughened surface comprises one or more functional groups chemically attached to the roughened surface; and
    wherein the lubricating liquid has a chemical affinity for the one or more functional groups.

5. The article according to claim 4, wherein the one or more functional groups are selected from the group consisting of a fluorinated carboxylic acid, a fluorinated phosphonic acid, a fluorinated sulfonic acid, a fluorinated silane, an end-functionalized fluorinated polymer, a straight-chain or branched-chain fluorocarbon, a straight-chain or branched-chain hydrocarbon, and a combination thereof.

6. The article according to claim 1, wherein the roughened surface has a predetermined roughness; and
    wherein the predetermined roughness is effective to immobilize the lubricating liquid on the roughened surface.

7. The article according to claim 1, wherein the substrate comprises a plurality of raised structures; and
    wherein the plurality of raised structures have feature sizes ranging from about 10 nm to about 100 µm, and are substantially free of three-dimensionally interconnected pores.

8. The article according to claim 1, wherein the substrate comprises a glass, a ceramic, a plastic, a rubber, a metal, or a combination thereof.

9. The article according to claim 1, wherein the lubricating liquid is selected from the group consisting of fully or partially fluorinated carboxylic acids, fully or partially fluorinated phosphonic acids, fully or partially fluorinated sulfonic acids, fully or partially fluorinated silanes, fully or partially fluorinated hydrocarbons, fully or partially fluorinated organosilicone compounds, fully or partially fluorinated alkylamines, fully or partially fluorinated alkylsulfides, fully or partially fluorinated alkylsulfoxides, fully or partially fluorinated alkylethers, fully or partially fluorinated cycloethers, fully or partially fluorinated polyethers, fully or partially fluorinated alkylphosphines, fully or partially fluorinated phosphineoxides, liquid hydrocarbons, oils, and mixtures thereof.

10. The article according to claim 1, wherein the lubricating liquid comprises an oil.

11. The article according to claim 1, wherein the article further comprises a reservoir containing additional lubricating liquid, and
    wherein the additional lubricating liquid replenishes the lubricating liquid on the roughened surface.

12. The article according to claim 11, wherein the article is a toilet; and
    wherein the lubricating liquid is flushed into the toilet bowl to replenish the lubricating liquid on the roughened surface.

13. The article according to claim 1, wherein the article is a toilet;
    wherein the substrate comprises a ceramic;
    wherein the roughened surface comprises one or more functional groups chemically attached to the roughened surface;
    wherein the lubricating liquid has a chemical affinity for the one or more functional groups; and
    wherein the foreign material comprises a fecal matter, a bodily fluid, or a combination thereof.

* * * * *